United States Patent
Cantrell et al.

(10) Patent No.: US 6,576,803 B2
(45) Date of Patent: Jun. 10, 2003

(54) CATALYSTS FOR THE OXIDATIVE DEHYDROGENATION OF HYDROCARBONS

(75) Inventors: Rick David Cantrell, Sugar Land, TX (US); Anca Ghenciu, Charleston, WV (US); Kenneth Dwight Campbell, Whitesburg, KY (US); David Michael Anthony Minahan, Cross Lanes, WV (US); Madan Mohan Bhasin, Charleston, WV (US); Alistair Duncan Westwood, Easton, PA (US); Kenneth Andrew Nielsen, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 10/124,564

(22) Filed: Apr. 16, 2002

(65) Prior Publication Data

US 2002/0173420 A1 Nov. 21, 2002

Related U.S. Application Data

(62) Division of application No. 09/664,954, filed on Sep. 18, 2000, now Pat. No. 6,403,523.

(51) Int. Cl.[7] .................... C07C 5/327; C07C 5/373; C07C 5/333; C07C 255/00; C07D 211/70
(52) U.S. Cl. .................. 585/654; 585/661; 546/352; 558/383
(58) Field of Search ................. 502/174, 302, 502/303, 305, 311, 313, 318, 324, 340; 546/352; 558/383; 585/654, 661

(56) References Cited

U.S. PATENT DOCUMENTS

| 3,925,498 A | * | 12/1975 | Stadig ................... 260/680 E |
| 3,933,932 A | * | 1/1976 | Vrieland et al. ........ 260/669 R |
| 4,497,785 A | * | 2/1985 | Tilley et al. ................. 423/263 |
| 4,499,323 A | | 2/1985 | Gaffney ..................... 585/500 |
| 4,499,324 A | | 2/1985 | Gaffney ..................... 585/500 |
| 4,727,211 A | | 2/1988 | Gaffney ..................... 585/500 |

(List continued on next page.)

OTHER PUBLICATIONS

Walsh, D.E., et al., "Direct Oxidative Methane Conversion at Elevated Pressure and Moderate Temperatures", *Ind. Eng. Chem. Res.* 1992, 31, 1259–1262. Month not available.

(List continued on next page.)

*Primary Examiner*—Elizabeth Wood
*Assistant Examiner*—Patricia L. Hailey

(57) ABSTRACT

The present invention provides a catalyst for the oxidative dehydrogenation of a lower hydrocarbon to form at least one higher hydrocarbon and/or lower olefin. In one embodiment, the catalyst includes a nonstoichiometric rare earth oxycarbonate of the formula $M_xC_yO_z$ having a disordered and/or defect structure, wherein M is at least one rare earth element selected from the group consisting of La, Pr, Nd, Sm, Eu, Gd, Tb, Dy, Ho, Er, and Tm; X=2; Z=3+AY; A is less than about 1.8, and Y is the number of carbon atoms in the oxycarbonate. When used for the oxidative dehydrogenation of a lower hydrocarbon at a pressure above about 100 psig, the catalyst has a selectivity of at least about 40% to at least one higher hydrocarbon and/or lower olefin. Methods for preparing catalysts taught by the invention and processes for using the catalysts for the oxidative dehydrogenation of lower hydrocarbons are also provided.

14 Claims, 19 Drawing Sheets

U.S. PATENT DOCUMENTS

| | | | | |
|---|---|---|---|---|
| 4,727,212 | A | | 2/1988 | Gaffney ...................... 585/500 |
| 4,777,319 | A | * | 10/1988 | Kung et al. .................. 585/624 |
| 4,780,449 | A | | 10/1988 | Hicks .......................... 502/303 |
| 4,929,787 | A | | 5/1990 | Cameron et al. ........... 585/500 |
| 4,937,059 | A | | 6/1990 | Kolts et al. .................. 423/230 |
| 5,025,108 | A | | 6/1991 | Cameron et al. ........... 585/500 |
| 5,061,670 | A | | 10/1991 | Forquy et al. .............. 585/500 |
| 5,113,032 | A | | 5/1992 | Cameron et al. ........... 585/500 |
| 5,146,027 | A | | 9/1992 | Gaffney ...................... 585/500 |
| 5,210,357 | A | | 5/1993 | Kolts et al. .................. 585/500 |
| 5,496,528 | A | | 3/1996 | David et al. ................ 423/263 |
| 5,567,667 | A | | 10/1996 | Morris et al. ............... 502/302 |
| 5,712,217 | A | | 1/1998 | Choudhary et al. ......... 502/303 |
| 5,739,075 | A | * | 4/1998 | Matusz ....................... 502/302 |
| 6,087,545 | A | * | 7/2000 | Choudhary et al. ......... 585/658 |
| 6,403,523 | B1 | * | 6/2002 | Cantrell et al. ............. 502/174 |

OTHER PUBLICATIONS

Walsh, D.E., et al., "Pressure, Temperature, and Product Yield Relationships in Direct Oxidative Methane Conversion at Elevated Pressures and Moderate Temperatures", *Ind. Eng. Chem. Res.* 1992, 31, 2422–2425. Month not available.

Taylor, R.P., et al., "Lanthanum Catalysts for CH4 Oxidative Coupling: A Comparison of the Reactivity of Phases", *Ind. Eng. Chem. Res.* 1991, 30, 1016–1023. Month not available.

DeBoy, J.M. et al., "The Oxidative Coupling of Methane over Alkali, Alkaline Earth, and Rare Earth Oxides", *Ind. Eng. Chem. Res.* 1988, 27, 1577–1582. Month not available.

Mimoun, H. et al., "Oxidative Coupling of Methane Followed by Ethane Pyrolysis", *Chemistry Letters*, (1989), pp. 2185–2188. Month not available.

Bernal, S. et al., "Oxidation Dehydrogenation of Ethane over Lanthana: Actual Nature of the Active Phase", *Catalysis Letters* 6 (Jul. 1990) 231–238. Month not available.

Le Van T. et al., "Structure Sensitivity of the Catalytic Oxidative Coupling of Methane on Lanthanum Oxide", *Catalysis Letters* 6 (Aug. 1990) 395–400.

Pinabiau–Carlier, M. et al., "The Effect of Total Pressure on the Oxidative Coupling of Methane Reaction Under Cofeed Conditions", A. Holmen et al., (Editors), *Natural Gas Conversion* (1991), pp. 183–190, Month not available.

Taylor, R.P. et al., "Isotopic Labeling Studies of C and O atoms for Methane Oxidative Coupling Over II–La2O2CO3", *Natural Gas Conversion II* (1994), pp. 235–240. Month not available.

Lacombe, S. et al., "Total Oxidation Pathways in Oxidative Coupling of Methane Over Lanthanum Oxide Catalysts", *Catalysis Today*, 13 (1992) 273–282. Month not available.

Louis, C. et al., "EPR Study of the Stability and the Role of the O2–Species on La2O3 in the Oxidative Coupling of Mathane", *Catalysis Today*, 13 (1992) 283–289.

Le Van, T. et al., "Temperature and Conversion Dependence of Selectivities in the Oxidative Coupling of Methane on La2O3 Catalysts", *Catalysis Today*, 13 (1992) 321–328. Month not available.

Olsbye U. et al., "A Comparative Study of Coprecipitated BaCO3/La2On(CO3)m Catalysts for the Oxidative Coupling of Methane", *Catalysis today*, 13(1992) 603–608. Month not available.

Holsa, J. et al., "Preparation, Thermal Stability and Luminescence Properties of Selected Rare Earth Oxycarbonates", *Thermochimica Acta*, 190 (Mar. 1991) 335–343.

Bernal, S. et al., "Thermal Evolution of a Sample of La2O3 Exposed to the Atmosphere", *Thermochimica Acta*, 66 (Jan. 1983) 139–145.

Squire, G.D. et al., "In Situ X–ray Diffraction Study of Lanthanum Oxide Catalysts During the Oxidative Coupling of Methane", *Applied Catalysis A: General*, 108 (Sep. 1994) 261–278.

Ekstrom, A., et al., "Effect of Pressure on the Oxidative Coupling Reaction of Methane", *Applied Catalysis*, 62 (Feb. 1990) 253–269.

Conway, S.J. et al., "Comparison of Lanthanum Oxide and Strontium–Modified Lanthanum Oxide Catalysts for the Oxidative Coupling of Methane", *Applied Catalysis A: General*, 86 (Apr. 1992) 199–212.

Choudhary, V.R., et al., "Acidity/Basicity of Rare–Earth Oxides and their Catalytic Activity in Oxidative Coupling of Methane to C2–Hydrocarbons", *Journal of Catalysis* 130, 411–422 (Jan. 1991).

Otsuka, K. et al., "Active and Selective Catalysts for the Synthesis of C2H4 and C2H6 via Oxidative Coupling of Methane", *Journal of Catalysis* 100, 353–359 (Mar. 1986).

Le Van, T. et al., "Infrared Study of the Formation and Stability of La2O2CO3 during the Oxidative Coupling of Methane on La2O3", *Journal of Catalysis* 142, 18–26 (Feb. 1993).

Foger, K. et al., "Formation and Thermal Decomposition of Rare–Earth Carbonates", *Journal of Materials Science* 27 (1992) 77–82. Month not available.

Watanabe, Yoshihiko, et al., "Dissociation Pressure of Lanthanum Dioxide Carbonate", *Journal of Materials Science Letters* 5 (1986) 135–136. Month not available.

Alvero, R. et al., "Lanthanide Oxides: Preparation and Ageing", *J. Chem. Soc. Dalton Trans.* 1984, 87–91. Month not available.

DeBoy, J.M. et al., "Oxidative Coupling of Methane Over Alkaline Earth Promoted La2O3", *J. Chem. Soc., Chem. Commun.*, 1988, 982–984. Month not available.

Choudhary, V.R. et al., "Oxidative Coupling of Methane over La2O3", *J. Chem. Soc. Paraday Trans.*, 1994, 90(21), 3357–3365. Month not available.

Campbell, K.D., "Methane Activation by the Lanthanide Oxides", *J. Phys. Chem.* 1988, 92, 750–753, Aug. 1987.

Turcotte, R.P. et al., "On the Rare Earth Dioxymonocarbonates and their Decoposition", *inorganic Chemistry* vol. 8, No. 2, (Feb. 1969) 238–246.

Chen, L.Y. et al., "Properties of Lanthanabased Catalysts for the Oxidative Coupling of Methane", *J. Fuel Chem. and Techn.*, vol. 22, No. 4, pp. 337–342, Jan. 1994.

Hengxiu, W. et al., "Study on Oxidative Coupling of Methane Over Various Lanthanum Compounds", *N. American Catalysis Soc. Meeting*, 1997, p121. Month not available.

* cited by examiner

• NONSTOICHIOMETRIC OXYCARBONATES (MEASURED DATA)

■ STOICHIOMETRIC OXYCARBONATES (PRIOR ART)

Long Range Order

CATALYSTS FOR THE OXIDATIVE DEHYDROGENATION OF HYDROCARBONS

CROSS-REFERENCE TO RELATED APPLICATION

This application is a divisional of prior application Ser. No. 09/664,954, filed Sep. 18, 2000 now U.S. Pat. No. 6,403,523.

FIELD OF THE INVENTION

This invention relates, in general, to the oxidative dehydrogenation of hydrocarbons. More particularly, the present invention relates to rare earth catalysts that provide unusually high selectivity to higher hydrocarbons and/or lower olefins when used for the oxidative dehydrogenation of a lower hydrocarbon at elevated pressure. Accordingly, the rare earth catalysts of the invention are particularly useful for coupling methane by oxidative dehydration to form ethane, ethylene and higher hydrocarbons, and for the oxidative dehydrogenation of ethane to form ethylene.

BACKGROUND OF THE INVENTION

Methane is an attractive raw material because it is widely available and inexpensive, but it is used mainly as a fuel. Natural gas liquids (ethane, propane, butane and higher hydrocarbons) are the major raw material for ethylene and propylene, from which many petrochemicals are produced. But the supply of natural gas liquids has not kept pace with increasing demand for olefins, so more costly cracking processes that use naphtha from petroleum are being commercialized. Therefore, the development of economical processes for manufacturing olefins and other hydrocarbons from methane is highly desirable.

Methane has low chemical reactivity, so severe conditions are required to convert it to higher hydrocarbons. Oxidative dehydrogenation is favored because conversion is not thermodynamically limited and reactions are exothermic. But selectively producing ethylene, ethane, and higher hydrocarbons by partial oxidation while avoiding complete oxidation to carbon oxides is difficult to achieve. Accordingly, those skilled in the art have expended much effort in attempts to develop selective catalysts for methane coupling. Rare earth oxycarbonate and oxide catalysts have been of particular interest.

U.S. Pat. No. 4,929,787 discloses a catalyst for oxidative coupling that contains at least one rare earth metal carbonate, which is defined to include simple carbonates and oxycarbonates and which comply approximately with the stoichiometric formulas $M_2(CO_3)_3$, $M_2O_2CO_3$, $M_2O(CO_3)_2$, or $M(OH)(CO_3)$, which may be characterized by elementary analysis, where M is at least one rare earth metal. The rare earth oxycarbonates, $M_2O_2CO_3$, are preferred, with lanthanum oxycarbonate, $La_2O_2CO_3$, being most preferred. Only lanthanum, neodymium, and samarium are used in the examples. The catalysts may be prepared in several ways by thermal decomposition of a rare earth metal compound: carbonates may be directly decomposed; hydroxides, nitrates, carbonates, or carboxylates may be added to a solution of polycarboxylic acid (citric), dried, and roasted under vacuum or in air; carbonates, hydroxides, or oxides may be added to an acid (acetic), dried, and decomposed in air; carbonates or carboxylates (acetates) may be dissolved into aqueous carboxylic acid (formic or acetic), impregnated onto a carrier, and heated in air; or oxides may be contacted with carbon dioxide. These methods all specify decomposing the precursors at a temperature of 300° to 700° C., but the examples all use 525° to 600° C. The decomposition may be done outside or inside the reactor before passing the reacting gas mixture over the catalyst. In one example, the $La_2O_2CO_3$ catalyst was prepared by heating at 120° C. an acetic acid solution containing lanthanum acetate, reducing the volume of the solution by aspiration, drying the material at 150° C. under high vacuum, crushing the resultant foam to fine powder, and roasting the powder in air at 600° C. for two hours. In another example, the reactor was charged with anhydrous lanthanum acetate and treated with helium at 525° C. for one hour to form the $La_2O_2CO_3$ catalyst. The catalyst may also contain one or more alkaline earth metal (Be, Mg, Ca, Sr, Ba) compounds to improve selectivity and a Group IVA metal (Ti, Zr, Hf) to increase activity. The reaction temperature specified is 300° to 950° C., preferably 550° to 900° C.; the examples are mainly at 600° to 750° C., but the catalysts are selective at temperatures exceeding 900° C. as well. The reaction pressure specified is 1 to 100 bars, particularly 1 to 20 bars, but the examples are all at atmospheric pressure. Carbon dioxide may be beneficially added (up to 20%) to the reaction gases as a diluent to increase yield by moderating the bed temperature and as a constituent to maintain a high activity of the carbonate catalyst. These catalysts are utilized in the related processes disclosed in U.S. Pat. Nos. 5,025,108 and 5,113,032.

The effect of reaction pressure on a catalyst disclosed in U.S. Pat. No. 4,929,787 was studied in M. Pinabiau-Carlier, et al., "The Effect of Total Pressure on the Oxidative Coupling of Methane Reaction Under Cofeed Conditions", in A. Holmen, et al., Studies in Surface Science and Catalysis, 61, Natural Gas Conversion, Elsevier Science Publishers (1991). The catalyst (A) was a mechanical mixture of lanthanum oxycarbonate and strontium carbonate that was calcined in air at 600° C. for two hours. Increasing the pressure substantially decreased the selectivity to $C_2+$ hydrocarbons (reaction temperature of 860° C.) from 72% at 1 bar to 39% (constant flow rate) or 35% (increased flow rate for constant conversion) at 7.5 bar (94 psig). Another catalyst (B) was a magnesia support impregnated with aqueous lanthanum and strontium nitrates and then calcined at 800° C. for two hours. This calcination temperature is above the maximum specified calcination temperature of 700° C. disclosed in U.S. Pat. No. 4,929,787 for producing oxycarbonate, and is a temperature at which predominantly lanthanum oxide, $La_2O_3$, is expected to form. The preparation furthermore did not include a carbon source from which oxycarbonate could be formed from the nitrate. Increasing the pressure significantly decreased the $C_2+$ selectivity (900° C.) from 79% at 1.3 bar to 65% at 6 bar (72 psig) with constant flow rate. The study concluded that the reaction should be operated at pressures below 3 bar (29 psig).

A catalyst disclosed in U.S. Pat. No. 4,929,787 was used to study the effect of adding 10% ethane to oxidative coupling and pyrolysis reactors in series in H. Mimoun, et al., "Oxidative Coupling of Methane Followed by Ethane Pyrolysis", Chemistry Letters 1989: 2185. The catalyst was a mechanical mixture of lanthanum oxycarbonate and strontium carbonate. Ethane added to the coupling reactor (880° C. and one atmosphere) decreased methane conversion and increased ethylene and carbon monoxide production. The study concluded that oxygen preferentially dehydrogenates ethane instead of coupling methane; ethane is best separated from the natural gas feed and supplied to just the pyrolysis reactor, where it is cracked with high selectivity to olefins, as disclosed in U.S. Pat. No. 5,025,108.

U.S. Pat. No. 5,061,670 discloses a method for preparing a cocatalyst of lanthanide and alkaline-earth metal carbonates and/or oxycarbonates, which comprises forming an aqueous solution of lanthanide and alkaline-earth metal chlorides; adding alkali metal carbonate and optionally hydroxide to coprecipitate carbonates and/or hydroxycarbonates at a basic pH above 8; separating the coprecipitate from the reaction medium; washing away the alkali metal chlorides formed; and drying and calcining the coprecipitate at 400° to 1000° C. in air or an inert atmosphere. Scandium, yttrium, and lithium may be added as promoters. The examples form cocatalysts of barium with lanthanum or samarium.

Cocatalysts of $BaCO_3$ and $La_2O_2CO_3$ were studied in U. Olsbye, et al., "A Comparative Study of Coprecipitated $BaCO_3/La_2O_n(CO_3)_m$ Catalysts for the Oxidative Coupling of Methane", *Catalysis Today* 13: 603 (1992). They were prepared by mixing aqueous $BaCl_2$ and $LaCl_3$ with NaOH and $Na_2CO_3$ at a pH above 8, washing and drying the precipitate, and calcining it at 500° C. in air. The reaction was done at 750° to 850° C. at atmospheric pressure. The catalysts were small crystals (300–500 Å) of $BaCO_3$ and $La_2O_2CO_3$ (various polymorphs) and some $La_2O_3$ after calcination, and were $BaCO_3$ and $La_2O_3$ after reaction. The tendency of $La_2O_2CO_3$ to convert to $La_2O_3$ was confirmed by thermogravimetric analyses. Surface areas were <16 $m^2/g$ after calcination. The areas decreased during reaction as crystal size grew.

Rare earth oxides have been used as catalysts for methane coupling at atmospheric pressure in many studies. They have been prepared from a variety of rare earth compounds, such as carbonates, hydroxides, nitrates, acetates, and oxalates, by calcination at high temperature in air or another atmosphere, such as nitrogen or helium. The phase composition of these catalysts is known to be highly dependent on the preparation method. Lanthanum oxide in particular is sensitive to exposure to atmospheric water vapor and carbon dioxide, which can convert the oxide over time to a partially carbonated hydroxide. Hydration and carbonation can also occur during catalysis. Commercially prepared oxides are often recalcined as received or after hydrothermal treatment before they are used as catalysts. The surface area of the prepared catalyst generally ranges from 3 to 10 $m^2/g$, with some higher or lower values reported. Surface area decreases with higher calcination temperature and during reaction. The rare earth oxides have been promoted mainly by alkali metal (Li, Na, K, Rb, Cs) and alkaline earth metal (Be, Mg, Ca, Sr, Ba) compounds, mostly in the form of oxides or carbonates. Other promoter compounds have contained elements of Group IIIA (Sc, Y), Group IVA (Ti, Zr, Hf), manganese, Group IB (Cu, Ag, Au), Group IIB (Zn, Cd, Hg), Group IIIB (Al, In), Group IVB (Si, Ge, Sn, Pb), and Group VB (P, Sb, Bi).

U.S. Pat. Nos. 4,499,323; 4,499,324; 4,727,211; 4,727,212; 5,146,027; 5,210,357; 5,567,667; and 5,712,217 disclose the rare earth oxides of lanthanum, cerium, praseodymium, and terbium as catalysts for methane coupling. However, several literature studies report that deleterious effects result from the use of rare earth oxides for the oxidative coupling reaction of methane under elevated pressure.

A. Ekstrom, et al., "Effect of Pressure on the Oxidative Coupling Reaction of Methane", *Applied Catalysis* 62: 253 (1990), studied the effect of pressure on oxidative coupling by $Sm_2O_3$ and $SrCO_3/Sm_2O_3$. Increasing the pressure to 87 psi significantly increased the importance of the uncatalyzed combustion reaction. This could be reduced by using high linear velocities, but increasing the pressure under these conditions still depressed the $C_2+$ selectivity and the catalyst activity.

D. E. Walsh, et al., "Direct Oxidative Methane Conversion at Elevated Pressure and Moderate Temperatures", *Industrial and Engineering Chemistry Research* 31: 1259 (1992), studied the effect of high pressure on oxidative coupling by $Sm_2O_3$. The $C_2+$ selectivity declined from 55–60% at atmospheric pressure (800–850° C.) to 36% at 900 psi (550° C.). However, at 900 psi, the non-catalyzed reaction gave 32% selectivity, with the gain being in ethane rather than ethylene. Therefore at high pressure the catalyst had little effect on the coupling reaction. Similarly, D. E. Walsh, et al., "Pressure, Temperature, and Product Yield Relationships in Direct Oxidative Methane Conversion at Elevated Pressures and Moderate Temperatures", *Industrial and Engineering Chemistry Research* 31: 2422 (1992), obtained only 13% $C_2+$ selectivity for oxidative coupling at 450 psi (630° C.) by using $Sm_2O_3$, with little ethylene produced (2.5%).

Clearly, there is a need for improved catalysts for the oxidative dehydrogenation of hydrocarbons and, in particular, for producing ethylene, ethane, and higher hydrocarbons from methane by oxidative dehydrogenation coupling. Such catalysts would provide high selectivity for oxidative dehydrogenation reactions and would enable these reactions to be carried out at elevated pressure instead of at atmospheric pressure. Improved catalysts would also have high activity at low temperature, operate at economical conversion levels, and remain stable during long-term operation. These catalysts must also be suitable for large-scale commercial production.

SUMMARY OF THE INVENTION

The present invention meets the above-noted objects by providing, in one aspect, catalysts which are highly selective for the oxidative dehydrogenation of lower hydrocarbons to produce higher hydrocarbons and/or lower olefins. The invention further provides methods for preparing such catalysts and processes for using the catalyst in the oxidative dehydrogenation of lower hydrocarbons. As used herein, the term "lower hydrocarbon" includes lower alkanes (typically $C_1-C_4$ alkanes), alkyl aromatics (typically aromatics having $C_1-C_4$ alkyl appendages), and cyclic compounds. The term "higher hydrocarbon" means a hydrocarbon having a greater number of carbon atoms than the lower hydrocarbon which undergoes oxidative dehydrogenation (e.g., the coupling of methane to form ethane, ethylene and other higher hydrocarbons). The term "lower olefin" refers to an olefin having the same number of carbon atoms as the lower hydrocarbon which undergoes oxidative dehydrogenation (e.g., the oxidative dehydrogenation of ethane to form ethylene).

In one embodiment, the catalyst taught by the invention comprises a nonstoichiometric rare earth oxycarbonate of the formula $M_XC_YO_Z$ having a disordered and/or defect structure, wherein M is at least one rare earth element selected from the group consisting of La, Pr, Nd, Sm, Eu, Gd, Tb, Dy, Ho, Er, and Tm; X=2, Z=3 +AY; A is less than about 1.8, and Y is the number of carbon atoms in the oxycarbonate. When used for the oxidative dehydrogenation of a lower hydrocarbon at a pressure above about 100 psig, the catalyst has a selectivity of at least about 40% to at least one higher hydrocarbon and/or lower olefin. The catalyst may further comprise a cocatalyst containing at least one metal selected from the group consisting of V, Nb, Ta, Cr, Mo, W, Mn, Re, Fe, Co, Ni, Cu, Zn, Sn, Pb, Sb, and Bi. The cocatalyst may also include at least one alkali metal or alkaline earth metal.

In another embodiment, a catalyst according to the invention comprises an oxycarbonate, hydroxycarbonate, and/or carbonate of at least one rare earth element selected from the group consisting of La, Pr, Nd, Sm, Eu, Gd, Tb, Dy, Ho, Er, and Tm. When used for the oxidative dehydrogenation of a lower hydrocarbon, the catalyst exhibits higher selectivity to at least one higher hydrocarbon and/or lower olefin at a pressure above about 100 psig than the catalyst or a precursor of the catalyst exhibits at a pressure in the range of about atmospheric pressure to about 25 psig. When operating at a pressure above about 100 psig, the catalyst has a selectivity of at least about 40%.

In still another embodiment, the catalyst taught by the invention comprises: (1) an oxycarbonate, hydroxycarbonate and/or carbonate of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Mn, Re, Fe, Co, Ni, Cu, Zn, Sn, Pb, Sb, and Bi. When used for the oxidative dehydrogenation of a lower hydrocarbon the catalyst has a selectivity of at least about 40% to at least one higher hydrocarbon and/or lower olefin.

In yet another embodiment, the catalyst of the invention comprises: (1) an oxide of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Re, Fe, Co, and Ni. The catalyst, when used for the oxidative dehydrogenation of said lower hydrocarbon, has a selectivity of at least about 40% to at least one higher hydrocarbon and/or lower olefin.

As previously noted, the invention is also directed to methods for preparing catalysts selective for the oxidative dehydrogenation of lower hydrocarbons and to processes for using these catalysts. These methods and processes will be disclosed in detail below in connection with the detailed discussion of the various embodiments of the catalysts taught by the invention.

DETAILED DESCRIPTION OF THE INVENTION

Figure 1:
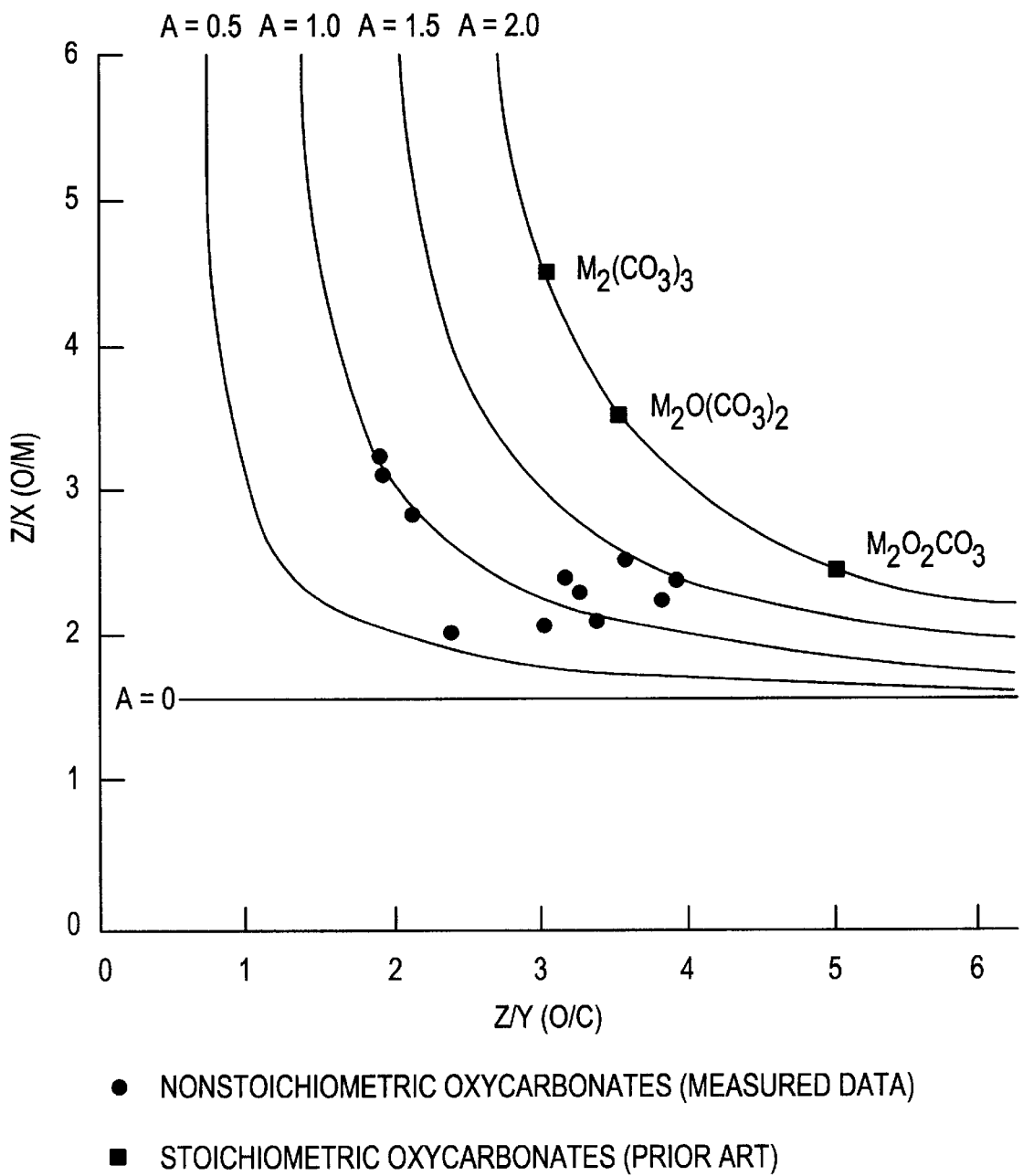
FIG. 1 is a plot of the elemental mole ratios of the catalyst Z/X (O/M) versus Z/Y (O/C), which compares measured ratios of nonstoichiometric oxycarbonate compositions of the present invention (parameter A less than about 1.8) with stoichiometric oxycarbonates (or mixtures thereof) of the prior art (A=2.0).

The catalysts and processes of the present invention are used for the oxidative dehydrogenation of a lower hydrocarbon to form at least one higher hydrocarbon and/or lower olefin. They are particularly suitable for the oxidative dehydrogenation coupling of methane to form ethylene, ethane, and higher hydrocarbons such as propylene, propane, and other higher alkanes and olefins, which are produced in progressively lesser amounts as the carbon number increases. Ethylene and ethane are therefore the main products from methane coupling, but significant amounts of propylene and propane can also be produced. Other hydrocarbons may also be used as the feedstock, such as ethane to produce butylene and butane, or propane to produce hexene and hexane, or a mixture of hydrocarbons may be used, such as natural gas (typically a mixture of 90+% methane, and the balance being ethane, propane and butane), or a mixture of ethane and propane.

In the case where the higher hydrocarbon is an olefin, i.e., an olefin having a higher number of carbon atoms than the lower hydrocarbon undergoing oxidative dehydrogenation, it should be understood that the olefin can be formed directly from the lower hydrocarbon or in a secondary oxidative dehydrogenation reaction. For example, where the lower hydrocarbon is methane, ethylene can be formed directly from methane via oxidative dehydrogenation. Alternatively, ethane is formed first in a coupling reaction, and then the ethane undergoes a secondary oxidative dehydrogenation reaction to form ethylene.

As noted above, the catalysts of the present invention are also useful for the oxidative dehydrogenation of a lower hydrocarbon to form a lower olefin, i.e., an olefin having the same number of carbon atoms as the lower hydrocarbon. Accordingly, the catalysts of the invention have particular utility for forming ethylene from ethane and propylene from propane. This is particularly advantageous because, in general, olefins such as ethylene and propylene are the most desired products. Thus, byproduct alkanes such as ethane and propane can be recycled and converted to the desired olefins.

The oxidative dehydrogenation of a lower hydrocarbon is carried out by contacting the hydrocarbon with a source of oxygen, either directly or indirectly, under reaction conditions in the presence of a catalyst of the present invention. When methane is coupled by oxidative dehydrogenation, ethylene, propylene, and water are produced according to the following net reactions.

$2CH_4+O_2 \rightarrow C_2H_4+2H_2O$ $3CH_4+3/2O_2 \rightarrow C_3H_6+3H_2O$

Ethane and propane and water are produced according to the following net reactions.

$2CH_4+1/2O_2 \rightarrow C_2H_6+H_2O$ $3CH_4+O_2 \rightarrow C_3H_8+2H_2O$

The methane and higher hydrocarbons can also undergo combustion to produce carbon monoxide, carbon dioxide, and water.

In addition, secondary oxidative dehydrogenation reactions may occur such as the following:

$C_2H_6+1/2O_2 \rightarrow C_2H_4+H_2O$ $C_3H_8+1/2O_2 \rightarrow C_3H_6+H_2O$ $CH_4+C_2H_6+1/2O_2 \rightarrow C_3H_8+H_2O$ The hydrocarbon feedstock may be obtained from any suitable source. The hydrocarbon may be pure or present in a mixture, such as with other hydrocarbons, inert gases such as nitrogen and argon, and/or other components, such as water. Undesirable impurities, such as poisons for the catalyst, preferably are at low levels that permit economical operation of the oxidative dehydrogenation reaction. Undesirable impurities include hydrogen sulfide and other sulfur compounds, mercury, phosphorous and acetylenes. Inert gases should not be at excessive levels. Hydrogen and carbon monoxide are preferably present at low levels because they consume the reactant oxygen to undesirable $H_2O$ and $CO_2$. Although carbon dioxide may be present, it is preferably at a low level below about 5% by volume, more preferably below about 2%, because carbon dioxide decreases reaction selectivity with some of the catalysts of the present invention. When the hydrocarbon is methane, the methane may be obtained from any suitable source, such as natural gas, refinery gas, and synthetic natural gas, preferably with methane being the primary component. Processed natural gas is preferred because impurities are at acceptably low levels. The processed natural gas may be used without removing ethane, propane, and higher hydrocarbons.

The necessary oxygen may be obtained from any suitable source, including without limitation, oxygen, ozone, and oxides of nitrogen. Preferably, oxygen is used to carry out the reaction. The $O_2$ may be fed at any concentration by mixing with $N_2$, He, or other inert gases. A convenient and safe source of oxygen is air. High purity oxygen from an oxygen plant or oxygen-enriched air may also be used as the source of this reactant.

First Catalyst Embodiment

One embodiment of the catalyst taught by the invention comprises a nonstoichiometric rare earth oxycarbonate of the formula $M_XC_YO_Z$ having a disordered and/or defect structure, wherein M is at least one rare earth element selected from the group consisting of La, Pr, Nd, Sm, Eu, Gd, Tb, Dy, Ho, Er, and Tm; X=2; Z=3+AY; A is less than about 1.8, and Y is the number of carbon atoms in the oxycarbonate. When used for the oxidative dehydrogenation of a lower hydrocarbon at a pressure above about 100 psig, the catalyst has a selectivity of at least about 40% to at least one higher hydrocarbon and/or lower olefin.

The nonstoichiometric rare earth oxycarbonate catalyst of the formula $M_XC_YO_Z$, wherein X=2, C is carbon, and O is oxygen, can be formed conceptually from the corresponding rare earth oxide, $M_2O_3$, according to the following equation.

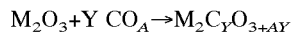

The parameter value of A=2 generates all of the stoichiometric rare earth oxycarbonate compounds, mixtures, and intermediates of the prior art as the parameter Y increases from zero, according to the following equation.

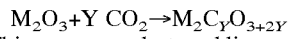

This corresponds to adding carbon dioxide in increasing amounts to the rare earth oxide. This is a standard method of preparing the stoichiometric rare earth oxycarbonate compounds, as well as mixtures of the stoichiometric oxycarbonates with each other and the oxide, as is known to one skilled in the art. The parameter value of Y=1 generates the rare earth dioxymonocarbonate, $M_2O_2CO_3$; Y=2 generates the monooxydicarbonate, $M_2O(CO_3)_2$; and Y=3 generates the carbonate, $M_2(CO_3)_3$, all of which, as used herein, are considered to be stoichiometric rare earth oxycarbonates, according to the following equations.

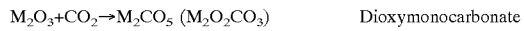 Dioxymonocarbonate

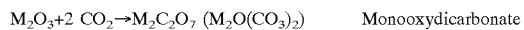 Monooxydicarbonate

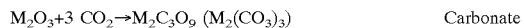 Carbonate

Noninteger values of Y<3 correspond to mixtures of the oxycarbonates with each other or with the oxide. For example, Y=0.5 is an equimolar mixture of dioxymonocarbonate and oxide, Y=1.5 is an equimolar mixture of dioxymonocarbonate and monooxydicarbonate, and Y=2.5 is an equimolar mixture of monooxydicarbonate and carbonate. Other mixtures are also possible. Values of Y>3 correspond to carbonate containing excess carbon dioxide.

In contrast, the rare earth oxycarbonate catalysts of the present invention are nonstoichiometric compounds having the parameter A less than about 1.8. The parameter value of A=1 corresponds to nonstoichiometric oxycarbonates being formed conceptually by the addition of carbon monoxide to the rare earth oxide, according to the following equation.

$$M_2O_3 + Y\ CO \rightarrow M_2C_YO_{3+Y}$$

Similarly, the parameter value of A=0 corresponds to adding carbon to the oxide, according to the following equation.

$$M_2O_3 + Y\ C \rightarrow M_2C_YO_3$$

Increasing values of the parameter Y correspond to adding increasing amounts of carbon monoxide or carbon to the oxide. Noninteger values of 0<A<1.8 correspond to adding a mixture of carbon monoxide, carbon dioxide, and/or carbon to the oxide. For example, A=1.5 corresponds to adding an equimolar mixture of carbon monoxide and carbon dioxide to the oxide, whereas A=0.5 corresponds to adding an equimolar mixture of carbon monoxide and carbon to the oxide. Other mixtures are also possible.

The parameter A for a given nonstoichiometric oxycarbonate can be readily calculated from measured values of the elemental ratios O/M and O/C for the material according to the following equation.

$$A = [(O/M) - 1.5]\ (O/C)/(O/M)$$

Examples of measured compositions of nonstoichiometric oxycarbonate catalysts of the present invention (parameter A<1.8) are given in FIG. 1 as a plot of the elemental mole ratios Z/X (O/M) versus Z/Y (O/C). The compositions are for the rare earths lanthanum and gadolinium and were prepared by the methods of the present invention. They include catalysts both as prepared and after reaction, and also without and with a cocatalyst. The overall average parameter value is A=1.08, so on average the nonstoichiometric oxycarbonate compositions correspond approximately to adding carbon monoxide in different amounts to the rare earth oxide. The compositions of the present invention are also compared with the stoichiometric oxycarbonates, or mixtures thereof, of the prior art (curve with A=2.0), which in contrast correspond to adding carbon dioxide in different amounts to the rare earth oxide. Therefore the nonstoichiometric compositions are richer in carbon and deficient in oxygen compared to the stoichiometric oxycarbonates. FIG. 1 also shows curves corresponding to parameter A values of 1.5, 1.0, 0.5, and 0. The curves approach the composition of the rare earth oxide in the limit of very large ratio of Z/Y, as the parameter Y goes to zero. In the opposite limit, as the parameter Y becomes very large, the curves asymptotically approach Z/Y=A.

The nonstoichiometric oxycarbonate catalysts of the present invention preferably have a parameter A value less than about 1.7, more preferably less than about 1.6, still more preferably less than about 1.5, and most preferably less than about 1.3. The parameter A value preferably is greater than about 0.2, more preferably greater than about 0.4, still more preferably greater than about 0.5, and most preferably greater than about 0.7.

The parameter Y is preferably in the range of about 0.5 to about 10, more preferably in the range of about 0.6 to about 8, still more preferably in the range of about 0.8 to about 6, and most preferably in the range of about 1 to about 4.

Preferably the ratio Z/X is in the range of about 1.5 to about 4.5 and the ratio Z/Y is in the range of about 1.0 to about 6.0. When the parameter A is in the range of about 0.4 to about 1.6, preferably the ratio Z/X is less than about 3.75 and the ratio Z/Y is in the range of about 1.5 to about 4.5. When the parameter A is in the range of about 0.5 to about 1.5, preferably the ratio Z/X is less than about 3.5 and the ratio Z/Y is in the range of about 1.75 to about 4.25.

The elemental mole ratios Z/X (O/M) and Z/Y (O/C) of the catalyst may be measured by using electron energy loss spectroscopy (EELS) on a scanning transmission electron microscope, which is known to one skilled in the art. This technique was used to determine measured values in FIG. 1 by crushing the catalyst sample and collecting between 10 and 50 individual spectra from each sample in order to obtain a representative average sampling of the material. The individual spectra measurements exhibit variation in the elemental ratios that is reflective of variation in the nonstoichiometric composition within the catalyst material. As used herein, the elemental mole ratios Z/X and Z/Y, and therefore values of parameter A, are understood to mean values that are representative of the catalyst material. The elemental mole ratios may also be determined by using wave-length dispersion x-ray fluorescence, x-ray photoelectron spectroscopy, or other methods known to those skilled in the art.

As used herein, it is understood that the nonstoichiometric oxycarbonate catalysts of the present invention, in addition to the at least one rare earth element, carbon, and oxygen, may also contain hydrogen as a secondary component, including but not limited to such forms as hydroxyl or hydroxide groups, —$CH_x$ groups, and hydrides. Hydrogen may become incorporated into the catalyst from water during preparation, from oxidative reaction of the hydrocarbon, or as a remnant of starting materials. The catalyst may also contain halogen as a secondary component, especially as a consequence of optionally feeding trace quantities of halocarbons to enhance olefin formation. The catalyst may also contain impurities present in starting materials.

The nonstoichiometric rare earth oxycarbonate catalysts of the present invention have a disordered and/or defect structure. All materials of commercial interest, with exceptions such as diamonds and semiconductors, are disordered at some level. One limit is perfect single crystals that contain no structural or chemical defects, disruptions, or randomness and therefore are considered to be perfectly ordered. The other limit is a perfectly random structure, such as a glass, that is completely amorphous. In between these limits lies the region that at some level is disordered. The degree of disorder is related to the structure and chemistry of the material and the frequency with which disruptions and randomness occur in the perfect structure and chemistry. Long range order is typically ascribed to structures that lack disruptions and randomness for several hundreds or thousands of angstroms. Short range order typically refers to lacking disruptions and randomness for tens of angstroms. As used herein, the term "disordered structure" is understood to mean the absence of long range order in regions of the catalyst material.

The frequency of the disruptions and randomness can vary from one location to another in the catalyst material, such that one location can have very few disruptions and have long range order and another location can have a high frequency of disruptions and randomness and be limited to short range order. A high frequency of disruptions and randomness can create a very disordered region with locations that have no order and are amorphous.

As used herein, the term "defect structure" is understood to mean the presence of defects within regions of the catalyst material. The defects may be structural defects and/or chemical defects and include, but are not limited to, the following types of defects, which are known to those skilled in the art: grain boundaries, stacking faults, twin boundaries, inversion boundaries, crystallographic shear planes, antiphase phase boundaries, point defects (vacancies/interstitials), dislocations, shear planes, and polytypoids. Defects that cause disruption in the crystal structure can be readily observed in high resolution transmission electron micrographs. These are often, but not always, associated with changes in the local chemistry around the fault region.

Point defects such as vacancies and interstitials are defects that cause nonstoichiometry; this form of chemical disorder cannot be readily distinguished visibly in micrographs. However, in structural terms, these disordered nonstoichiometric regions may appear to have long range order, because the vacancies do not necessarily disrupt the crystal structure. Electron diffraction can suggest the presence of nonstoichiometry and local chemical disorder, but only through quantitative chemical analysis can the nonstoichiometry be confirmed. Therefore, a full analysis of disorder of a material is based upon the chemical fluctuations within the material, which can be measured spectroscopically, and the frequency of disruption in the crystal structure, which can be observed visually in the high resolution transmission electron microscope. The extent of disorder is a subjective measure based on the frequency of structural disruptions and the chemical fluctuations.

Figure 2:
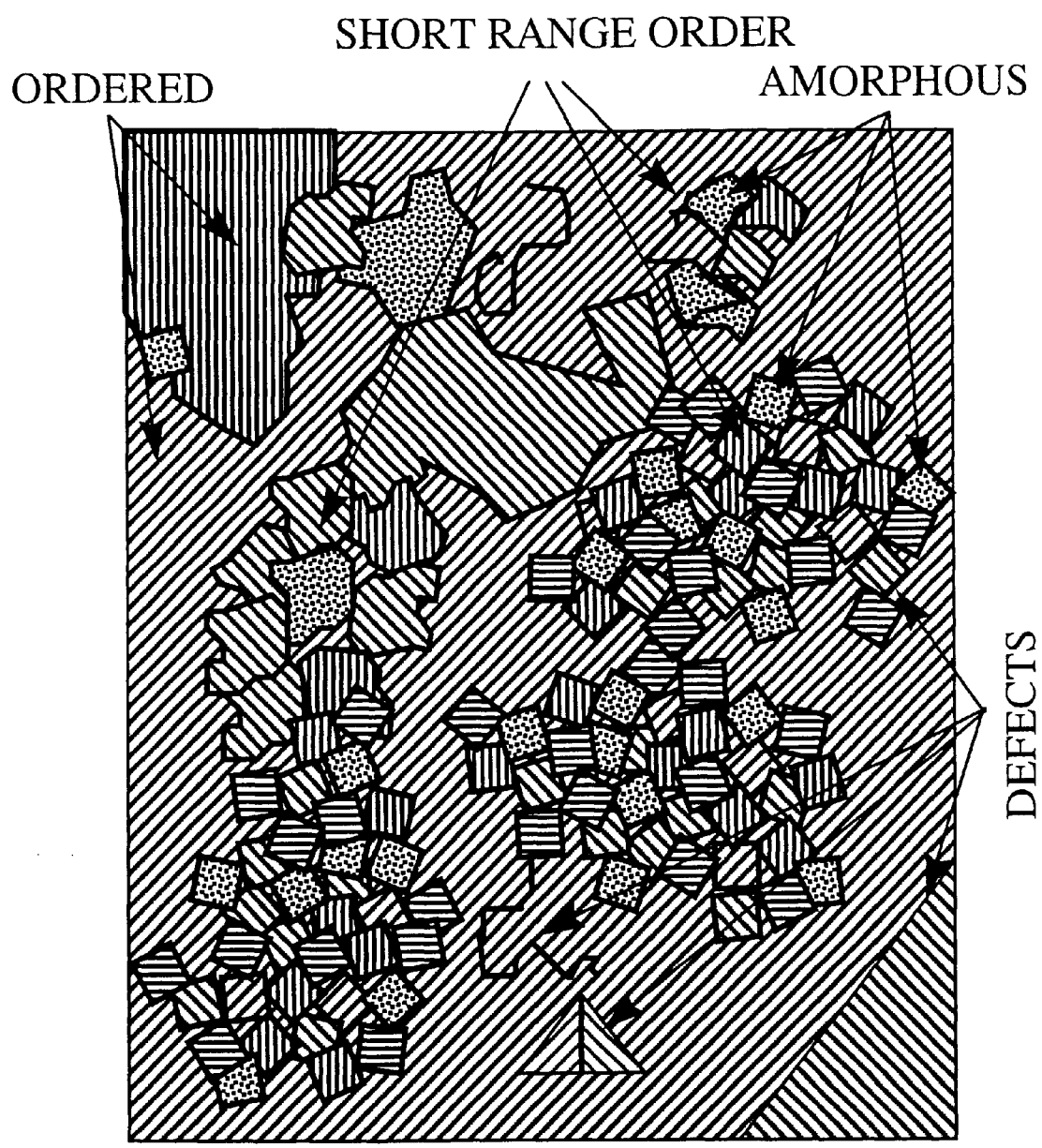
FIG. 2 is a schematic diagram illustrating order, disorder and defects, as well as crystalline vs. amorphous composition in a catalyst structure.
Figure 3:
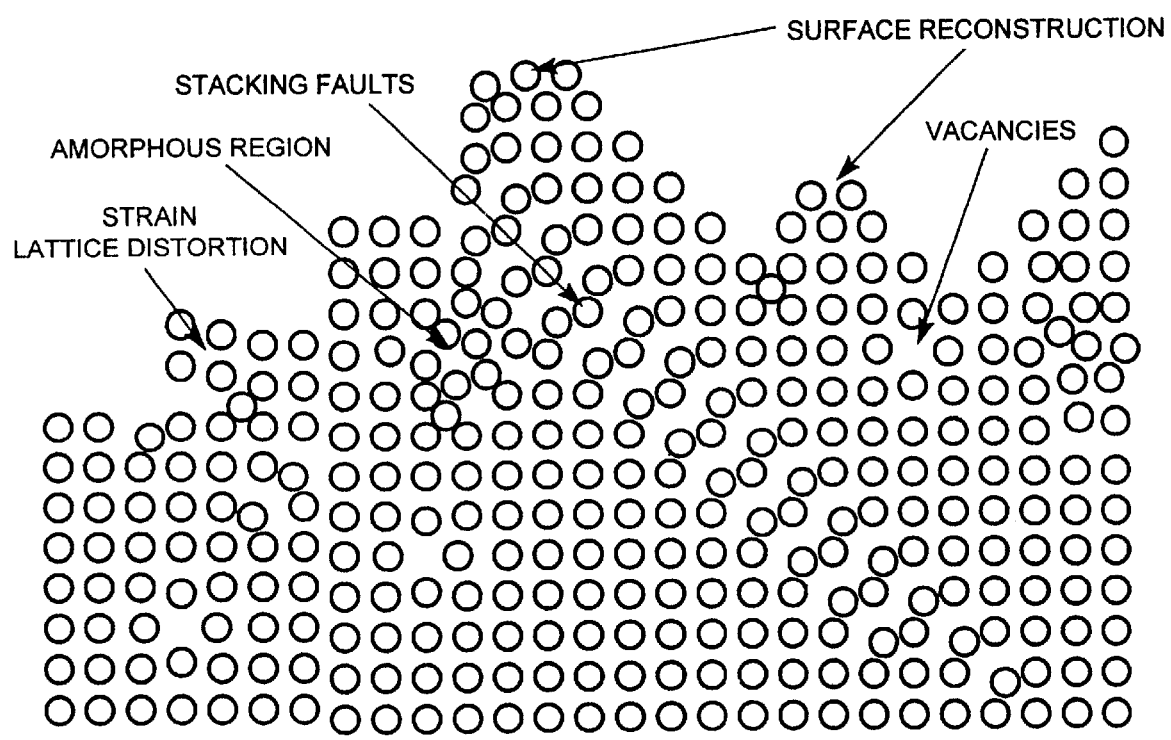
FIG. 3 is a schematic diagram illustrating disorder and defects at a catalyst surface.

Disorder and defects in a catalyst structure as viewed in a high resolution electron microscope are illustrated in the schematic diagram of FIG. 2. The series of parallel hatched lines represent the atomic planes of the crystal structure as viewed under a given crystallographic projection. The types of order in the material cover the spectrum from completely disordered (amorphous) regions to highly ordered (long range order) regions. The disordered regions frequently are present as an assemblage of nanocrystalline domains of various orientation, size, and degree of order. The diagram also illustrates several examples of structural defects: twin boundaries, stacking faults, grain boundaries, and dislocations. Disorder and defects at a catalyst surface are illustrated in the schematic diagram of FIG. 3. The circles represent the atom columns. Amorphous regions, faults, and strain which result in lattice distortions and surface reconstruction are indicated as they may appear in a high resolution electron microscope image. Surfaces of the type illustrated do not possess long range order and exhibit disordered structure. Vacancies are indicated but they would not be readily apparent in the image unless a large vacancy cluster were present or an entire column of atoms were missing.

Figure 4:
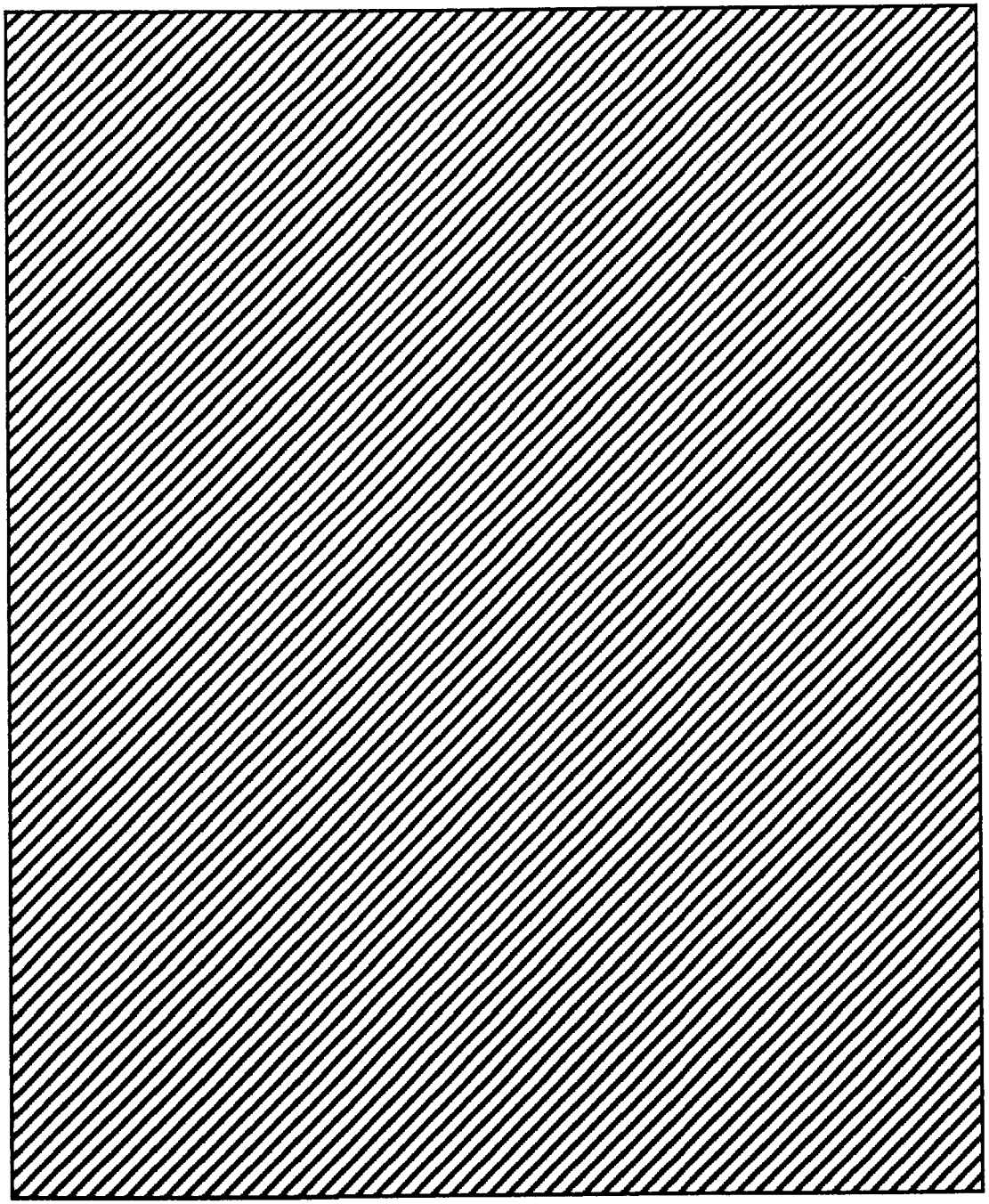
FIG. 4 is a schematic diagram illustrating long range order in a catalyst structure which is not in accordance with the present invention for catalysts that do not exhibit such long-range order.
Figure 5:
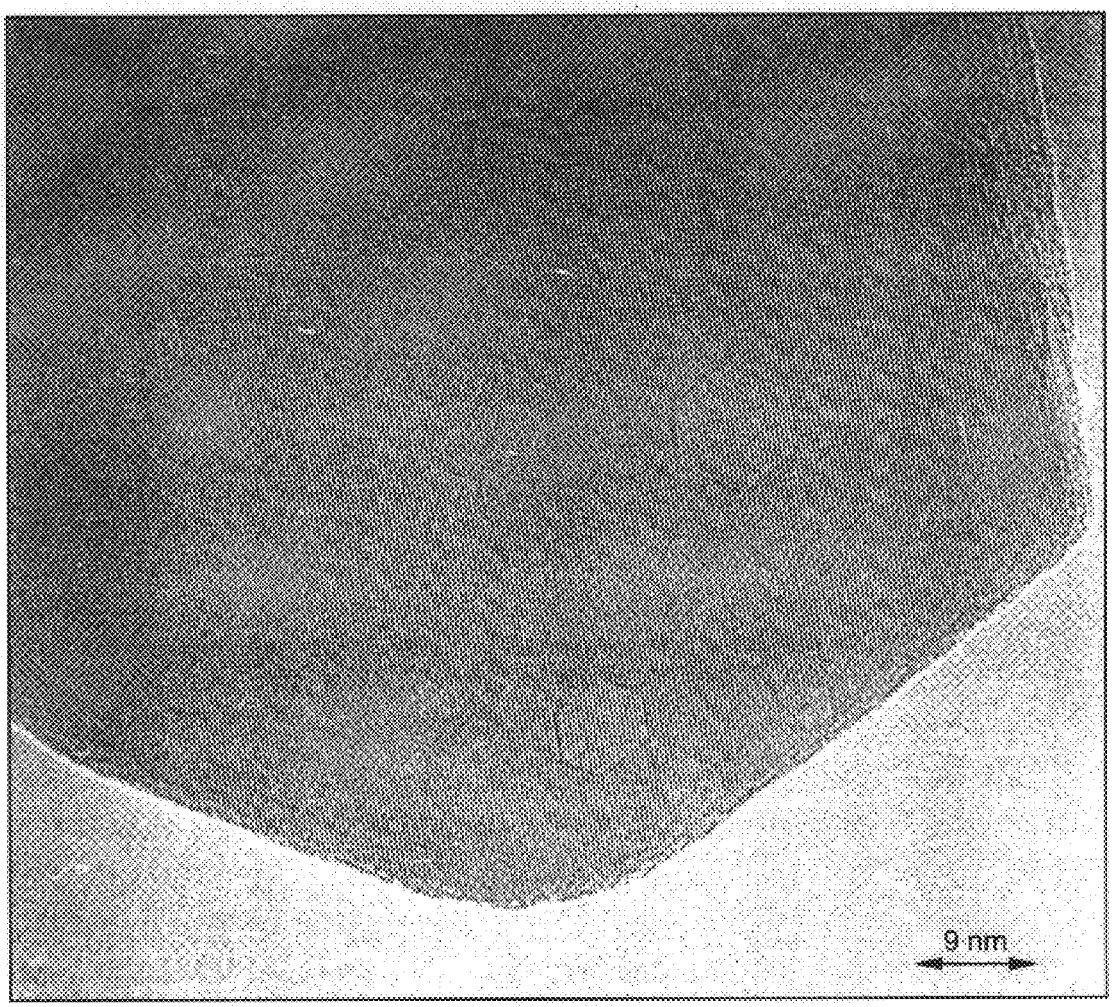
FIG. 5 is a high resolution electron microscope micrograph of lanthanum oxide illustrating completely long range order, which is not in accordance with an embodiment of the present invention.

In contrast, long range order in a catalyst structure which is not in accordance with the present invention as viewed in a high resolution electron microscope is illustrated in the schematic diagram of FIG. 4. The series of parallel hatched lines represent the atomic planes of the crystal structure as viewed under a given crystallographic projection. Such completely long range order is readily apparent in the high resolution electron microscope micrograph of lanthanum oxide in FIG. 5 as indicated by the highly periodic features of the image.

In the compositions of the present invention, preferably at least about 5%, more preferably at least about 10%, still more preferably at least about 20%, and most preferably at least about 30% of the nonstoichiometric rare earth oxycarbonate catalyst has a disordered and/or defect structure, as shown by high resolution electron microscopy. The disordered structure of the catalyst preferably has short range order that is mainly limited to being less than about 300 angstroms, more preferably less than about 200 angstroms, and most preferably less than about 100 angstroms. The defect structure of the catalyst preferably has a high spatial frequency of defects wherein the defects mainly occur more frequently than about one defect per 300 angstroms, more preferably about one defect per 200 angstroms, and most preferably about one defect per 100 angstroms, as shown by high resolution electron microscopy.

Unlike catalysts in the prior art, the catalysts of the present invention exhibit high selectivity for the oxidative dehydrogenation of lower hydrocarbons at elevated pressure. When used for the oxidative dehydrogenation of a lower hydrocarbon, the catalyst should have a selectivity to at least one higher hydrocarbon and/or lower olefin of at least about 40%, preferably at least about 45%, more preferably at least about 50%, still more preferably at least about 55%, and most preferably at least about 60% when at a pressure above about 100 psig. Without wishing to be bound by theory, elevated pressure is believed to have a beneficial effect on the catalyst. The elevated pressure significantly increases the concentration of reaction intermediate species, which is believed to stabilize the nonstoichiometric composition and the disordered and/or defect structure. Elevated pressure also increases catalyst activity and selectivity at lower temperature and increases heat transfer from active catalyst sites, which prevents the structure from becoming too hot and decomposing. In contrast, at low pressure, activity is much lower, so it is necessary to use excessively high temperature, which destroys the selective catalyst composition.

Unlike catalysts in the prior art, which can be utilized at the elevated temperatures that are necessary to obtain high activity at low pressure, which are generally in the range of 600° to 900° C., the nonstoichiometric rare earth oxycarbonate catalysts of the present invention have the property that the catalyst becomes unselective for the oxidative dehydrogenation reaction at elevated temperature, which generally occurs in the range of about 600° C. to about 750° C., and frequently occurs in the range of about 650° C. to about 700° C. As used herein, the term "unselective" is understood to mean that the selectivity of the oxidative dehydrogenation reaction is below about 20% or decreases substantially.

Figure 6:
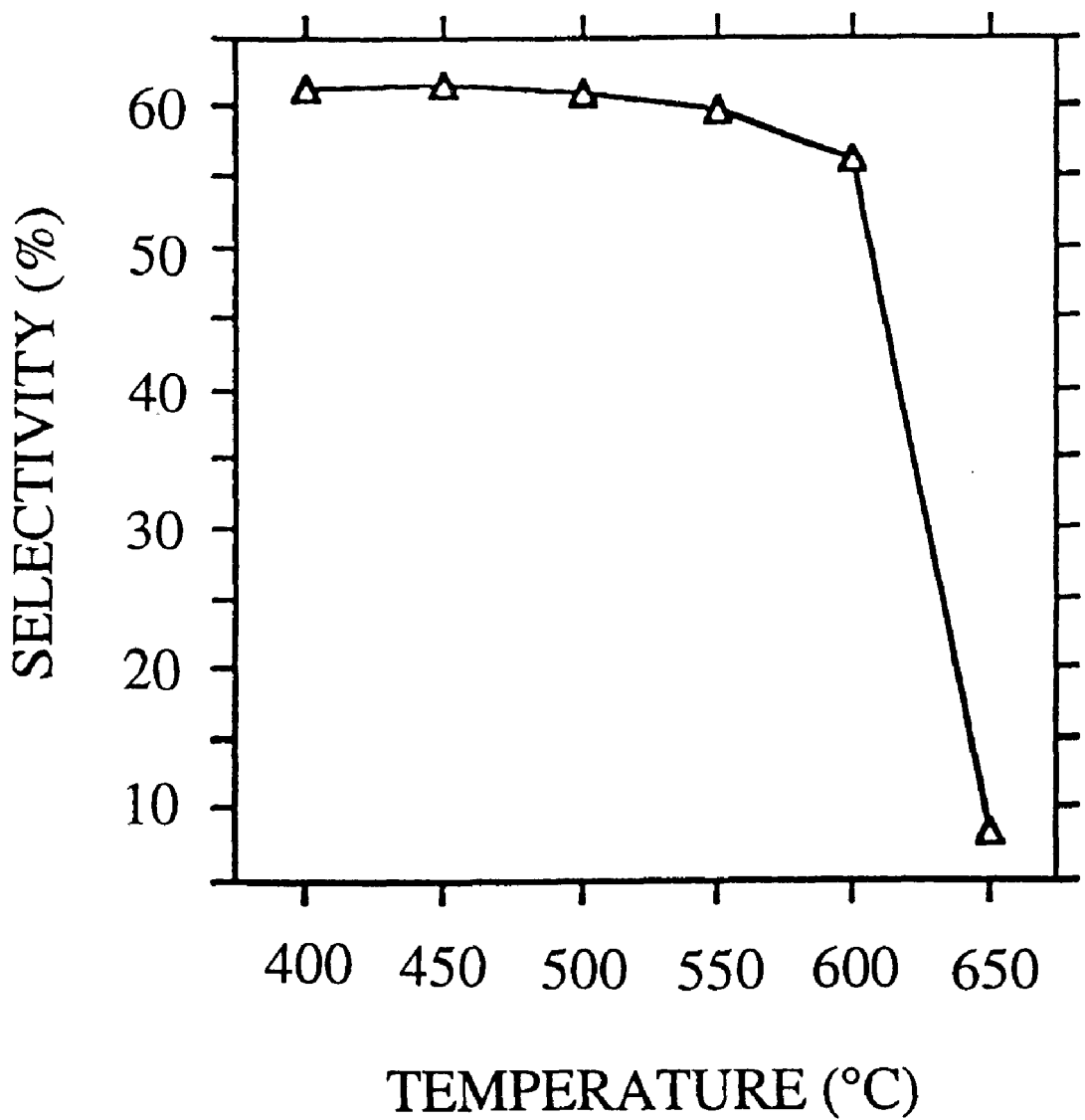
FIG. 6 is a plot of $C_2$ selectivity versus reaction temperature for the oxidative coupling of methane with a nonstoichiometric lanthanum oxycarbonate catalyst at a pressure of 125 psig.
Figure 7:
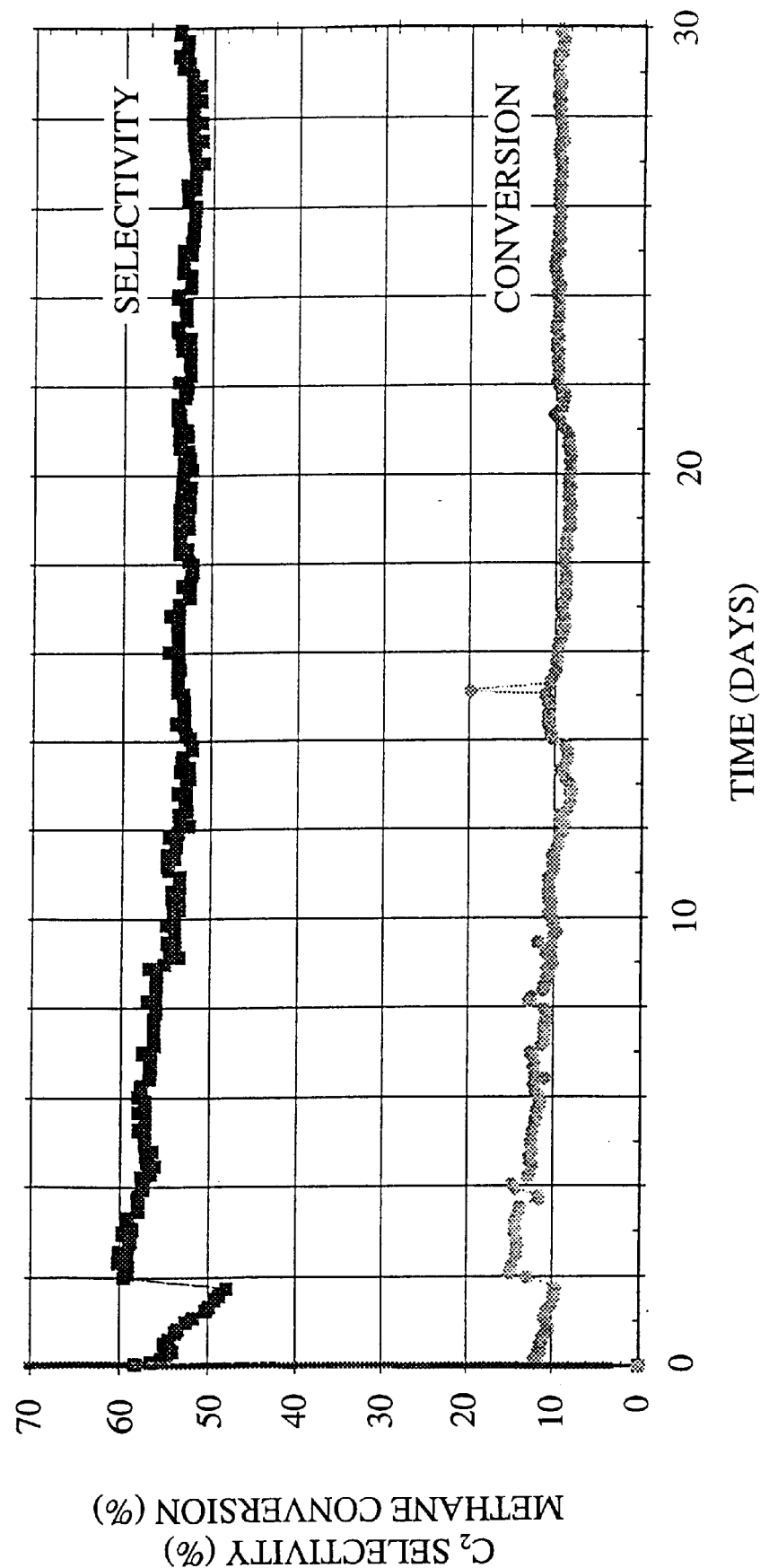
FIG. 7 is a plot of $C_2$ selectivity and methane conversion versus time for long-term oxidative coupling of methane by a lanthanum oxycarbonate catalyst having manganese, tantalum, and antimony cocatalysts at a temperature of 575–600° C. and pressure of 125 psig.
Figure 8:
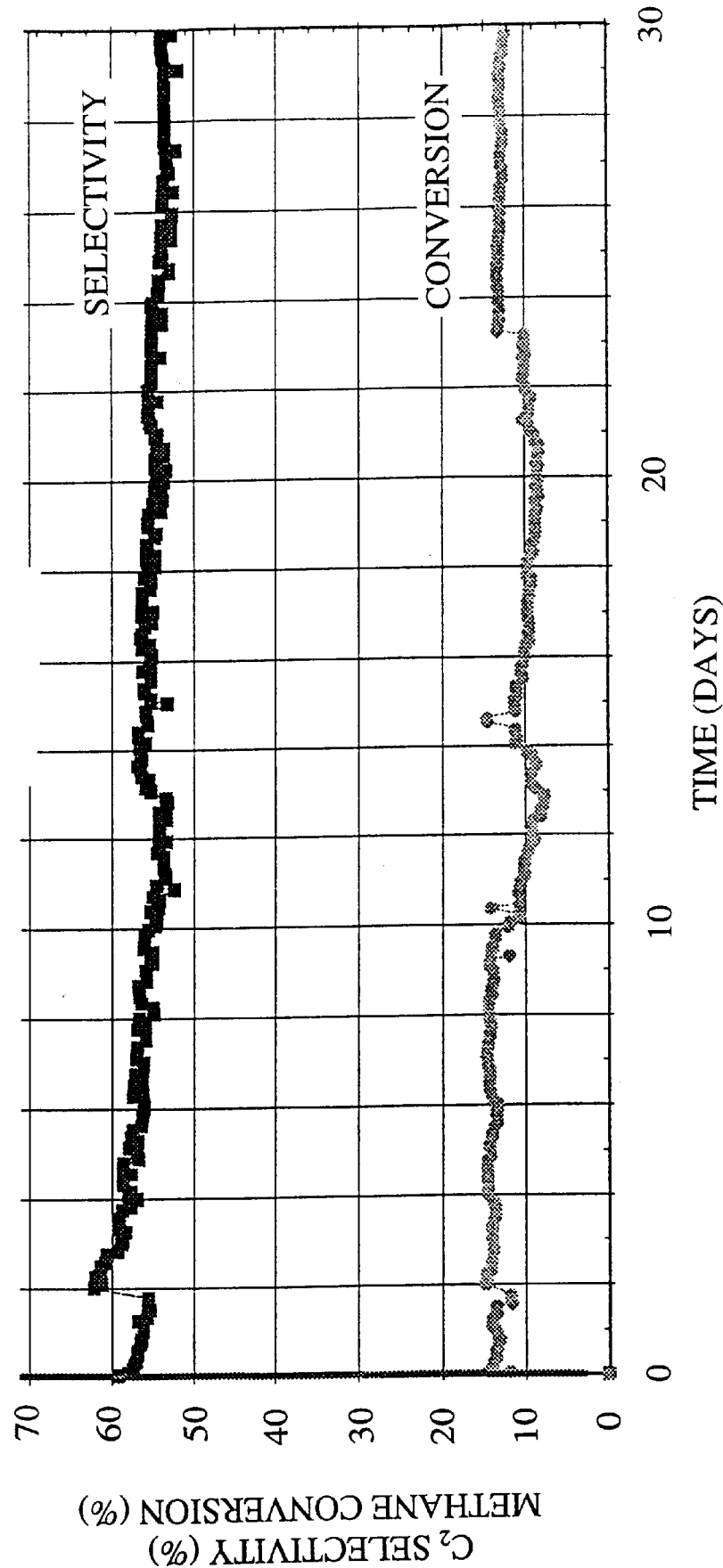
FIG. 8 is a plot of $C_2$ selectivity and methane conversion versus time for long-term oxidative coupling of methane by a lanthanum oxycarbonate catalyst having iron and $Na_2CO_3$ cocatalysts with acetic acid treatment, at a temperature of 575–600° C. and pressure of 125 psig.
Figure 9:
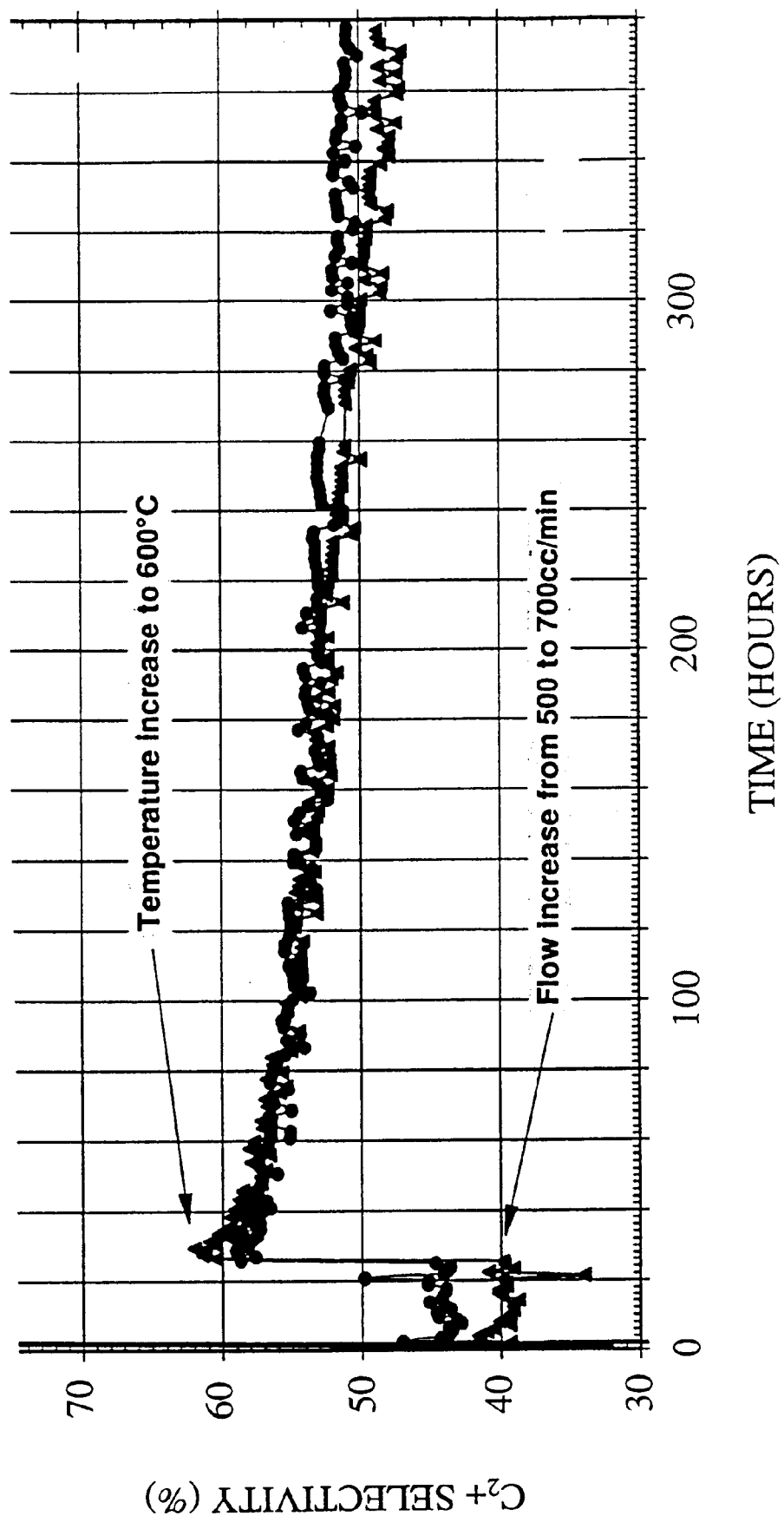
FIG. 9 is a plot of $C_2+$ selectivity versus time for long-term oxidative coupling of methane by a lanthanum oxycarbonate catalyst having manganese and tungsten cocatalysts and supported by $\alpha$-$Al_2O_3$ either with binder (circles) or without binder (triangles) at a temperature of 550–600° C. and pressure of 125 psig.
Figure 10:
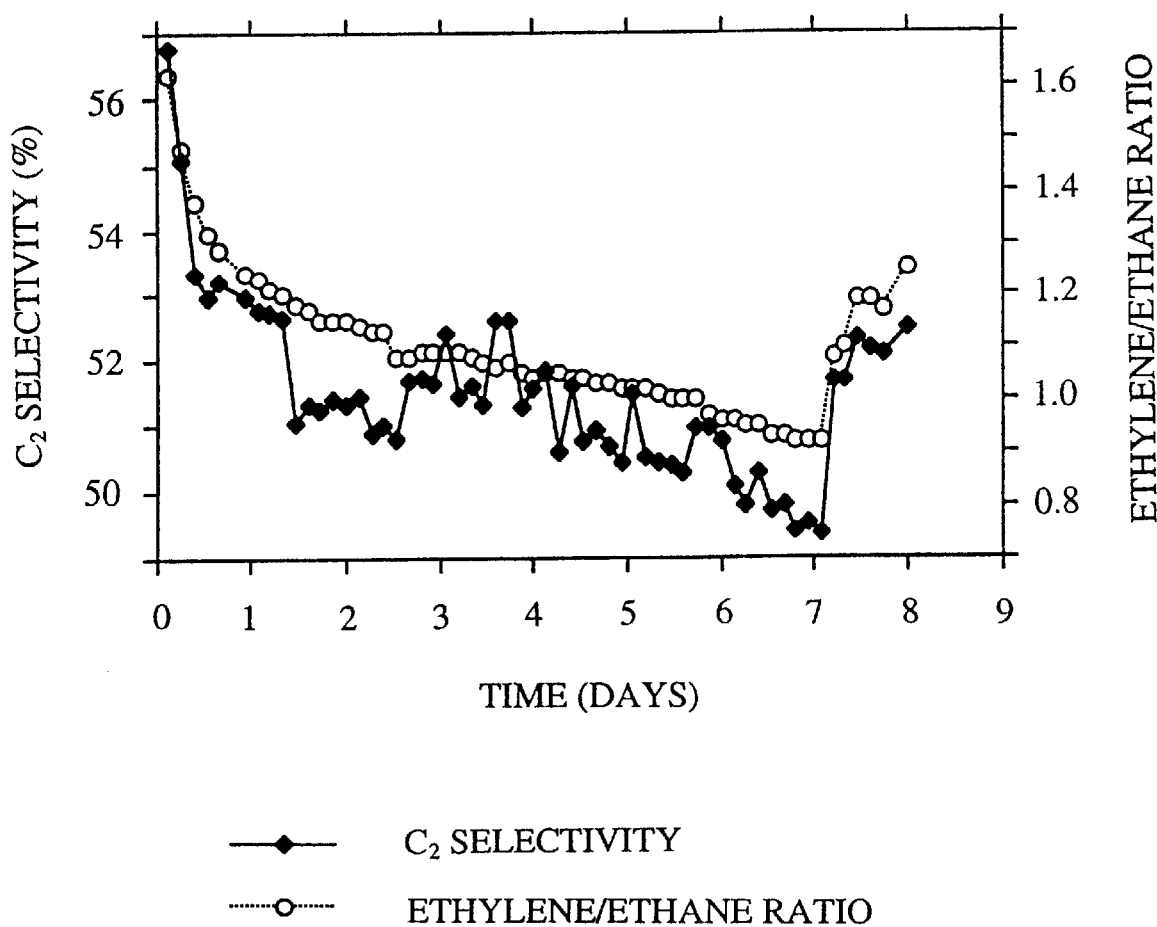
FIG. 10 is a plot of $C_2$ selectivity and ethylene/ethane ratio versus time for long-term oxidative coupling of methane by a sodium chloride-promoted lanthanum oxycarbonate catalyst at a temperature of 500° C. and pressure of 125 psig.
Figure 11:
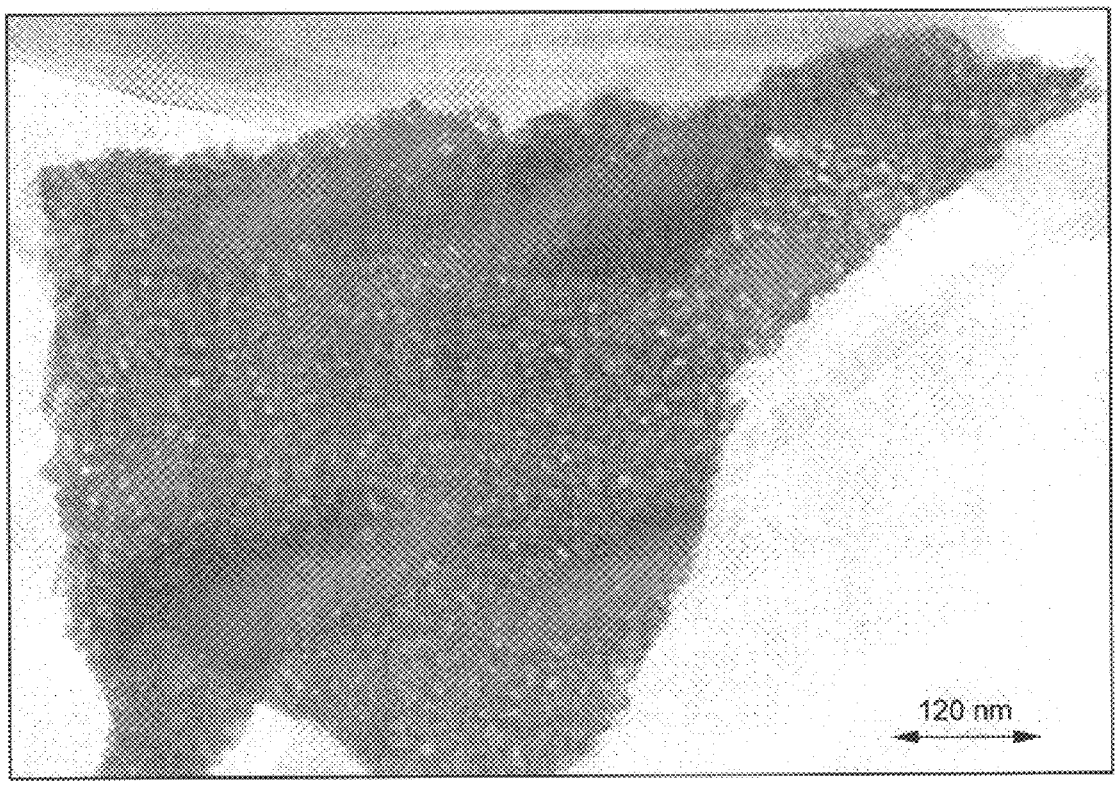
FIG. 11 is a low resolution electron microscope micrograph of a nonstoichiometric lanthanum oxycarbonate catalyst prepared by treating lanthanum oxide with aqueous acetic acid at pH 4 and calcining the material at 400° C. for one hour in flowing air (scale is 47 nm per cm).

This property is illustrated for a nonstoichiometric lanthanum oxycarbonate catalyst in FIG. 6 at an elevated pressure of 125 psig, which shows a relatively constant selectivity of 60–62% for temperatures of 400 to 550° C., a slight decline to 56% at 600° C., but a severe decline to 8% at 650° C. when the temperature becomes too high and the catalyst becomes unselective. Furthermore, after the temperature is subsequently lowered from the elevated temperature, the catalyst has lower selectivity for the oxidative dehydrogenation reaction than prior to elevating the temperature, generally having a selectivity to at least one higher hydrocarbon and/or lower olefin that is substantially lower than 40% or is unselective. Without wishing to be bound by theory, it is believed that such elevated temperatures destroy the selective catalyst composition and structure, which are not regenerated by simply cooling the material.

In addition to exhibiting high selectivity at elevated pressure, the catalysts of the present invention have been discovered to be able to maintain high selectivity for the long operating times that are necessary for commercial application. This long-term stability is illustrated in FIGS. 7–10 for four different catalysts of the present invention.

Generally after an initial decline, selectivity asymptotically approaches a steady level over time. The temperature may be adjusted incrementally after a period of operation to reestablish a higher and/or more stable selectivity. Operating parameters such as flow rate may be similarly adjusted. Conversion and other reaction characteristics are similarly stable. This long-term stability is unlike prior art catalysts, which generally suffer from a decline in selectivity to low values over a relatively short time, which frequently occurs quite rapidly.

When used for the oxidative dehydrogenation of a lower hydrocarbon at a pressure above about 100 psig, the catalyst preferably maintains a selectivity to at least one higher hydrocarbon and/or lower olefin of at least about 40%, more preferably at least about 50%, for at least about 7 days, more preferably for at least about 14 days, still more preferably for at least about 21 days, and most preferably for at least about 28 days.

Although not critical to the catalyst compositions of the present invention, higher catalyst surface area can be beneficial to producing higher selectivity. While not wishing to be bound by theory, it is believed that higher surface area can indicate greater disorder and a higher frequency of defects in the catalyst structure, which produces a higher concentration of active sites. This increases activity at lower temperature and can increase selectivity by depleting gas phase oxygen more quickly, which reduces unselective gas phase oxidation. Higher surface area can also promote heat transfer at the active sites, which keeps the catalyst surface cooler. The catalyst should generally have a surface area of at least about 3 $m^2/g$, preferably at least about 5 $m^2/g$, more preferably at least about 10 $m^2/g$, still more preferably at least about 15 $m^2/g$, and most preferably at least about 20 $m^2/g$.

The catalysts of the present invention contain at least one rare earth element selected from the group consisting of La, Pr, Nd, Sm, Eu, Gd, Tb, Dy, Ho, Er, and Tm. These rare earths have been discovered to produce catalysts having at least about 40% selectivity at pressures above about 100 psig. The rare earth element is preferably selected from the group consisting of La, Pr, Nd, Sm, Eu, Tb, and Tm, which have been discovered to produce high selectivity. The rare earth element is more preferably selected from the group consisting of La, Nd, Sm, Eu, and Tb, which produce the highest selectivity. The rare earth element is most preferably selected from the group consisting of La, Sm, and Tb. The rare earths Ce, Yb, and Lu may be used in combination with the aforementioned rare earths, but they produced low selectivity at elevated pressure when used by themselves.

When the rare earth element is selected from the group consisting of La, Pr, Nd, Sm, and Eu, it has been discovered that the catalyst can have a porous microstructure that contains pore sizes in the range of about 10 to about 1000 angstroms. As used herein, the term "porous microstructure" is understood to mean that the catalyst structure contains a three-dimensional system or network of microscopic pores, channels, and/or voids. The term "pore size" is understood to mean the characteristic diameter or dimension of the microscopic pore, channel, or void. The porous microstructure can be observed and the pore size measured by using an electron microscope, particularly at high resolution. The tendency of the rare earths to form the porous microstructure morphology diminishes in the order of La, Pr, Nd, Sm, and Eu, from a maximum for La to a minimum for Eu. The porous microstructure has not been observed for rare earths beyond Eu. The porous microstructure generally is formed and remains stable only at temperatures below about 650° C. The porous microstructure is preferably formed by calcination of a catalyst precursor, in an atmosphere that contains oxygen, at a temperature in the range of about 300° C. to about 600° C., more preferably in the range of about 400° C. to about 500° C. The porous microstructure generally does not form below about 300° C. Catalysts that have become unselective by heating them to a temperature that is too high, which is generally above about 700° C., show a collapse of the porous microstructure and possess an annealed (smoother) surface. The porous microstructure is desirable, but not critical, for forming catalysts having high surface areas above about 20 $m^2/g$, preferably above about 30 $m^2/g$. The typical pore size is preferably below about 500 angstroms, more preferably below about 300 angstroms, still more preferably below about 200 angstroms, and most preferably below about 100 angstroms.

Figure 12:
FIG. 12 is a high resolution electron microscope micrograph of the catalyst in FIG. 11 (scale is 7.7 nm per cm).
Figure 13:
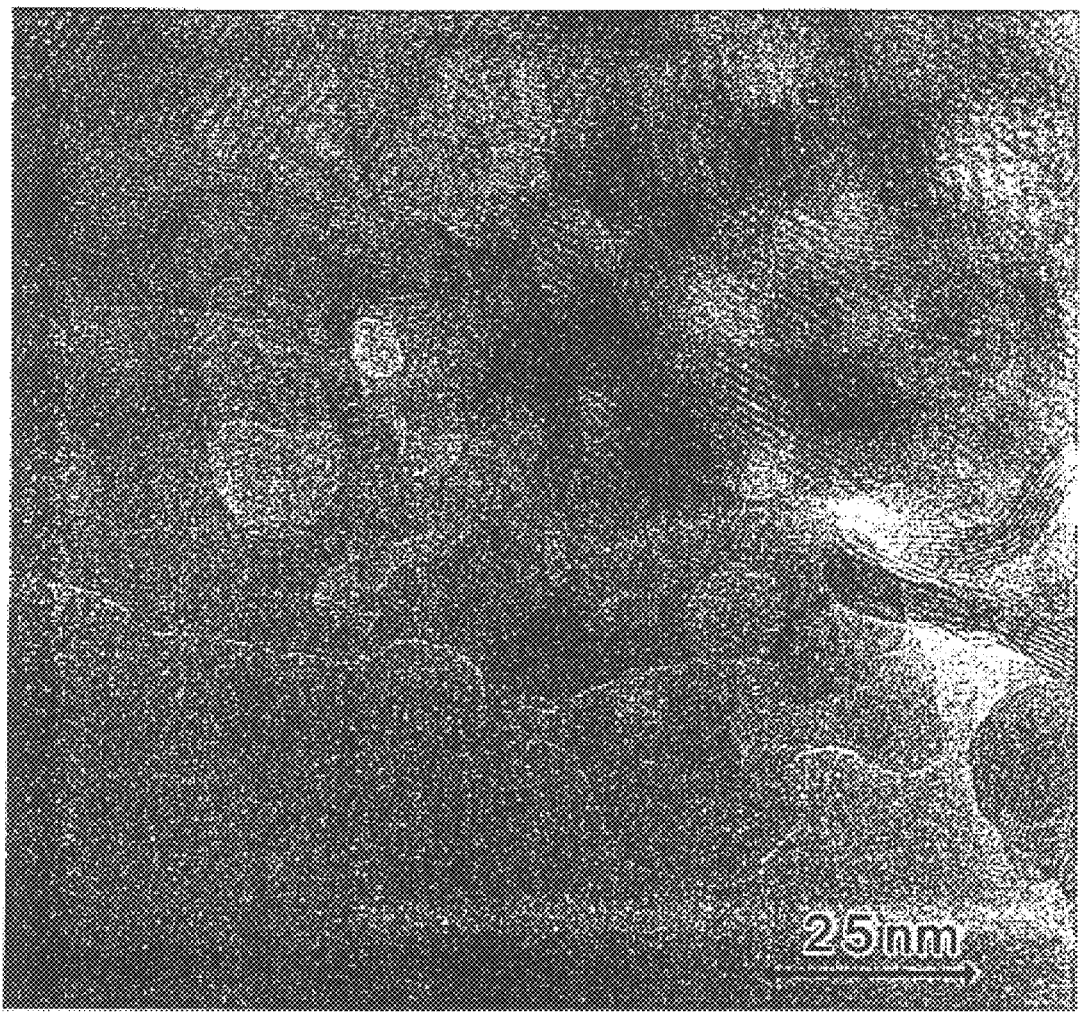
FIG. 13 is a high resolution electron microscope micrograph of a disordered nonstoichiometric lanthanum oxycarbonate catalyst prepared by treating lanthanum oxide with aqueous acetic acid at pH 4 and calcining the material at 400° C. for four hours in flowing air (scale is 10 nm per cm).
Figure 14:
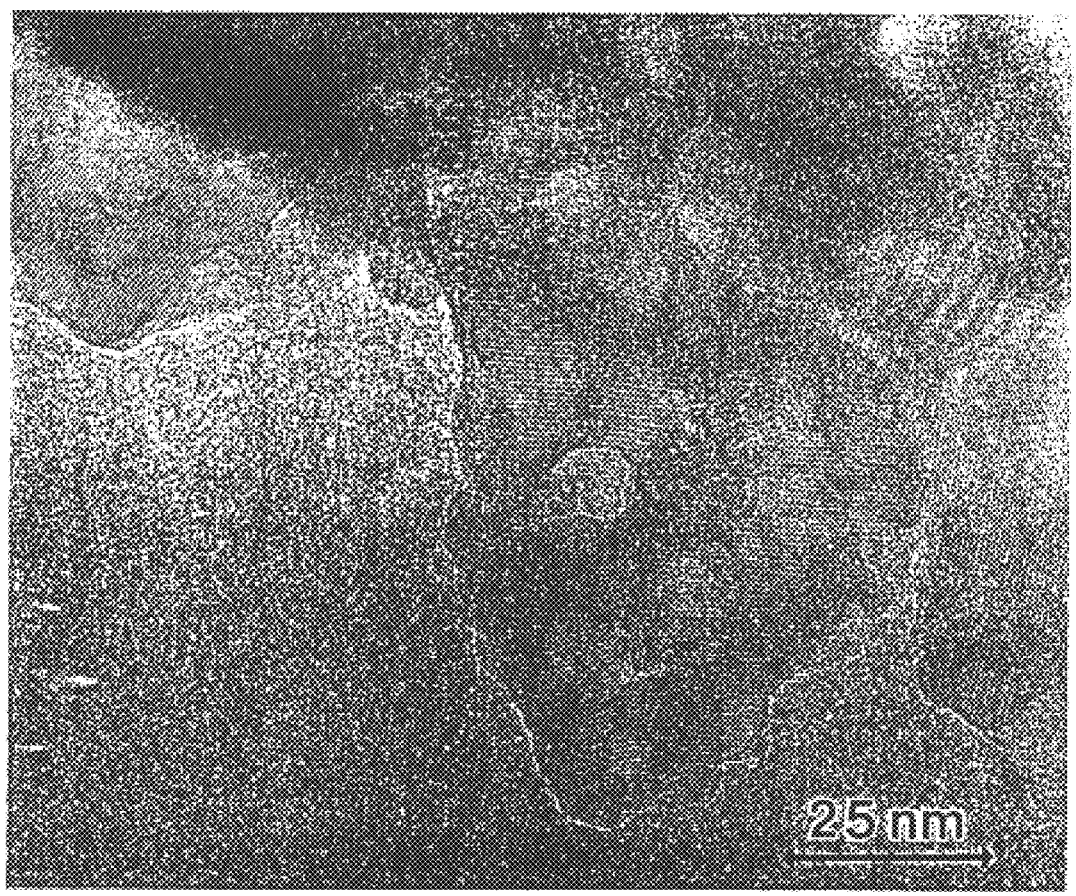
FIG. 14 is a high resolution electron microscope micrograph of a disordered nonstoichiometric lanthanum oxycarbonate catalyst prepared by treating lanthanum oxide with aqueous acetic acid at pH 4 and calcining the material at 400° C. for eight hours in flowing air (scale is 10 nm per cm).
Figure 15:
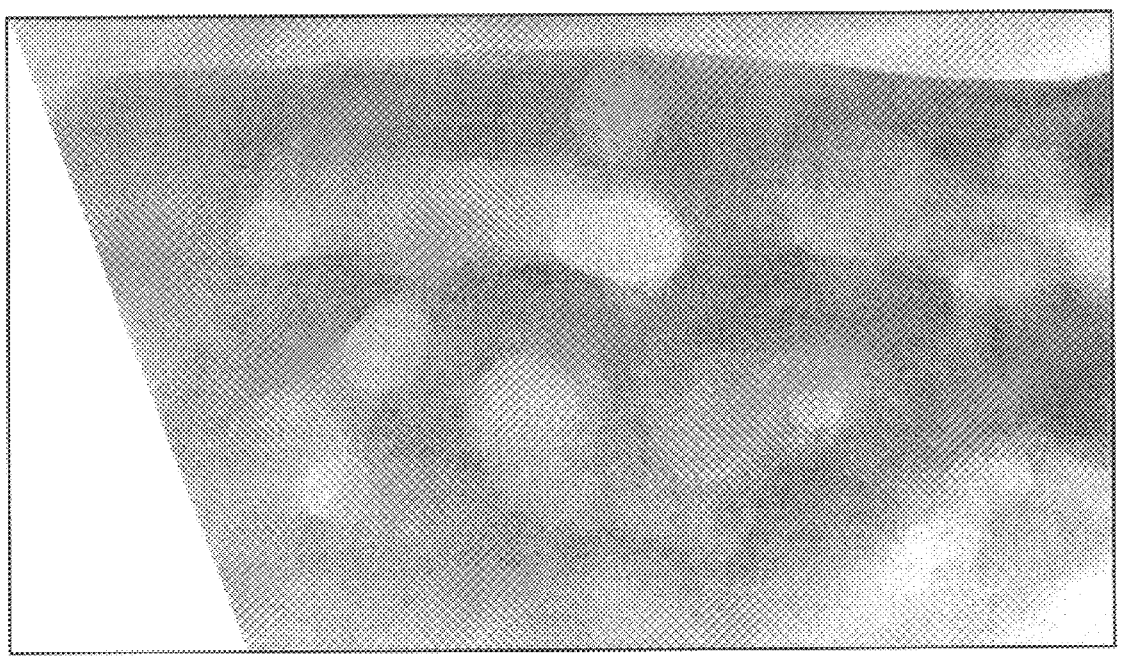
FIG. 15 is a high resolution electron microscope micrograph of a disordered nonstoichiometric lanthanum oxycarbonate catalyst prepared by treating lanthanum oxide with aqueous acetic acid at pH 4 and calcining the material at 550° C. for one hour in flowing air (scale is 7.7 nm per cm).
Figure 16:
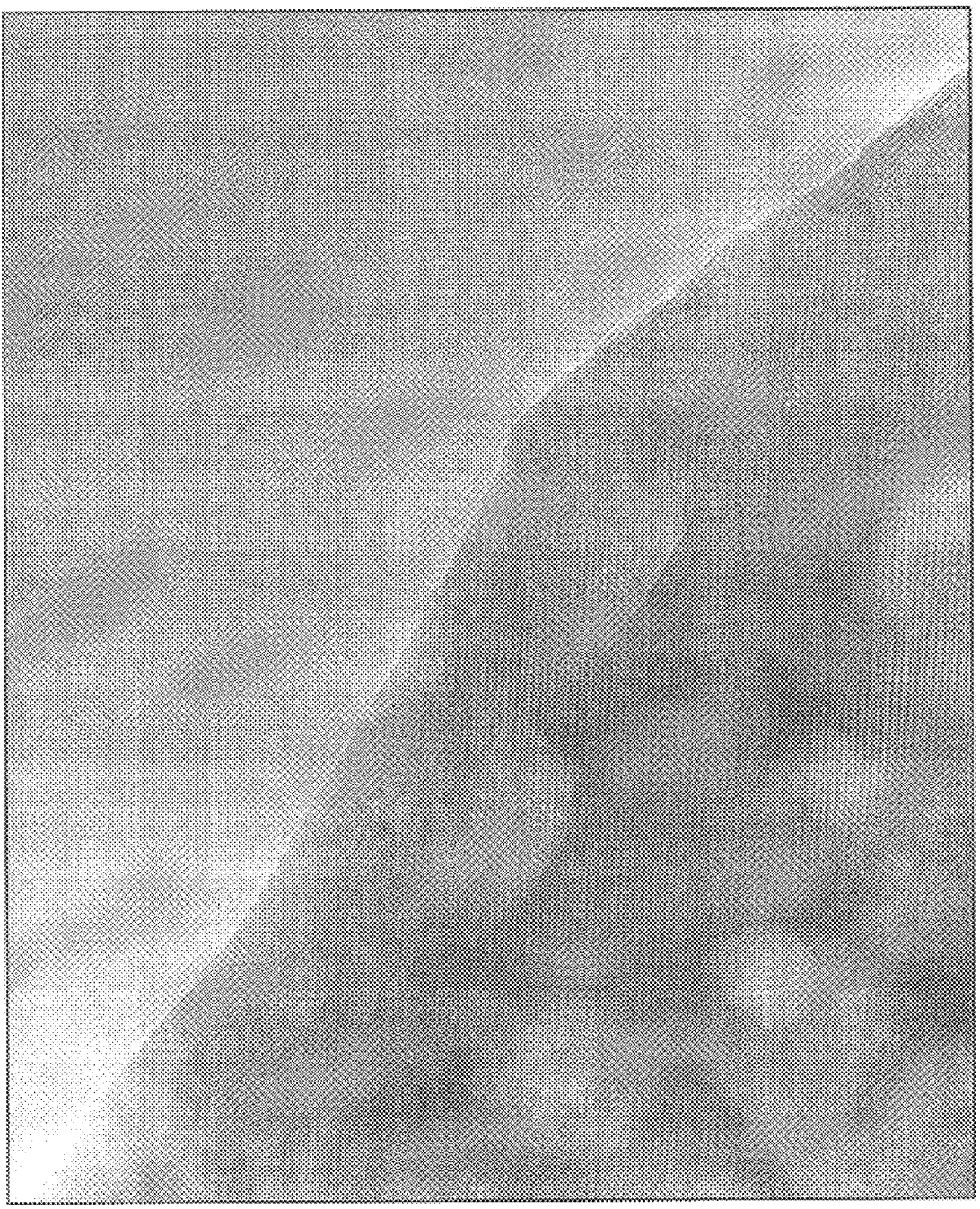
FIG. 16 is a high resolution electron microscope micrograph of disordered and nonstoichiometric lanthanum oxycarbonate prepared by treating lanthanum oxide with aqueous acetic acid at pH 4 and calcining the material at 700° C. for one hour in flowing air (scale is 7.7 nm per cm).

Electron microscope micrographs of nonstoichiometric lanthanum oxycarbonate catalysts which have a disordered and defect structure and which also have a porous microstructure are illustrated in FIGS. 11 to 16. The catalysts were prepared by treating lanthanum oxide with aqueous acetic acid at pH 4 and calcining the material in flowing air. The highly porous nature of the catalysts is illustrated by the low resolution image of FIG. 11. Catalysts calcined at 400° C. for one, four, and eight hours, which have an average parameter A value of 0.9, are shown in FIGS. 12 to 14, respectively. These high resolution images show that the materials are disordered and lack long range order, which is evident in the images as wavy or irregular lattice fringes, displace fringes, pockets of amorphous contrast, jogs in lattice fringes, moire fringes, and constantly varying image contrast. Amorphous contrast is often observed within pits on the surface. The frequency of structural faults is quite high, with defects occurring every 10 to 100 angstroms in locations, with some regions being amorphous. The porous microstructure is readily evident, with the typical diameter of the pores being between 50 to 100 angstroms. Where pores have not fully penetrated the material to form a hole or channel, the surface is pitted with voids. At a higher calcination temperature of 550° C., the disordered catalyst structure has become more ordered. The pores have also become better defined and faceting is preferred. At a high calcination temperature of 700° C., the disordered catalyst structure has become still more ordered. The pores are gradually disappearing, leaving ghost images of their location.

The nonstoichiometric rare earth oxycarbonate catalyst may further comprise a cocatalyst containing at least one metal selected from the group consisting of V, Nb, Ta, Cr, Mo, W, Mn, Re, Fe, Co, Ni, Cu, Zn, Sn, Pb, Sb, and Bi. Cocatalysts containing at least one of these metals have been discovered to be beneficial for oxidative dehydrogenation of hydrocarbons at pressures above about 100 psig. The benefits include increased selectivity, improved product distribution, lower operating temperature, and longer catalyst life. Different metals can provide different benefits, so using two or more metals can improve overall catalyst performance, which will depend upon the particular application. Without wishing to be bound by theory, it is believed that these cocatalyst metals stabilize the nonstoichiometric and disordered structure of the catalyst. As used herein, the term "cocatalyst" will be understood to include both materials that catalyze oxidative dehydrogenation as well as promoters that improve or modify catalyst performance. In addition to the aforementioned metals, the cocatalyst may contain additional elements, such as oxygen, carbon, halides, nitrogen, sulfur, phosphorous, and the like, as well as other metals, provided that they do not unsatisfactorily degrade catalyst performance. Suitable forms of the cocatalyst include but are not limited to oxides, carbonates, nitrates, phosphates, sulfates, halides, hydroxides, acetates, and the like. The cocatalyst is preferably an oxide or carbonate. The catalyst and/or cocatalyst may further comprise at least one alkali metal or alkaline earth metal, preferably at least one alkali metal, which have been found to be beneficial in suppressing combustion. In contrast, metals from the group consisting of Rh, Pd, Pt, Ag, and Au have been found to be generally unsuitable because they increase combustion, although they may be used in combination with other metals if desired.

The cocatalyst preferably contains at least one metal selected from the group consisting of V, Nb, Ta, Cr, Mo, W, Mn, Re, Fe, Sn, Pb, Sb, and Bi; more preferably at least one metal selected from the group consisting of Nb, Ta, W, Mn, Re, Fe, Pb, Sb, and Bi; and most preferably at least one metal selected from the group consisting of W, Mn, Fe, Pb, and Bi.

Cocatalyst metals that improve selectivity include Mn, Fe, W, Pb, Bi, Nb, and Sb. Cocatalyst metals that improve catalyst life include Re, Mn, Bi, Fe, and Ta. Cocatalyst metals that give lower operating temperature include Bi, Sb, Fe, Mn, Re, Nb, and Ta.

Although not critical to the catalyst composition of the present invention, the cocatalyst metal is preferably present in the catalyst in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100. The optimal amount will depend upon the actual cocatalyst composition chosen and it will generally have to be determined by systematic experimentation.

Suitable forms of the alkali metal or alkaline earth metal include but are not limited to halides, oxides, carbonates, hydroxides, nitrates, and the like. The alkali metal is preferably sodium, potassium, or cesium, most preferably sodium or potassium. Although lithium is particularly beneficial in prior art catalysts, it has been found to be detrimental with the catalysts of the present invention at elevated pressure, although it may be used if desired. The alkali metal compound is preferably selected from the group consisting of NaF, NaCl, NaBr, NaI, KCl, KBr, KI, CsCl, CsBr, CsI, sodium oxide, potassium oxide, cesium oxide, $Na_2CO_3$, $K_2CO_3$, $CSCO_3$, $NaNO_3$, $KNO_3$, $CsNO_3$, NaOH, KOH, and CsOH, and most preferably selected from the group consisting of NaCl, NaBr, KCl, sodium oxide, potassium oxide, $Na_2CO_3$, and $K_2CO_3$. The alkaline earth metal is preferably calcium, magnesium, or barium. Although strontium is particularly beneficial in prior art catalysts, it has been found to be ineffective or detrimental with the catalysts of the present invention, although it may be used if desired. The alkaline earth metal compound is preferably selected from the group consisting of $CaCl_2$, $MgCl_2$, $BaCl_2$, calcium oxide, magnesium oxide, barium oxide, $CaCO_3$, $MgCO_3$, $BaCO_3$, $Ca(NO_3)_2$, $Mg(NO_3)_2$, and $Ba(NO_3)_2$. The at least one alkali metal or alkaline earth metal may be present as a compound with the at least one cocatalyst metal.

Although not critical, the alkali metal or alkaline earth metal is preferably present in the catalyst in an amount such that the mole ratio of the metal to the rare earth is in the range of about 0.001 to about 1.000, more preferably in the range of about 0.010 to about 0.600, still more preferably in the range of about 0.020 to about 0.300, and most preferably in the range of about 0.040 to about 0.200. The optimal amount will depend upon the actual composition chosen and it will generally have to be determined by systematic experimentation. Excessively high levels are to be avoided because they can lower catalyst activity.

Suitable combinations of cocatalyst components include but are not limited to $Fe/Na_2CO_3$, $K/Fe/SO_4$, $W/Na_2CO_3$, $MnWO_4$, $Pb/WO_4$, $MnMoO_4$, $Sn/ReO_4$, $Na_2CrO_4$, $Mn/Na_2WO_4$, $Na/MnWO_4$, $Cs/Fe/WO_4$, $Na/MnMoO_4$, $Mn/Na_2CrO_4$, $K/Pb/ReO_4$, $Rb/Pb/SO_4$, $Na/Sb/ReO_4$, $Mn/Sb/TaO_3$, $K/Bi/TaO_3$, $Na/Ca/Fe/ReO_4$, $K/Mn/BiINbO_3$, $K/Mg/Sn/PO_4$, $Cs/Ca/Pb/PO_4$, $Na/Mn/Bi/NbO_3$, $K/Ba/V/NbO_3$, $K/Fe/Cr/ReO_4$, $K/Mn/Ni/ZrO_3$, $Rb/Mg/Bi/ReO_4$, $Rb/FeNV/TaO_3$, $Rb/Mn/Cr/MoO_4$, $Cs/Ba/Bi/MoO_4$, $Cs/Fe/Sb/NbO_3$, $Cs/MnNV/ReO_4$, $K/Mg/Fe/ReO_4$, $K/Mn/NaNbO_3/Sb_2O_3$, and $Mn/Li/NaTaO_3/Sb_2O_3$.

The form in which the cocatalyst is combined with the catalyst is not critical, provided that the combination is effective. The cocatalyst may be a surface deposit or intimately mixed with the catalyst material.

The physical form of the catalyst is not critical to the compositions of the present invention. The catalyst may be a powder, pressed or pelletized powder, particulates, or a bulk or formed mass. The catalyst is preferably in a form that is suitable for use in a commercial reactor, as is known to one skilled in the art. The catalyst may further comprise a support material. Using a support material can be beneficial to shape the catalyst, to enhance physical properties, such as strength, durability, and abrasion resistance, and to utilize or disperse the catalyst material more efficiently, such as to reduce cost. Suitable support materials include but are not limited to α-alumina, γ-alumina, silica, titania, magnesia, calcium oxide, and zinc oxide. The support material may have a binder or be binderless. The supported catalyst preferably has a formed shape. Suitable formed shapes include spheres, pellets, rings, extrudates, monoliths, and the like. The manner in which the catalyst is combined with the support material is not critical, provided that the combination is effective, as is known to one skilled in the art.

Second Catalyst Embodiment

The present invention is also directed to a catalyst for the oxidative dehydrogenation of a lower hydrocarbon which comprises an oxycarbonate, hydroxycarbonate, and/or carbonate of at least one rare earth element selected from the group consisting of La, Pr, Nd, Sm, Eu, Gd, Tb, Dy, Ho, Er, and Tm. When used for the oxidative dehydrogenation of a lower hydrocarbon, the catalyst exhibits higher selectivity to at least one higher hydrocarbon and/or lower olefin at a pressure above about 100 psig than the catalyst or a precursor of the catalyst exhibits at a pressure in the range of about atmospheric pressure to about 25 psig. When operating at a pressure above about 100 psig, the catalyst has a selectivity of at least about 40%.

The higher selectivity is preferably higher by at least about 2 percentage points, more preferably by at least about 4 percentage points, and most preferably by at least about 6 percentage points. The higher selectivity typically occurs at a lower temperature when at the pressure above 100 psig than when at the pressure in the range of about atmospheric pressure to about 25 psig. The catalyst furthermore has the property that it becomes unselective for the coupling reaction at an elevated temperature, which typically occurs in the range of about 600° C. to about 750° C., and after the temperature is subsequently lowered from the elevated temperature, the catalyst has lower selectivity for the oxidative dehydrogenation reaction than prior to elevating the temperature, usually having a selectivity that is substantially lower than 40% or is unselective. As before, the catalyst may also comprise a cocatalyst containing at least one metal selected from the group consisting of V, Nb, Ta, Cr, Mo, W, Mn, Re, Fe, Co, Ni, Cu, Zn, Sn, Pb, Sb, and Bi. The catalyst and/or cocatalyst may likewise further comprise at least one alkali metal or alkaline earth metal.

In contrast to prior art catalysts, we have unexpectedly discovered catalysts that can actually produce higher selectivity at elevated pressure. The table below compares selectivities obtained for oxidative coupling of methane at 125 psig for a nonstoichiometric lanthanum oxycarbonate catalyst, with NaCl to reduce combustion, and the selectivities obtained at 25 psig for the lanthanum oxide catalyst precursor, with NaCl.

| Temperature | Selectivity at 25 psig | Selectivity at 125 psig | Δ Selec. at 125–25 psig |
|---|---|---|---|
| 500° C. | 1% | 0% | −1 |
| 550° C. | 5% | 1% | −4 |
| 600° C. | 18% | 65% | +47 |
| 650° C. | 35% | 65% | +30 |
| 700° C. | 49% | 2% | −47 |

The selectivity at 125 psig is considerably higher and the catalyst becomes unselective at 700° C., whereas the catalyst precursor at 25 psig remains selective.

Figure 17:
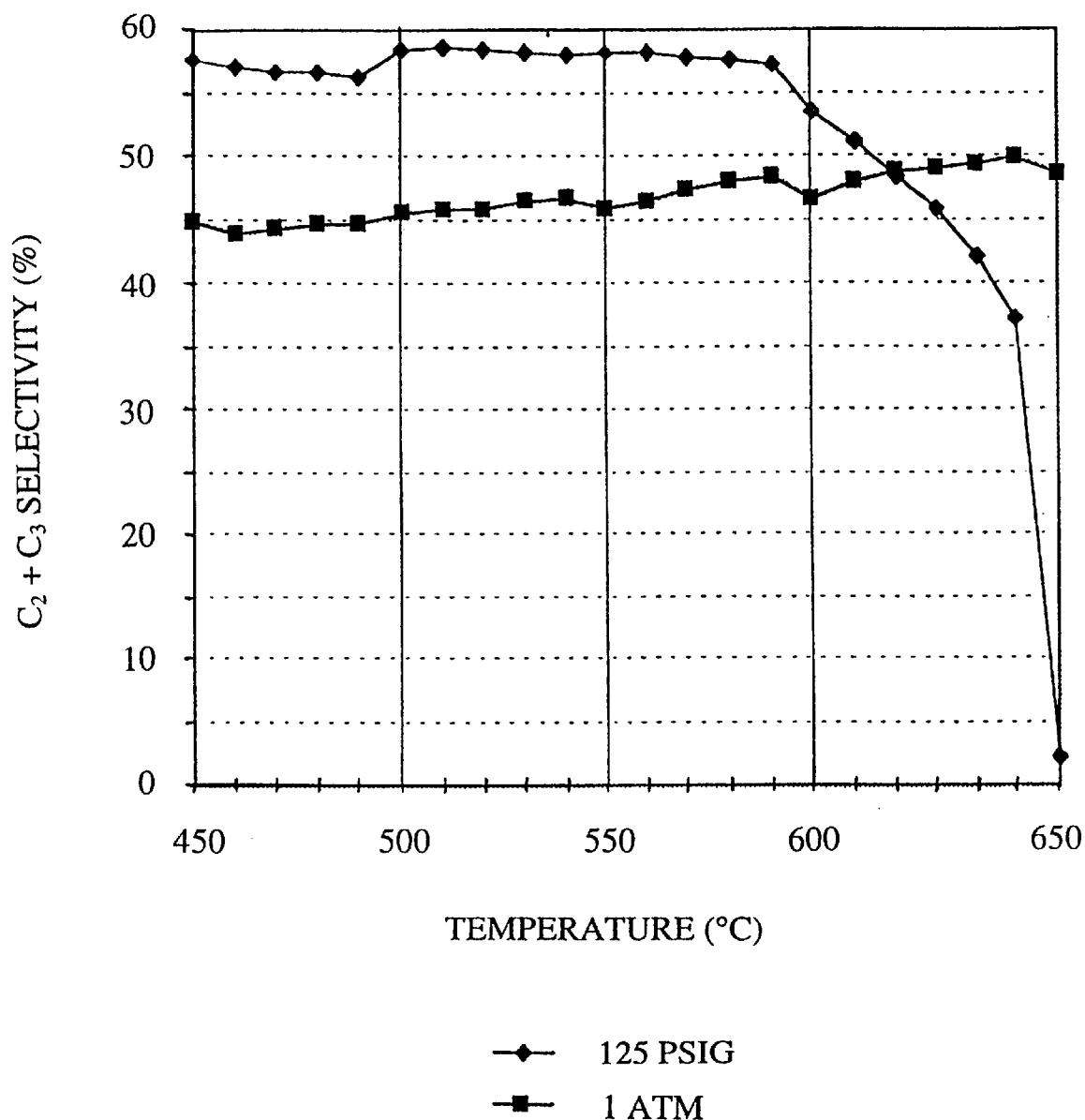
FIG. 17 is a plot of $C_2+C_3$ selectivity versus reaction temperature for oxidative coupling of methane by a nonstoichiometric lanthanum oxycarbonate catalyst with an iron oxide cocatalyst.

FIG. 17 shows a plot of $C_2+C_3$ selectivity versus temperature for oxidative coupling of methane by a nonstoichiometric lanthanum oxycarbonate catalyst with an iron oxide cocatalyst. When the catalyst precursor is reacted at atmospheric pressure, the selectivity increases continually with higher temperature from about 45% at 450° C. to about 49% at 650° C. But when the catalyst is reacted at 125 psig, the selectivity is considerably higher, about 57–58%, and is relatively constant over the temperature range of 450 to 590° C. But at 600° C., the temperature becomes too high, and the selectivity declines progressively at higher temperature until the catalyst becomes unselective at 650° C. For another comparison, a nonstoichiometric lanthanum oxycarbonate catalyst (parameter A of 1.0) with an iron oxide/$Na_2CO_3$ cocatalyst, which was prepared by treating lanthanum oxide with iron nitrate, $Na_2CO_3$, and aqueous acetic acid at pH 4 and calcining it at 400° C., was reacted at both 125 psig and 15 psig over a wide range of temperature. The maximum selectivity at 125 psig was 61% at 500° C., but the maximum selectivity at 15 psig was only 54% at 650° C.

Figure 18:
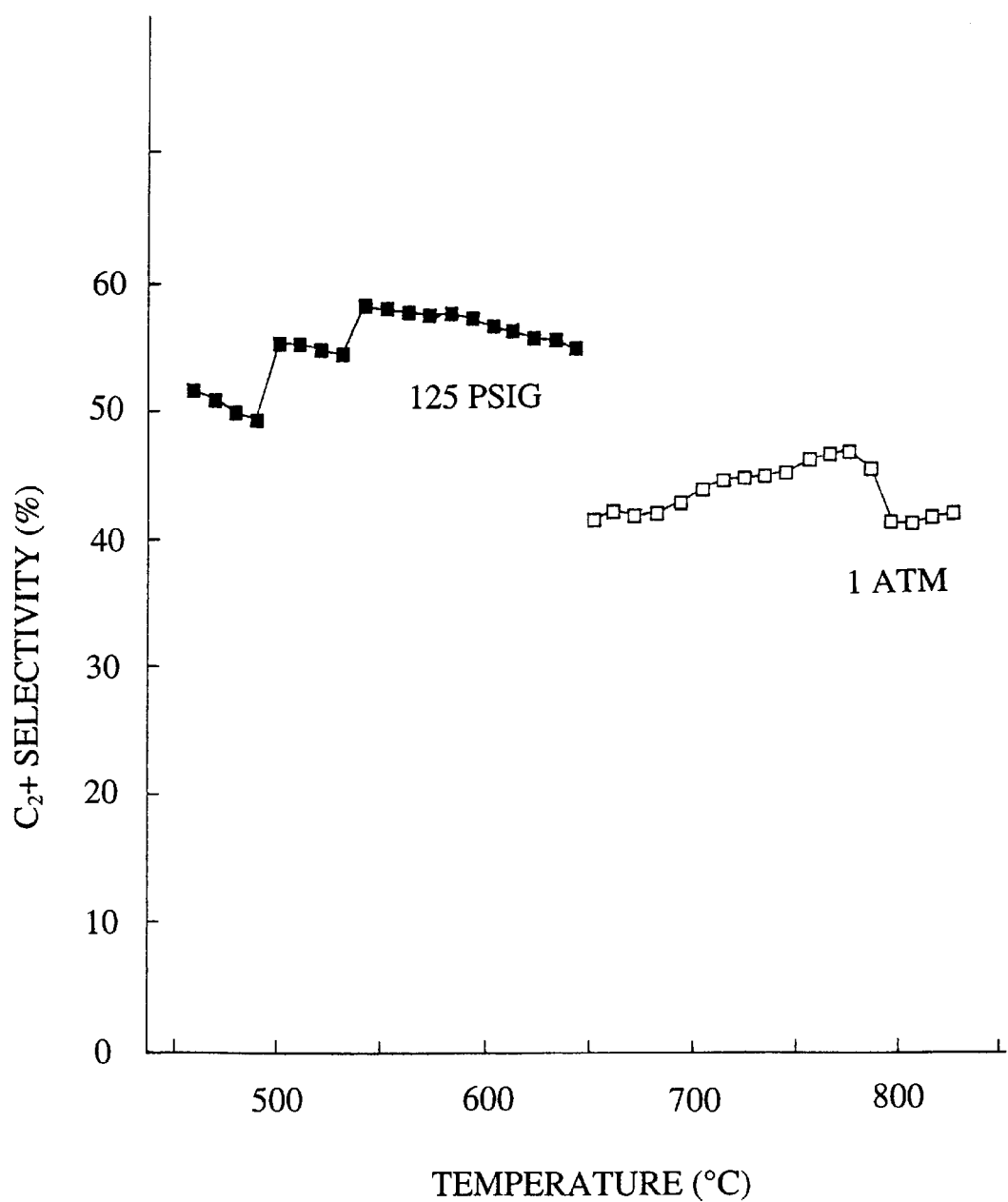
FIG. 18 is a plot of $C_2+$ selectivity versus reaction temperature for oxidative coupling of methane by a nonstoichiometric lanthanum oxycarbonate catalyst with a manganese oxide cocatalyst.

FIG. 18 shows a plot of $C_2+$ selectivity versus temperature for oxidative coupling of methane by a nonstoichiometric lanthanum oxycarbonate catalyst with a manganese oxide cocatalyst. When the catalyst precursor is reacted at atmospheric pressure, the selectivity passes through a maximum of about 45% at about 775° C., and gives no indication of becoming unselective at a higher temperature of 850° C. But when the catalyst is reacted at 125 psig, the selectivity is considerably higher, with a maximum of about 58%, at a much lower temperature of about 540° C. The comparison kept the gas composition and residence time approximately the same.

Figure 19:
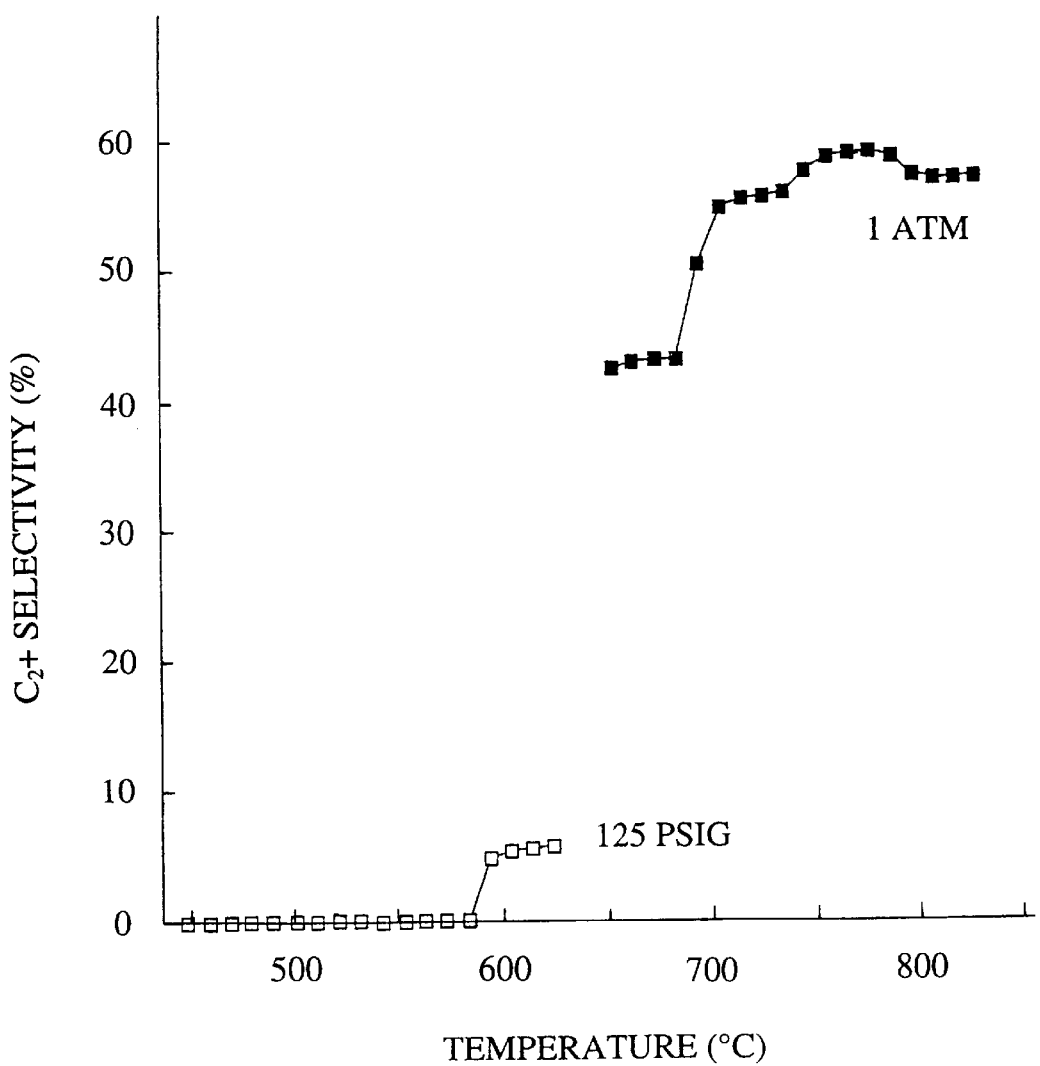
FIG. 19 is a plot of $C_2+$ selectivity versus reaction temperature for oxidative coupling of methane by a conventional lanthanum oxide catalyst not in accordance with the present invention.

For comparison, FIG. 19 shows a plot of $C_2+$ selectivity versus temperature for oxidative coupling of methane by a conventional lanthanum oxide catalyst, which is not in accordance with the present invention. When the catalyst is reacted at atmospheric pressure, the selectivity increases with temperature and reaches about 60% at 800° C. But at 125 psig, the catalyst is unselective with a very low selectivity of about 5%.

Third Catalyst Embodiment

The present invention is also directed to a catalyst for the oxidative dehydrogenation of a lower hydrocarbon which comprises (1) an oxycarbonate, hydroxycarbonate and/or carbonate of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Mn, Re, Fe, Co, Ni, Cu, Zn, Sn, Pb, Sb, and Bi. The catalyst, when used for the oxidative dehydrogenation of said lower hydrocarbon, has a selectivity of at least about 40% to at least one higher hydrocarbon and/or lower olefin.

The cocatalyst preferably contains at least one metal selected from the group consisting of Nb, Ta, W, Mn, Re, Fe, Pb, Sb, Bi, and most preferably at least one metal selected from the group consisting of W, Mn, Fe, Pb, and Bi. The cocatalyst metal is preferably present in the catalyst in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100.

The catalyst and/or cocatalyst may further comprise at least one alkali metal or alkaline earth metal, preferably at least one alkali metal. The rare earth oxycarbonate is a preferably a nonstoichiometric rare earth oxycarbonate of the formula $M_XC_YO_Z$, wherein M is the rare earth element; X=2; Z=3+AY; the parameter A is less than about 1.8; and Y is the number of carbon atoms in the oxycarbonate. The rare earth oxycarbonate, hydroxycarbonate, and/or carbonate preferably has a disordered and/or defect structure.

Fourth Catalyst Embodiment

The present invention is also directed to a catalyst for the oxidative dehydrogenation of a lower hydrocarbon, which comprises (1) an oxide of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Re, Fe, Co, and Ni. The catalyst, when used for the oxidative dehydrogenation of said lower hydrocarbon, has a selectivity of at least about 40% to at least one higher hydrocarbon and/or lower olefin. The cocatalyst preferably contains at least one metal selected from the group consisting of V, Nb, Ta, Cr, Re, and Fe. The cocatalyst metal is preferably present in the catalyst in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100. The catalyst and/or cocatalyst may further comprise at least one alkali metal or alkaline earth metal, preferably at least one alkali metal. The rare earth oxide preferably has a disordered and/or defect structure. The disordered structure of the catalyst preferably has short range order that is substantially limited to being less than about 100 angstroms. The catalyst structure preferably is substantially characterized by defects that occur with a frequency of more than about one defect per 100 angstroms. When used for the oxidative dehydrogenation of a lower hydrocarbon at a pressure above about 100 psig, the catalyst preferably has a selectivity to at least one higher hydrocarbon and/or lower olefin of at least about 40%, more preferably at least about 50%.

First Method Embodiment

One method for preparing a nonstoichiometric rare earth oxycarbonate catalyst having a disordered and/or defect structure comprises, in general, the steps of first forming a catalyst precursor and then forming a catalyst from the catalyst precursor at elevated pressure.

The catalyst precursor is formed from at least one rare earth compound that includes at least one rare earth element selected from the group consisting of La, Pr, Nd, Sm, Eu, Gd, Tb, Dy, Ho, Er, and Tm and in addition includes at least oxygen. The rare earth element is preferably selected from the group consisting of La, Pr, Nd, Sm, Eu, Tb, and Tm, and more preferably from the group consisting of La, Nd, Sm, Eu, and Tb. In addition to oxygen, the rare earth compound may include other elements, such as carbon, hydrogen, nitrogen, sulfur, halides, phosphorous, and the like. The rare earth compound may be selected from the group consisting of rare earth oxides, hydroxides, acetates, chloroacetates, oxalates, carbonates, stoichiometric oxycarbonates, nitrates, sulfates, and phosphates. Other oxygenated compounds may also be used. The rare earth compound is preferably selected from the group consisting of rare earth oxides, hydroxides, acetates, carbonates, and nitrates; more preferably selected from the group consisting of rare earth oxides, hydroxides, and acetates; and most preferably is a rare earth oxide.

The at least one rare earth compound is treated with at least water and/or an organic compound that contains a hydroxyl group. The organic compound is preferably an alcohol, such as methanol, ethanol, propanol, isopropanol, or butanol. As used herein, the terms "treated" and "treating" are understood to mean that the rare earth compound and a fluid material are combined with intimate contact such that the fluid material can act upon the rare earth compound, and includes forming a hydrate of the rare earth compound. Generally the rare earth compound is simply either mixed with or added to the water and/or organic compound so that the rare earth compound is wetted or immersed. The rare earth compound may also be treated with an acid, preferably an organic acid. The organic acid may be acetic acid, formic acid, propionic acid, lactic acid, citric acid, or butyric acid, and is preferably acetic acid. The rare earth compound is preferably treated with the organic acid to form an aqueous mixture having a final pH in the range of about 2 to about 6, more preferably in the range of about 3 to about 5.

The treated rare earth compound is then dried. The method is not critical to the present invention, and drying methods may be used that are known to one skilled in the art. Generally the material is dried at low temperatures in the range of from ambient temperature to about 90° C. to about 150° C., preferably at about 100° C. to about 140° C. The drying may be done in air, under vacuum, or in an inert atmosphere such as nitrogen. The drying may be done under a flowing atmosphere, which may include the solvent below its saturation level at ambient conditions to control the rate of drying. In the case of water this is referred to by those skilled in the art as controlled humidity drying. When an organic compound is dried, the drying atmosphere should be kept below flammable limits for safety. The drying atmosphere preferably contains a low concentration of carbon dioxide, preferably below about 1%, and most preferably does not exceed atmospheric level of carbon dioxide. The drying time or degree of dryness is not critical. Generally the material is dried until free liquid has evaporated. The treated rare earth compound may be dried during calcination if desired.

The treated rare earth compound is then calcined at a temperature in the range of about 300° C. to about 1000° C. in an atmosphere containing oxygen. The calcination temperature is preferably in the range of about 350° C. to about 900° C., more preferably in the range of about 400° C. to about 800° C., and most preferably in the range of about 400° C. to about 600° C. The calcination time is not critical, provided that sufficient calcination is achieved, but preferably should be in the range of a few minutes (1–30 minutes) to about 12 hours, more preferably in the range of about 45 minutes to about 8 hours, still more preferably in the range of about 45 minutes to about 6 hours, and most preferably in the range of about 1 hour to about 4 hours.

Unlike prior art preparations, calcination atmospheres that have no oxygen have been found to be detrimental and to produce catalysts having lower selectivity. The calcination atmosphere preferably contains oxygen in the range of about 5% to about 100%, more preferably in the range of about 10% to about 70%, still more preferably in the range of about 15% to about 50%, and most preferably in the range of about the oxygen content of air to about 30%. The atmosphere containing oxygen is preferably inert and is generally air, but it may also be oxygen-enriched air or oxygen. The catalyst precursor should be calcined in such manner that the bulk of the calcined material is in effective contact with the atmosphere containing oxygen. A flowing atmosphere, such as flowing air, is desirable to maintain a supply of oxygen during the calcination, particularly when the catalyst precursor is prepared in bulk. The flow rate of the air is not critical, provided that an adequate oxygen concentration is maintained. Any effective method may be used, such as providing fresh atmosphere to the calcination chamber, blowing the atmosphere onto or through the material, conveying the material such as on a conveyor belt, bubbling the atmosphere through the material, or using a fluidized bed or riser bed. Other continuous belt dryer/roasters known in the art may be used, such as those disclosed in Siles, A. and Koch, T., *Catalyst Manufacture*, Marcel Decker, Inc., $2^{nd}$ ed., pp. 47–48 and 68–69 (1995). Unlike prior art preparations, the presence of more than a few percent of carbon dioxide during calcination has been found to be detrimental and to produce catalysts having lower selectivity. Therefore the calcination atmosphere preferably contains a low concentration of carbon dioxide, preferably below about 1%, and most preferably does not exceed atmospheric level of carbon dioxide.

At least one cocatalyst compound containing at least one metal selected from the group consisting of V, Nb, Ta, Cr, Mo, W, Mn, Re, Fe, Co, Ni, Cu, Zn, Sn, Pb, Sb, and Bi may also be added to the at least one rare earth compound and/or the catalyst precursor. The manner in which the cocatalyst compound is added is not critical. The cocatalyst compound may be added directly to the rare earth compound, such as in a finely divided form. The cocatalyst compound may be added to the water and/or organic compound that contains a hydroxyl group that is used to treat the rare earth compound, such as by forming a solution, dispersion, or suspension. The cocatalyst compound may be added to the catalyst precursor, such as by dissolving or finely dispersing or suspending the cocatalyst compound in water, an organic compound that contains a hydroxyl group, or another medium; applying the mixture to the catalyst precursor, such as by immersion or incipient wetness; and then drying and calcining the combination by using the procedures and conditions discussed for preparation of the catalyst precursor. The cocatalyst metal is preferably added in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100. Suitable cocatalyst compounds include but are not limited to nitrates, oxides, carbonates, phosphates, sulfates, halides, hydroxides, acetates, hydrates, salts, and the like. The cocatalyst may further comprise at least one alkali metal or alkaline earth metal, preferably at least one alkali metal. Nitrates, hydrates, oxides, sodium salts, and ammonium salts are particularly preferred. Examples are $Fe(NO_3)_3$, $Fe(NO_3)_3 \cdot 9H_2O$, $Mn(NO_3)_2$, $Mn(NO_3)_2 \cdot 6H_2O$, $Bi(NO_3)_3$, $Bi(NO_3)_3 \cdot 5H_2O$, $MnWO_4$, $MnMoO_4$, $Sb_2O_3$, $NaNbO_3$, $Na_2WO_4$, $Na_2WO_4 \cdot 2H_2O$, $Na_2CrO_4$, $Na_2CrO_4 \cdot 2H_2O$, sodium rhenate, sodium niobate, ammonium tungstate, and ammonium rhenate.

In the same manner, at least one alkali metal or alkaline earth metal compound may be added to the at least one rare earth compound and/or the catalyst precursor. Suitable alkali metal or alkaline earth metal compounds include but are not limited to halides, oxides, carbonates, hydroxides, nitrates, and the like. The alkali metal compound is preferably selected from the group consisting of NaF, NaCl, NaBr, NaI, KCl, KBr, KI, CsCl, CsBr, CsI, sodium oxide, potassium oxide, cesium oxide, $Na_2CO_3$, $K_2CO_3$, $CsCO_3$, $NaNO_3$, $KNO_3$, $CsNO_3$, NaOH, KOH, and CsOH, and most preferably selected from the group consisting of NaCl, NaBr, KCl, sodium oxide, potassium oxide, $Na_2CO_3$, and $K_2CO_3$. The alkaline earth metal is preferably calcium, magnesium, or barium. The alkaline earth metal compound is preferably selected from the group consisting of $CaCl_2$, $MgCl_2$, $BaCl_2$, calcium oxide, magnesium oxide, barium oxide, $CaCO_3$, $MgCO_3$, $BaCO_3$, $Ca(NO_3)_2$, $Mg(NO_3)_2$, and $Ba(NO_3)_2$. The sulfate and phosphate salts of the alkali and alkali earth metals may also be used. The alkali metal or alkaline earth metal is preferably added in an amount such that the mole ratio of the metal to the rare earth is in the range of about 0.001 to about 1.000, more preferably in the range of about 0.010 to about 0.600, still more preferably in the range of about 0.020 to about 0.300, and most preferably in the range of about 0.040 to about 0.200. Other materials, such as a cerium compound, for example cerium nitrate, may also be added.

The catalyst precursor may be formed on or mixed with a support material. Suitable support materials include but are not limited to α-alumina, γ-alumina, silica, titania, magnesia, calcium oxide, and zinc oxide. The support material may have a binder or be binderless. The supported catalyst preferably has a formed shape. Suitable formed shapes include spheres, microspheres (for fluid bed reactor use), pellets, rings, extrudates, monoliths, and the like. The method in which the catalyst precursor is formed on or added to the support material is not critical, and any method known to one skilled in the art may be used.

The at least one rare earth compound and optionally at least one cocatalyst compound, at least one alkali metal or alkaline earth metal compound, and/or other materials are generally added to the support material as a solution, dispersion, or suspension prior to and/or during the drying step. More than one application of the materials to the support material may be used if desired, such as to build up the catalyst precursor in more than one layer. The materials may be applied together or sequentially. The material may be dried or dried and calcined between applications.

One method is to combine the catalyst precursor materials, liquid treatment agent such as water and/or alcohol, and the support material, and to then dry the mixture to deposit the materials onto the support, such as by using a rotary evaporator. Another method is to put the support material into a vessel, fill the vessel with a mixture of catalyst precursor materials and liquid treatment agent, optionally put the vessel under vacuum and repressurize it several times to provide good contacting, drain the liquid, and dry the impregnated support material. These procedures may be repeated to build up the amount of deposited material to the desired level, or to apply the materials sequentially, without or with calcination between each impregnation.

The amount of catalyst precursor applied to the support material is not critical provided that the combination is effective. Generally it is economically beneficial to apply the minimal amount that provides desired performance, whereas selectivity generally increases with catalyst loading until a maximum level is obtained which is similar to that obtained for an unsupported catalyst. The amount of rare earth metal, when measured as the corresponding oxide, in the combined catalyst precursor and support material by weight is preferably in the range of about 5% to about 90% of the combination, more preferably in the range of about 10% to about 70%, still more preferably in the range of about 20% to about 60%, and most preferably in the range of about 25% to about 50%. The combination of catalyst precursor and support material may also be formed by coprecipitating or comixing the catalyst precursor materials with the support material and optionally an inorganic binder such that particulates of the support material form a continuing support linkage after calcination to provide robust catalyst particles. The combined mixture may be formed into a shaped form and into a size that is suitable for a commercial reactor.

This procedure may also be used to prepare the catalysts of the present invention that comprise rare earth oxide and cocatalyst containing at least one metal selected from the group consisting of V, Nb, Ta, Cr, Mo, W, Re, Fe, Co, and Ni.

The nonstoichiometric rare earth oxycarbonate catalyst having a disordered and/or defect structure is then formed by (a) pressurizing the catalyst precursor to a pressure of at least about 100 psig with a flowing gas that contains at least one hydrocarbon and oxygen and (b) heating the catalyst precursor and holding the catalyst precursor for at least about 20 minutes at one or more temperatures within the temperature range of about 300° C. to about 600° C. wherein oxygen conversion is below about 70%.

The at least one hydrocarbon in the flowing gas is not critical and is generally a lower hydrocarbon such as methane, ethane, propane, butane, and the like. The hydrocarbon is generally the hydrocarbon feedstock to be used for oxidative dehydrogenation, but another hydrocarbon may be used. The hydrocarbon is preferably methane or ethane, and is most preferably methane. The source of the oxygen in the flowing gas is not critical. High-purity oxygen is preferred, but air, oxygen-enriched air, or another oxygenated gas may be used if desired. The oxygen level must be maintained sufficiently below the explosive limit to provide safe operation. Generally the oxygen concentration is maintained at about 10% to 13% or lower by volume. The oxygen level is generally about the same level used for oxidative dehydrogenation. The mole ratio of hydrocarbon to oxygen is preferably in the range of about 4/1 to about 12/1, more preferably in the range of about 5/1 to 9/1. The flowing gas may also contain inert gases such as nitrogen, helium, argon, and the like if desired, but the levels should not be excessive, and preferably are below about 30% by volume, more preferably below about 20%. Undesirable impurities, such as poisons for the catalyst, are preferably present at the low levels that are acceptable for oxidative dehydrogenation. The presence of carbon dioxide has been found to be detrimental and to produce catalysts having lower selectivity. Therefore the flowing gas should contain a low concentration of carbon dioxide that is below about 5% by volume, preferably below about 2%, more preferably below about 1%, and most preferably below about 0.5%.

The catalyst precursor is pressurized by the flowing gas within a pressure vessel, which may be the reactor used for oxidative coupling. The type of pressure vessel, the method of contacting the flowing gas and catalyst precursor, and the flow rate are not critical provided that the flowing gas effectively contacts the catalyst precursor and the temperature or temperatures and oxygen conversion are maintained within the specified limits. The pressure vessel may be a tube, a tank, or another configuration. The pressure vessel may have a means for heating, such as a heater or a heat exchanger, and/or the flowing gas may be preheated. The flow rate is preferably in the range of about 100 to about 10,000 cc/min/g of catalyst precursor, more preferably in the range of about 200 to about 5,000 cc/min/g, and most preferably in the range of about 300 to about 2000 cc/min/g.

The catalyst precursor is pressurized by the flowing gas to a pressure of at least about 100 psig. The pressure is generally about the pressure at which the oxidative dehydrogenation reaction is done. The pressure is preferably less than about 600 psig, more preferably less than about 400 psig, and still more preferably less than about 300 psig. The pressure is most preferably in the range of about 125 to about 250 psig.

The catalyst precursor is heated and while pressurized the catalyst precursor is held for at least about 20 minutes at one or more temperatures within the temperature range of about 300° C. to about 600° C. at which oxygen conversion is below about 70%. Under these conditions the catalyst precursor is converted to a nonstoichiometric rare earth oxycarbonate catalyst having a disordered and/or defect structure. Temperatures below about 300° C. are generally too low for the conversion to occur, and the nonstoichiometric oxycarbonate catalyst tends to degenerate and become unselective at temperatures in the range of about 600° C. to about 750° C. Within the temperature range of about 300° C. to about 600° C., the catalyst precursor is held at a temperature or temperatures at which oxygen conversion is below about 70%.

Without wishing to be bound by theory, this is believed to provide a beneficial combination of interactions between the catalyst precursor material, the reaction intermediate species produced by oxidation of the hydrocarbon, and oxygen absorbed from the flowing gas. This produces a stable realignment of the rare earth element, carbon, and oxygen contents to give a nonstoichiometric oxycarbonate that is rich in carbon and deficient in oxygen. The treatment of the rare earth compound with water and/or an organic compound that contains a hydroxyl group is believed to condition the rare earth compound to facilitate absorption of the reaction intermediate species. When the catalyst precursor does not contain carbon, such as rare earth oxide, hydroxide, nitrate, sulfate, or phosphate, absorption of the reaction intermediate species also incorporates carbon into the catalyst structure.

The incorporation of reaction intermediate species instead of just carbon dioxide is believed to produce the carbon rich and oxygen deficient composition. This realignment of the composition of the catalyst precursor is also believed to produce a realignment of the morphology as well, which produces disorder and defects in the structure. The elevated pressure is believed to have a beneficial effect by substantially increasing the concentration of reaction intermediate species and enabling the conversion to occur at moderate temperatures at which the catalyst composition is stable and selective.

The manner in which the catalyst precursor is held at the temperature or temperatures at which oxygen conversion is below about 70% within the temperature range of about 300° C. to about 600° C. is not critical. The temperature may be continually ramped at a slow rate, held at a steady value, stepped incrementally, or any other suitable temperature schedule may be used, or a combination thereof. Selectivity has in general been found to increase asymptotically with the time interval over which the catalyst transformation is allowed to occur. The catalyst precursor is therefore preferably held for at least about 30 minutes, more preferably for at least about 40 minutes, and most preferably for at least about 50 minutes at the temperature or temperatures at which oxygen conversion is below about 70% within the temperature range of about 300° C. to about 600° C. Long times of 4 hours, 8 hours, or longer may also be used. The oxygen conversion level is also not critical and may change during the time interval. The oxygen conversion level is preferably below about 50%. The catalyst transformation has been found to occur even at very low oxygen conversion levels. However, it is generally beneficial to use a longer time interval when at a lower temperature that gives a lower oxygen conversion level. The oxygen conversion is preferably above about 1%, more preferably above about 2%, and most preferably above about 4%. The temperature or temperatures within which the oxygen conversion is held below about 70% is preferably in the range of about 350° C. to about 550° C., more preferably in the range of about 400° C. to about 550° C., and most preferably in the range of about 400° C. to about 500° C.

Second Method Embodiment

A similar method for preparing a nonstoichiometric rare earth oxycarbonate catalyst having a disordered and/or defect structure and which also includes a cocatalyst generally comprises the steps of first forming a catalyst precursor and then forming the nonstoichiometric catalyst from the precursor at elevated pressure. The catalyst precursor is formed from a mixture comprising at least one rare earth compound which has been combined with at least on cocatalyst compound. The rare earth compound includes at least one rare earth element selected from the group consisting of La, Pr, Nd, Sm, Eu, Gd, Tb, Dy, Ho, Er, and Tm, and, in addition, includes at least oxygen. The cocatalyst compound includes at least one metal selected from the group consisting of Fe, Mn, W, and Mo.

The rare earth compound may be the same as those described above in connection with the first method embodiment, and it has been found that cocatalyst compounds which contain at least one metal selected from the group consisting of Fe, Mn, W, and Mo enhance catalyst formation. Without wishing to be bound by theory, these metals are believed to aid formation of the nonstoichiometric and disordered structure of the catalyst. They allow selective catalysts to be formed more rapidly and at lower temperature. The cocatalyst metal is preferably added in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100. Suitable cocatalyst compounds include but are not limited to nitrates, oxides, carbonates, phosphates, sulfates, halides, hydroxides, acetates, hydrates, salts, and the like. The cocatalyst may further comprise at least one alkali metal or alkaline earth metal, preferably at least one alkali metal. As before, at least one alkali metal and/or alkaline earth metal compound, or other materials may also be added, and the catalyst precursor may be formed on or mixed with a support material.

The mixture of the rare earth compound and cocatalyst compound is treated with at least water and/or an organic compound that contains a hydroxyl group and then dried and calcined at a temperature in the range of about 300° C. to about 1000° C. in an atmosphere containing oxygen, as before.

The nonstoichiometric catalyst is then formed by (a) pressurizing the catalyst precursor to a pressure of at least about 100 psig with a flowing gas that contains at least one hydrocarbon and oxygen, as before, and (b) heating the catalyst precursor at one or more temperatures at which oxygen conversion occurs within the temperature range of about 300° C. to about 700° C., preferably within the temperature range of about 350° C. to about 650° C., and more preferably within the temperature range of about 400° C. to about 600° C.

Third Method Embodiment

A nonstoichiometric rare earth oxycarbonate catalyst having a disordered and/or defect structure and a surface area greater than about 20 $m^2/g$ is prepared by a method which comprises the following three general steps. In the first step, at least one finely divided solid rare earth compound that includes at least one rare earth element selected from the group consisting of La, Pr, Nd, Sm, Eu, Gd, Tb, Dy, Ho, Er, and Tm, and oxygen is treated with water and organic acid such that the final pH of the aqueous mixture is in the range of about 2 to about 6 and obtains a substantially constant value. The finely divided solid provides high surface area for treatment by the water and organic acid. As used herein, the phrase "finely divided solid" is understood to mean powder or fine particulates. The finely divided solid preferably has a particle size below about 30 mesh, more preferably below about 50 mesh. The rare earth compound is preferably selected from the group consisting of rare earth oxides, hydroxides, nitrates, sulfates, and phosphates, and is most preferably rare earth oxide. The organic acid is preferably selected from the group consisting of acetic acid, formic acid, propionic acid, and butyric acid; more preferably acetic acid and/or formic acid; and most preferably acetic acid.

The method of combining the rare earth compound, water, and organic acid is not critical provided that at least the final pH of the aqueous mixture is in the desired range of about 2 to about 6 and obtains about a constant value. Generally the rare earth compound is mixed with at least enough water to provide a fluid mixture when stirred, such as about 5 ml of water per gram of rare earth compound, and then organic acid is added. During the acid treatment, the acid is generally added incrementally as in a titration. It is not critical that the pH remain within the desired range during the entire time that the acid is added until the pH obtains about a constant value. Interaction with the rare earth compound tends to neutralize the acid and to swing the pH towards basic, which indicates that more acid needs to be added, until the treatment of the rare earth compound is completed, after which the pH obtains a substantially constant value, preferably a constant value.

The rate of addition of the acid is determined by the rate at which the acid interacts with the rare earth compound. The amount of acid that needs to be added is generally proportional to the amount of rare earth compound. The pH of the mixture preferably is maintained within the desired range for at least the final 25% of the acid addition, more preferably at least the final 50%, and most preferably for at least the final 75%. The mixture is preferably well mixed during the acid treatment to provide good contact between the rare earth and the organic acid and to maintain a uniform pH. The concentration of the acid added to the mixture is not critical.

The acid preferably is dilute enough to maintain adequate pH control but concentrated enough to not overly dilute the mixture. The acid concentration is preferably in the range of about 10% to about 50% by weight, and the acid is preferably added slowly or in small increments.

The final pH of the aqueous mixture is preferably in the desired range of about 2.5 to about 5.5, more preferably in the range of about 3 to about 5, still more preferably in the range of about 3.5 to about 4.5, and most preferably is about 4. After the pH obtains about a constant value, the treated rare earth compound may remain in contact with the acid medium for a longer period of time if desired, such as to confirm that about constant pH has been obtained. The acid medium generally is not drained from the treated rare earth compound and the treated rare earth compound is generally not washed before drying.

At least one cocatalyst compound including at least one metal selected from the group consisting of V, Nb, Ta, Cr, Mo, W, Mn, Re, Fe, Co, Ni, Cu, Zn, Sn, Pb, Sb, and Bi may also be added to the at least one rare earth compound. The manner in which the cocatalyst compound is added is not critical, and it may be added before, during, or after the acid treatment, and it may be added to form a solution, dispersion, or suspension. The cocatalyst metal is preferably added in an amount such that the mole ratio of the metal to the rare earth is in the range of about 0.001 to about 1.000, more preferably in the range of about 0.005 to about 0.400, still more preferably in the range of about 0.010 to about 0.200, and most preferably in the range of about 0.020 to about 0.100.

Suitable cocatalyst compounds include, but are not limited to, nitrates, oxides, carbonates, phosphates, sulfates, halides, hydroxides, acetates, hydrates, salts, and the like. The cocatalyst may further comprise at least one alkali metal or alkaline earth metal, preferably at least one alkali metal. The cocatalyst compound is preferably soluble in water or aqueous organic acid. Nitrates, hydrates, sodium salts, and ammonium salts are particularly preferred. Examples are $Fe(NO_3)_3$, $Fe(NO_3)_3 \cdot 9H_2O$, $Mn(NO_3)_2$, $Mn(NO3)_2 \cdot 6H_2O$, $Na_2WO_4$, $Na_2WO_4 \cdot 2H_2O$, and the like.

In the same manner, at least one alkali metal or alkaline earth metal compound may be added to the at least one rare earth compound. Suitable alkali metal or alkaline earth metal compounds are those aforementioned as being suitable for the other preparations. $Na_2CO_3$ and $K_2CO_3$ are particularly suitable. The alkali metal or alkaline earth metal is preferably added in an amount such that the mole ratio of the metal to the rare earth is in the range of about 0.001 to about 1.000, more preferably in the range of about 0.010 to about 0.600, still more preferably in the range of about 0.020 to about 0.300, and most preferably in the range of about 0.040 to about 0.200. Other materials, such as a cerium compound, may also be added.

The catalyst may be formed on or be mixed with a support material. Suitable support materials and supports are those aforementioned as being suitable for the other preparations. The method in which the catalyst is formed on or added to the support material is not critical. The at least one rare earth compound and optionally at least one cocatalyst compound, at least one alkali metal or alkaline earth metal compound, and/or other materials are generally combined with the support material as a solution, dispersion, or suspension prior to and/or during the drying step. The materials may be applied together or sequentially. The material may be dried between applications. One method is to combine the catalyst materials, water, and support material, which may be done before, during, or after the acid treatment but before drying.

The incipient wetness method may be used. Another method is to put the support material into a vessel, fill the vessel with a mixture of treated catalyst materials, drain the liquid, and dry the impregnated support material, which may be repeated. The amount of catalyst applied to the support material is not critical provided that the combination is effective, and the aforementioned amounts may be used.

In the second step, the acid-treated rare earth compound, and optionally other materials, is dried to about a dry state, preferably to a dry state, such that the material does not form a foamed material. The method of drying is not critical to the present invention, and drying methods may be used that are known to one skilled in the art, provided that the material does not foam appreciably during drying. Foaming has been found to be detrimental and to produce catalysts having low selectivity. The material should be dried at least until it is essentially free of liquid and is not a paste. Generally the material is dried at low temperatures of about 70° C. to about 120° C., preferably at about 80° C. to about 110° C. The drying may be done in air, under partial vacuum, or in an inert atmosphere such as nitrogen. The drying may be done under a flowing atmosphere. The drying atmosphere preferably contains a low concentration of carbon dioxide, preferably below about 1%, and most preferably does not exceed atmospheric level of carbon dioxide.

In the third step, the dried material is calcined in a flowing atmosphere that contains oxygen, at a temperature in the range of about 300° C. to about 600° C., such that the catalyst forms a surface area greater than about 20 $m^2/g$. Prior to calcination, if the dried material is not on or mixed with a support material, the dried material is preferably crushed into a finely divided solid or powder. The calcination temperature is preferably in the range of about 350° C. to about 550° C., more preferably in the range of about 400° C. to about 550° C., and most preferably in the range of about 400° C. to about 500° C. The calcination time is not critical, provided that sufficient calcination is achieved and the material is not over calcined.

The calcination time is preferably in the range of about 30 minutes to about 12 hours, more preferably in the range of about 45 minutes to about 8 hours, still more preferably in the range of about 1 hour to about 4 hours, and most preferably in the range of about 1 hour to about 2 hours. Calcination atmospheres that have no oxygen have been found to be detrimental. The calcination atmosphere preferably contains oxygen in the range of about 5% to about 100%, more preferably in the range of about 10% to about 70%, still more preferably in the range of about 15% to about 50%, and most preferably in the range of about the oxygen content of air to about 30%. The atmosphere containing oxygen is preferably inert and is generally air, but it may also be oxygen-enriched air. The catalyst material must be calcined in such manner that the bulk of the calcined material is in effective contact with the atmosphere containing oxygen. A flowing atmosphere, such as flowing air, is necessary to maintain an adequate supply of oxygen, particularly when the catalyst is prepared in bulk. The flow rate of the air is not critical, provided that an adequate oxygen concentration is maintained. Any of the aforementioned methods may be used. Carbon dioxide is detrimental and produces catalysts having lower selectivity. Therefore the calcination atmosphere preferably contains a low concentration of carbon dioxide, preferably below about 1%, and most preferably does not exceed atmospheric level of carbon dioxide.

The method is particularly useful for producing catalysts having a high surface area, which is preferably above about 25 $m^2/g$, more preferably above about 30 $m^2/g$, and most preferably is above about 35 $m^2/g$. When the rare earth element is selected from the group consisting of La, Pr, Nd, Sm, and Eu, the method can also produce catalysts having a porous microstructure that contains pore sizes in the range of about 10 to about 1000 angstroms.

First Process Embodiment

The present invention is directed to a process for the oxidative dehydrogenation of a lower hydrocarbon to form at least one higher hydrocarbon and/or lower olefin, which comprises contacting the lower hydrocarbon with oxygen and a catalyst comprising a nonstoichiometric rare earth oxycarbonate of the formula $M_XC_YO_Z$ having a disordered and/or defect structure, wherein M is at least one rare earth element selected from the group consisting of La, Pr, Nd, Sm, Eu, Gd, Tb, Dy, Ho, Er, and Tm, X=2, Z=3+AY, A is less than about 1.8, and Y is the number of carbon atoms in the oxycarbonate. When used for the oxidative dehydrogenation of a lower hydrocarbon at a pressure above about 100 psig, the catalyst has a selectivity of at least about 40% to at least one higher hydrocarbon and/or lower olefin. The catalyst may further comprise a cocatalyst containing at least one metal selected from the group consisting of V, Nb, Ta, Cr, Mo, W, Mn, Re, Fe, Co, Ni, Cu, Zn, Sn, Pb, Sb, and Bi.

The method of contacting the lower hydrocarbon with oxygen and the catalyst is not critical to the practice of the present invention, and any suitable method may be used which is known to those skilled in the art. The lower hydrocarbon and oxygen are preferably mixed and contacted with the catalyst in a cofeed mode in a reactor suitable for commercial operation, but a sequential mode of operation may be used if desired. The reactor design should minimize void volume outside of the catalyst bed in order to minimize uncatalyzed gas phase reactions. The reactor should allow adequate heat transfer and permit desired temperature control, such as a tubular reactor, fluidized bed reactor, riser reactor, and the like.

The lower hydrocarbon is generally methane, ethane, propane, or butane, but another hydrocarbon may be used. The lower hydrocarbon is preferably methane or ethane, and most preferably is methane. The source of oxygen is not critical and may include any of the oxygen sources discussed above. High-purity oxygen is preferred, but air or oxygen-enriched air may be used. The oxygen level must be maintained sufficiently below the explosive limit to provide safe operation. Generally the oxygen concentration is maintained at about 10% to 13% or lower by volume. Higher oxygen concentration is desirable to increase hydrocarbon conversion and reactor productivity, but lower oxygen concentration may be desirable to increase selectivity.

The mole ratio of lower hydrocarbon to oxygen is preferably in the range of about 4/1 to about 12/1, more preferably in the range of about 5/1 to 9/1. Unlike the prior art, carbon dioxide in the feed has been found to be detrimental and to lower reaction selectivity, so carbon dioxide is preferably at a low level below about 5% by volume, more preferably below about 2%, still more preferably below about 1%, and most preferably below about 0.5%. Furthermore, the catalyst must not be treated with carbon dioxide either before or during processing, because unlike the prior art, carbon dioxide treatment degenerates the catalyst in the present invention instead of regenerating it. Trace quantities of halocarbons may be fed with the hydrocarbon to enhance olefin formation, as is known to one skilled in the art.

The process is preferably conducted at a pressure greater than about 100 psig and a temperature less than about 700°

C. The pressure should be less than about 600 psig, preferably less than about 400 psig, and more preferably less than about 300 psig. The pressure is still more preferably in the range of about 125 psig to about 250 psig. The temperature is preferably in the range of about 300° C. to about 650° C., more preferably in the range of about 400° C. to about 600° C.

Generally a higher flow rate is beneficial because it minimizes uncatalyzed homogeneous reaction. Therefore, a high flow rate is preferably used that is consistent with high oxygen conversion, which is preferably above about 80%, more preferably above about 85%, still more preferably above 90%, and most preferably above about 95%, in order to maximize hydrocarbon conversion. The reactor preferably does not become oxygen depleted to any significant extent.

Second Process Embodiment

The present invention is also directed to a process for the oxidative dehydrogenation of a lower hydrocarbon to form at least one higher hydrocarbon and/or lower olefin, which comprises contacting the lower hydrocarbon with oxygen and a catalyst comprising an oxycarbonate, hydroxycarbonate, and/or carbonate of at least one rare earth element selected from the group consisting of La, Pr, Nd, Sm, Eu, Gd, Tb, Dy, Ho, Er, and Tm. When used for the oxidative dehydrogenation of a lower hydrocarbon, the catalyst exhibits higher selectivity to at least one higher hydrocarbon and/or lower olefin at a pressure above about 100 psig than the catalyst or a precursor of the catalyst exhibits at a pressure in the range of about atmospheric pressure to about 25 psig. When operating at a pressure above about 100 psig, the catalyst has a selectivity of at least about 40%.

As before, the process is preferably conducted at a pressure greater than about 100 psig and a temperature less than about 700° C. The lower hydrocarbon is most preferably methane, and the contacting may be done as aforementioned.

Third Process Embodiment

The present invention is also directed to a process for the oxidative dehydrogenation of a lower hydrocarbon to form at least one higher hydrocarbon and/or lower olefin, which comprises contacting the lower hydrocarbon with oxygen and a catalyst comprising (1) an oxycarbonate, hydroxycarbonate and/or carbonate of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Mn, Re, Fe, Co, Ni, Cu, Zn, Sn, Pb, Sb, and Bi. The catalyst, when used for the oxidative dehydrogenation of said lower hydrocarbon, has a selectivity of at least about 40% to at least one higher hydrocarbon and/or lower olefin.

Fourth Process Embodiment

The present invention is also directed to a process for the oxidative dehydrogenation of a lower hydrocarbon to form at least one higher hydrocarbon and/or lower olefin, which comprises contacting the lower hydrocarbon with oxygen and a catalyst comprising (1) an oxide of at least one rare earth element selected from the group consisting of La, Pr, Nd, Sm, Eu, Gd, Th, Dy, Ho, Er, and Tm; and (2) a cocatalyst including at least one metal selected from the group consisting of V, Nb, Ta, Cr, Mo, W, Re, Fe, Co, and Ni. The catalyst, when used for the oxidative dehydrogenation of the lower hydrocarbon, has a selectivity of at least about 40% to at least one higher hydrocarbon and/or lower olefin. The lower hydrocarbon is most preferably methane, and the contacting may be done as aforementioned.

EXAMPLES

The reactor was a ¼-inch OD 304 stainless steel tube within a Lindberg furnace. The reactor temperature was controlled by Beckman 7200 controllers with thermocouples attached to the reactor wall. Temperature ramping was controlled by a Macintosh computer or set manually. The temperatures given are reactor temperatures, measured by a thermocouple in contact with the tube wall. The reactor was charged with catalyst sandwiched between a combination of quartz wool/quartz chips/quartz wool. Gas composition was measured by gas chromatography. A small volume of nitrogen was included in the methane-oxygen feed as an internal standard. In the catalyst preparation, unless indicated otherwise, the material was dried overnight in a vacuum oven at 100 to 140° C., calcined at atmospheric pressure, and pressed into a pellet under mechanical pressure for 15 minutes. The pellet was then broken, screened to the desired particle size, and loaded into the reactor tube with quartz chips/wool at the ends to hold the catalyst in place.

Example 1

The catalyst precursor was prepared by mixing 8.0 grams of commercial $La_2O_3$ with 50 ml of deionized water. The mixture was then slowly heated with stirring to evaporate most of the water, dried, calcined in air at 400° C. for one hour, pressed, and broken into 14/30 mesh particles. The surface area was 13.9 $m^2/g$. The catalyst precursor (1.0 gram) was placed in a tubular reactor and pressurized to 125 psig by methane and oxygen in a ratio of 9:1 at a flow rate of 500 cc/min and a gas hourly space velocity (GHSV) of 30,000 $hr^{-1}$. It was then heated to 450° C. and held for four hours, during which reaction occurred with low oxygen conversion. The temperature was then repeatedly raised by a 50° C. increment and held for four hours, up to 700° C. The results were:

| Temperature | $C_2 + C_3$ Selectivity | Methane Conversion | Oxygen Conversion |
| --- | --- | --- | --- |
| 450° C. | 0% | 0.3% | 6% |
| 500° C. | 46% | 10% | 100% |
| 550° C. | 46% | 9% | 100% |
| 600° C. | 39 → 32% | 8% | 100% |
| 650° C. | 2% | 5% | 100% |
| 700° C. | 2% | 5% | 100% |

The catalyst had stable selectivity at 500 and 550° C., but selectivity declined during the four hours at 600° C., and the catalyst was unselective at 650 and 700° C. For analysis of the active catalyst, the procedure was then repeated with fresh catalyst precursor, except that the catalyst was cooled down in flowing reaction gases after reacting at 550° C. and analyzed. The surface area was 4.9 $m^2/g$. Elemental analysis (x-ray photoelectron spectroscopy) showed that the catalyst had an oxygen/carbon ratio of 1.9 and an oxygen/lanthanum ratio of 2.84, which is a parameter A value of 0.90.

Example 2

This example is not in accordance with the present invention. Commercial $La_2O_3$ as received, which had a surface area of 1.5 $m^2/g$, was placed in a tubular reactor (1.0 grams) and pressurized to 125 psig by methane and oxygen (9:1) at a flow rate of 500 cc/min and a GHSV of 30,000 $hr^{-1}$. The $La_2O_3$ was then heated to 450° C. and held for four hours. The temperature was then repeatedly raised by a 50°

C. increment and held for four hours, up to 650° C. The results are set forth in Table 1:

TABLE 1

| Temperature | $C_2 + C_3$ Selectivity | Methane Conversion | Oxygen Conversion |
|---|---|---|---|
| 450° C. | 0% | 0.4% | 7% |
| 500° C. | 0% | 0.6% | 10% |
| 550° C. | 0% | 2% | 36% |
| 600° C. | 1% | 5% | 100% |
| 650° C. | 2% | 5% | 100% |

The lanthanum oxide did not give total oxygen conversion until 600° C. and it was unselective for methane coupling at all temperatures.

Example 3

The catalyst precursor was prepared by mixing 60.0 grams of $La_2O_3$ with 100 ml of distilled water. The mixture was then heated slowly to evaporate most of the water, dried, and calcined in air at 800, 1000, or 1200° C. for eight hours. The surface areas were 3.8, 1.1, and 0.2 m$^2$/g, respectively. The catalyst precursor was placed in a tubular reactor (2.0 grams, 10/20 mesh) and pressurized to 125 psig by methane and oxygen (9:1) at a flow rate of 500 cc/min and a GHSV of 15,000 hr$^{-1}$. It was then heated gradually to 550° C. and held for four hours. The temperature was then repeatedly raised by a 50° C. increment and held for four hours, up to 700° C. The results are set forth in Table 2:

TABLE 2

| Calcination Temperature | Reactor Temperature | $C_2 + C_3$ Selectivity | Oxygen Conversion |
|---|---|---|---|
| 800° C. | 550° C. | 2% | — |
| 800° C. | 600° C. | 15% | 100% |
| 800° C. | 650° C. | 45% | 100% |
| 800° C. | 700° C. | 19% | 100% |
| 1000° C. | 550° C. | 1% | — |
| 1000° C. | 600° C. | 2% | — |
| 1000° C. | 650° C. | 5% | 100% |
| 1000° C. | 700° C. | 18% | 100% |
| 1200° C. | 550° C. | 3% | — |
| 1200° C. | 600° C. | 4% | — |
| 1200° C. | 650° C. | 8% | — |
| 1200° C. | 700° C. | 11% | 100% |

The material calcined at 800° C. gave 45% selectivity at a reactor temperature of 650° C. but was unselective at 700° C., in accordance with the present invention. The material calcined at 1000 or 1200° C. was unselective at all the reactor temperatures, and was not in accordance with the present invention.

Example 4

The catalyst precursor was prepared and reacted as in Example 3, except $La(NO_3)_3 \cdot H_2O$ was used. The surface areas were 3.4, 1.5, and 1.0 m$^2$/g, respectively. The results are set forth in Table 3:

TABLE 3

| Calcination Temperature | Reactor Temperature | $C_2 + C_3$ Selectivity | Oxygen Conversion |
|---|---|---|---|
| 800° C. | 550° C. | 3% | — |
| 800° C. | 600° C. | 3% | 100% |

TABLE 3-continued

| Calcination Temperature | Reactor Temperature | $C_2 + C_3$ Selectivity | Oxygen Conversion |
|---|---|---|---|
| 800° C. | 650° C. | 45% | 100% |
| 800° C. | 700° C. | 18% | 100% |
| 1000° C. | 550° C. | 9% | — |
| 1000° C. | 600° C. | 49% | 100% |
| 1000° C. | 650° C. | 39% | 100% |
| 1000° C. | 700° C. | 9% | 100% |
| 1200° C. | 550° C. | 10% | — |
| 1200° C. | 600° C. | 10% | 100% |
| 1200° C. | 650° C. | 16% | 100% |
| 1200° C. | 700° C. | 21% | 100% |

The material calcined at 800° C. gave 45% selectivity at a reactor temperature of 650° C. but was unselective at 700° C., in accordance with the present invention. The material calcined at 1000° C. gave 49% selectivity at a reactor temperature of 600° C. but was unselective at 700° C., in accordance with the present invention. The material calcined at 1200° C. was unselective at all the reactor temperatures, and was not in accordance with the present invention.

Example 5

The catalyst precursor was prepared by precipitating lanthanum hydroxide from a mixture of lanthanum nitrate and ammonium hydroxide in water. The precipitate was then washed to a pH of 8.5, dried, and calcined in air at 650° C. for five hours. The catalyst precursor (1.0 gram, 10/20 mesh) was placed in a tubular reactor and pressurized to 125 psig by methane and oxygen (9:1) at a flow rate of 500 cc/min and a GHSV of 25,000 hr$^{-1}$. It was then slowly heated to 550° C. over a period of two hours and held. The $C_2$ selectivity was 41% and the $C_2+$ selectivity was 43%, with an ethylene/ethane ratio of 0.67, a methane conversion of 10.1%, and an oxygen conversion of 100%. The reactor was then depressurized and the catalyst was purged with flowing carbon dioxide for five hours at 550° C. The reactor was then repressurized and the flow of reactants resumed. The treatment with carbon dioxide substantially reduced the $C_2$ selectivity to 24%, the $C_2+$ selectivity to 25%, and the ethylene/ethane ratio to 0.34, with a lower methane conversion of 8.0% but an oxygen conversion of 100%.

Example 6

This example is not in accordance with the present invention. The catalyst material was prepared and reacted as in Example 5, except the material was calcined in carbon dioxide. This gave a lower $C_2$ selectivity of 33% and $C_2+$ selectivity of 35%, with an ethylene/ethane ratio of 0.59, a methane conversion of 9.6%, and an oxygen conversion of 100%. The catalyst was not stable, and after 40 hours of operation the $C_2$ selectivity had declined to 15%.

Example 7

This example is not in accordance with the present invention. The catalyst material was prepared and reacted as in Example 5, except the material was calcined in carbon dioxide, the flow rate was 700 cc/min, and the reactor was rapidly heated to 600° C. in ten minutes and held. This gave a much lower $C_2$ selectivity of 19% and $C_2+$ selectivity of 20%, with a much lower ethylene/ethane ratio of 0.30, than in Examples 5 and 6, with a methane conversion of 7.2% and an oxygen conversion of 100%.

Example 8

The catalyst precursor was prepared by first dissolving 20.8 grams of $La(NO_3)_3 \cdot 6H_2O$ in 100 ml of methanol and 40 ml of ammonium hydroxide (30% $NH_3$ in $H_2O$) in 20 ml of methanol. The solutions were then mixed dropwise into 30 ml of methanol with stirring. The lanthanum hydroxide precipitate was filtered, washed with methanol, dried, and calcined in air at 700° C. for five hours. The catalyst precursor (0.4 grams, 10/20) was placed in a tubular reactor and pressurized to 125 psig by methane and oxygen (9:1) at a flow rate of 500 cc/min and a GHSV of 43,000 $hr^{-1}$. It was then gradually heated to 450° C. over a period of 1.5 hours and held for four hours. The temperature was then repeatedly ramped upward by a 50° C. increment and held for four hours, up to 600° C. The results are set forth in Table 4:

TABLE 4

| Temperature | $C_2$ Selectivity | $C_2+$ Selectivity | Ethylene/Ethane Ratio | Methane Conversion | Oxygen Conversion |
| --- | --- | --- | --- | --- | --- |
| 450° C. | 39% | 41% | 0.71 | 10.3% | 100% |
| 500° C. | 45% | 48% | 0.82 | 10.9% | 100% |
| 550° C. | 51% | 55% | 0.92 | 11.6% | 100% |
| 600° C. | 49% | 53% | 0.91 | 11.2% | 100% |

The reactor was then depressurized and the catalyst purged with flowing carbon dioxide (500 cc/min) for three hours at 600° C. The reactor was then repressurized and the flow of reactants resumed. The treatment with carbon dioxide substantially reduced the $C_2$ selectivity to 32%, the $C_2+$ selectivity to 34%, and the ethylene/ethane ratio to 0.51, with a lower methane conversion of 9.0% but an oxygen conversion of 100%.

Example 9

The catalyst precursor was prepared by precipitating lanthanum hydroxide from a mixture of lanthanum nitrate and ammonium hydroxide in isopropanol. The precipitate was then washed with water, dried, and calcined in air at 650° C. for five hours. The surface area was 28.6 $m^2/g$. The unpressed catalyst precursor (1.0 gram) was placed in a tubular reactor and pressurized to 125 psig by methane and oxygen (9:1) at a flow rate of 500 cc/min and a GHSV of 33,300 $hr^{-1}$. It was then gradually heated to 450° C. over a period of 1.5 hours and held for four hours. The temperature was then repeatedly ramped upward by a 50° C. increment and held for four hours, up to 600° C. The results are set forth in Table 5:

TABLE 5

| Temperature | $C_2$ Selectivity | $C_2+$ Selectivity | Ethylene/Ethane Ratio | Methane Conversion | Oxygen Conversion |
| --- | --- | --- | --- | --- | --- |
| 450° C. | 17% | 18% | 0.32 | 7.7% | 100% |
| 500° C. | 28% | 29% | 0.45 | 8.4% | 100% |
| 550° C. | 42% | 45% | 0.72 | 9.6% | 100% |
| 600° C. | 50% | 53% | 0.82 | 10.5% | 100% |

Example 10

The catalyst precursor was prepared by mixing 13.3 grams of $La(NO_3)_3 \cdot 6H_2O$ and 27.7 grams of urea in 200 ml of water and heating the mixture to 75° C. and then gradually to 100° C. over four hours, to precipitate lanthanum hydroxide and generate ammonium nitrate and carbon dioxide. The precipitate was washed with water, dried, and calcined in air at 650° C. for five hours. The surface area was 6.2 $m^2/g$. The catalyst precursor (0.8 grams, 10/20 mesh) was placed in a tubular reactor and pressurized to 125 psig by methane and oxygen (9:1) at a flow rate of 500 cc/min and a GHSV of 25,000 $hr^{-1}$. It was then gradually heated to 450° C. over a period of 1.5 hours and held for four hours. The temperature was then repeatedly ramped upward by a 50° C. increment and held for four hours, up to 650° C. The results are set forth in Table 6:

TABLE 6

| Temperature | $C_2$ Selectivity | $C_2+$ Selectivity | Ethylene/Ethane Ratio | Methane Conversion | Oxygen Conversion |
| --- | --- | --- | --- | --- | --- |
| 450° C. | — | — | — | — | 3% |
| 500° C. | — | — | — | — | 10% |
| 550° C. | 19% | 20% | 0.33 | 7.7% | 100% |
| 600° C. | 32% | 35% | 0.56 | 8.7% | 100% |
| 650° C. | 42% | 45% | 0.87 | 9.7% | 100% |

Example 11

This example is not in accordance with the present invention. Commercial lanthanum hydroxide as received was placed in a tubular reactor (0.5 grams) and pressurized to 125 psig by methane and oxygen (9:1) at a flow rate of 500 cc/min and a GHSV of 60,000 $hr^{-1}$. It was then heated to 450° C. and held for four hours. The temperature was then repeatedly raised by a 50° C. increment and held for four hours, up to 650° C. The results are set forth in Table 7:

TABLE 7

| Temperature | $C_2 + C_3$ Selectivity | Methane Conversion | Oxygen Conversion |
| --- | --- | --- | --- |
| 450° C. | 0% | 0% | 2% |
| 500° C. | 0% | 1% | 8% |
| 550° C. | 19% | 7% | 100% |
| 600° C. | 12% | 7% | 100% |
| 650° C. | 9% | 6% | 100% |

Selectivity was low and the ethylene/ethane ratio was 0.2 or lower.

Example 12

The catalyst precursor was prepared by precipitating a mixture of 70% lanthanum hydroxide and 30% cerium hydroxide from a mixture of lanthanum nitrate, cerium nitrate, and ammonium hydroxide in water. The precipitate was washed, dried, and calcined in air at 550° C. for five hours. The catalyst precursor (0.5 gram, 10/20 mesh) was placed in a tubular reactor and pressurized to 125 psig by methane and oxygen (9:1) at a flow rate of 500 cc/min and a GHSV of 30,000 hr$^{-1}$. It was then gradually heated to a temperature of 400° C. over a period of 1.5 hours and held for four hours. The temperature was then repeatedly ramped upward by a 50° C. increment and held for four hours, up to 700° C. The results are set forth in Table 8:

TABLE 8

| Temperature | $C_2$ Selectivity | $C_2$ + Selectivity | Ethylene/ Ethane Ratio | Methane Conversion | Oxygen Conversion |
|---|---|---|---|---|---|
| 400° C. | 36% | 39% | 0.46 | 10.0% | 100% |
| 450° C. | 46% | 49% | 0.59 | 10.8% | 100% |
| 500° C. | 52% | 57% | 0.70 | 11.3% | 100% |
| 550° C. | 55% | 60% | 0.78 | 11.4% | 100% |
| 600° C. | 52% | 56% | 0.74 | 11.0% | 100% |
| 650° C. | 45 → 41% | 49 → 44% | 0.64 → 0.51 | 10.3 → 9.9% | 100% |
| 700° C. | 41 → 18% | 44 → 18% | 0.49 → 0.18 | 9.7 → 7.5% | 100% |

For comparison, the preparation and reaction was repeated by substituting zirconium nitrate for the lanthanum nitrate. The material was unselective (<15%) over the entire temperature range.

Example 13

The catalyst precursor was prepared by precipitating lanthanum oxalate by combining aqueous solutions of lanthanum nitrate and oxalic acid (20% excess). The precipitate was washed with water several times, dried overnight in a vacuum oven at 120° C., and calcined at 550° C. for 4.5 hours in flowing air (200 cc/min). The catalyst precursor (0.5 grams, 10/20 mesh) was placed in a tubular reactor and pressurized to 125 psig by methane and oxygen (9:1) at a flow rate of 500 cc/min and a GHSV of 30,000 hr$^{-1}$. It was then gradually heated to 400° C. over 1.5 hours and held for four hours. The temperature was then repeatedly ramped upward by a 50° C. increment and held for four hours, up to 700° C. The results are set forth in Table 9:

TABLE 9

| Temperature | $C_2$ Selectivity | $C_2$ + Selectivity | Ethylene/ Ethane Ratio | Methane Conversion | Oxygen Conversion |
|---|---|---|---|---|---|
| 400° C. | — | — | — | — | — |
| 450° C. | — | — | — | — | 1% |
| 500° C. | — | — | — | — | 3% |
| 550° C. | — | — | — | 1% | 10% |
| 600° C. | 47% | 51% | 0.94 | 10.9% | 100% |
| 650° C. | 46% | 50% | 0.84 | 10.3% | 100% |

Example 14

The catalyst precursor was lanthanum acetate hydrate, La(CH$_3$COO)$_3$·1.5 H$_2$O, which was used either uncalcined or calcined at temperatures of 400 or 800° C. in flowing air for two hours. The catalyst precursor (14/30 mesh) was placed in a tubular reactor, and pressurized to 125 psig by methane and oxygen (9:1) at a flow rate of 500 cc/min and a GHSV of 30,000 hr$^{-1}$. It was then heated to 450° C. and held for four hours, during which reaction occurred with low oxygen conversion. The temperature was then repeatedly raised by a 50° C. increment and held for four hours, up to 700° C. The results are set forth in Table 10:

TABLE 10

| Calcination Temp. | Initial Selec. | Initial Temp. | Max. $C_2$ + Selec. | Ethylene/ Ethane | Peak Temp. | Catalyst Unselective |
|---|---|---|---|---|---|---|
| None | 36% | 550° C. | 49% | 0.9 | 650° C. | 700° C. |
| 400° C. | 28% | 500° C. | 57% | 1.2 | 650° C. | 700° C. |
| 800° C. | 53% | 500° C. | 55% | 1.1 | 550° C. | 650° C. |

The initial selectivity is the selectivity at the initial temperature at which the catalyst reacted with 100% oxygen conversion. The peak temperature is the temperature of maximum $C_2$+selectivity. The last column is the temperature at which the catalyst became unselective.

Example 15

This example is not in accordance with the present invention. Lanthanum acetate was charged to a tubular reactor and heated at 525° C. for one hour with flowing helium (900 cc/min) at atmospheric pressure. It was then pressurized to 125 psig by methane and oxygen (9:1) at a flow rate of 500 cc/min and heated to 400° C. and held for four hours. The temperature was then repeatedly raised by a 50° C. increment and held for four hours, up to 750° C. The maximum $C_2$ selectivity was 29.6% at a reactor temperature of 700° C., with a methane conversion of 10.0%. For comparison, the catalyst was reacted in the same manner but in a quartz tubular reactor at a low pressure of 15 psig and up to 800° C., which gave a much higher maximum $C_2$ selectivity of 51.1% at 550° C., with a methane conversion of 12.1%.

Example 16

The catalyst precursor was lanthanum carbonate hydrate, La$_2$(CO$_3$)$_3$·8 H$_2$O, which was used either uncalcined or calcined at temperatures of 400, 450, or 500° C. in flowing air for two hours. The catalyst precursor (14/30 mesh) was placed in a tubular reactor and pressurized to 125 psig by methane and oxygen (9:1) at a flow rate of 500 cc/min and a GHSV of 30,000 hr$^{-1}$. It was then heated to 450° C. and held for four hours, during which reaction occurred with low oxygen conversion. The temperature was then repeatedly raised by a 50° C. increment and held for four hours, up to 700° C. The results are set forth in Table 11:

TABLE 11

| Calcination Temp. | Initial $C_2$+ Selec. | Initial Temp. | Max. $C_2$+ Selec | Peak Temp. |
|---|---|---|---|---|
| None | 35% | 500° C. | 49% | 550° C. |
| 400° C. | 48% | 500° C. | 56% | 550° C. |

TABLE 11-continued

| Calcination Temp. | Initial $C_2$+ Selec. | Initial Temp. | Max. $C_2$+ Selec | Peak Temp. |
|---|---|---|---|---|
| 450° C. | 50% | 500° C. | 59% | 550° C. |
| 500° C. | 44% | 500° C. | 52% | 550° C. |

Example 17

The catalyst was prepared by mixing 10.0 grams of $La_2O_3$ in 50 ml of water and adding dropwise a mixture of 10 ml of acetic acid (concentrated) and 10 ml water with active stirring to maintain the pH at about 4 until the pH remained constant at 4 for about five minutes. The mixture was then heated with stirring to evaporate most of the water and dried overnight in a vacuum oven at 80° C. No foamed material was produced. The dry dense-cake material was crushed to a powder and calcined in flowing air at atmospheric pressure at 400° C. for one hour. The catalyst was white in color with a powder density of 0.4 g/ml. The calcined catalyst was pressed and broken into 14/30 mesh particles. The prepared catalyst had a surface area of 35.7 $m^2/g$. Elemental analysis of the catalyst (electron energy loss spectroscopy) gave an oxygen/carbon ratio of 3.15 and an oxygen/lanthanum ratio of 2.39, which is a parameter A value of 1.17. The low-resolution electron microscope micrograph (FIG. 11) shows the highly porous nature of the catalyst, and the high-resolution micrograph (FIG. 12) shows the disordered and porous microstructure. The catalyst (1.0 grams) was then placed in a tubular reactor and pressurized to 125 psig by methane and oxygen (9:1) at a flow rate of 500 cc/min and a GHSV of 30,000 $hr^{-1}$. It was then heated to 400° C. and held for four hours. The temperature was then repeatedly raised by a 50° C. increment and held for four hours, up to 650° C. The results are set forth in Table 12:

TABLE 12

| Temperature | $C_2$ Selectivity | $C_2 + C_3$ Selectivity | Ethylene/Ethane Ratio | Methane Conversion | Oxygen Conversion |
|---|---|---|---|---|---|
| 400° C. | 0% | 0% | — | 0.2% | 4% |
| 450° C. | 37% | 40% | 0.6 | 9% | 100% |
| 500° C. | 40% | 43% | 0.7 | 9% | 100% |
| 550° C. | 54% | 59% | 0.9 | 11% | 100% |
| 600° C. | 54% | 58% | 0.9 | 10% | 100% |
| 650° C. | 52 → 48% | 57 → 51% | 0.8 | 9% | 100% |

The procedure was then repeated with fresh catalyst, except that the catalyst was cooled down after reacting at 500° C. and analyzed. The reacted catalyst had an oxygen/carbon ratio of 3.92 and an oxygen/lanthanum ratio of 2.41, which is a parameter A value of 1.48. The procedure was then repeated again with fresh catalyst, except that the catalyst was cooled down after reacting at 600° C. and analyzed. The reacted catalyst had an oxygen/carbon ratio of 3.25 and an oxygen/lanthanum ratio of 2.30, which is a parameter A value of 1.13.

For comparison, the preparation was repeated except that the catalyst was calcined for 16 hours. Elemental analysis gave an oxygen/carbon ratio of 3.81 and an oxygen/lanthanum ratio of 2.25, which is a parameter A value of 1.27.

Example 18

The same procedures were used as in Example 17, except that the acetic acid was added to hold the pH at about 6. The density of the calcined material was 1.0 g/ml. The results are set forth in Table 13:

TABLE 13

| $C_2$ Temperature | $C_2 + C_3$ Selectivity | Ethylene/Selectivity | Methane Ethane Ratio | Oxygen Conversion | Conversion |
|---|---|---|---|---|---|
| 400° C. | 0% | 0% | — | 0.1% | 1% |
| 450° C. | 0% | 0% | — | 0.5% | 8% |
| 500° C. | 33% | 35% | 0.5 | 8% | 100% |
| 550° C. | 38% | 40% | 0.5 | 8% | 100% |
| 600° C. | 38% | 40% | 0.5 | 8% | 100% |
| 650° C. | 35 → 3% | 37 → 3% | 0.5 → 0.1 | 8 → 1% | 100% |

Example 19

The catalyst was prepared and reacted the same way as in Example 17, except that formic acid was substituted for the acetic acid. The maximum $C_2$ selectivity was 45% at 550° C.

Example 20

This example is not in accordance with the present invention. The catalyst was prepared by first heating at 120° C. (boiling point) a concentrated acetic acid solution containing lanthanum acetate hydrate, $La(CH_3COO)_3·1.5 H_2O$. The solution volume was reduced by boiling off excess water and acetic acid, with vapors removed by aspiration with a water pump. The material was then dried by being heated at 150° C. for 30 minutes under a pressure of 0.1 Pa (vacuum). This produced a foamed material, which was crushed to a fine powder and calcined at 600° C. for 2 hours in air (muffle furnace). The catalyst as prepared had a powder density of 1 $g/cm^3$ and a surface area is 4.34 $m^2/g$. High-resolution electron microscopy showed that it did not have a porous microstructure. The calcined catalyst was pressed and broken into 14/30 mesh particles. The catalyst (0.5 grams) was placed in a tubular reactor and pressurized to 125 psig by methane and oxygen (9:1) at a flow rate of 500 cc/min and a GHSV of 60,000 $hr^{-1}$. It was then heated to 400° C. and held for four hours. The temperature was then repeatedly raised by a 50° C. increment and held for four hours, up to 750° C. The maximum $C_2$ selectivity was 15.4% at 750° C., with a methane conversion of 8.9%. For comparison, the catalyst was reacted in the same manner but in a quartz tubular reactor at a low pressure of 15 psig and up to 800° C., which gave a higher maximum $C_2$ selectivity of 35.8% at a reactor temperature of 550° C., with a methane conversion of 9.3%.

Example 21

The catalyst precursor was prepared by mixing 1.0 gram of NaCl and 8.0 grams of $La_2O_3$ in 50 ml of water. The mixture was then heated with stirring to evaporate most of the water, dried, and calcined in air at 400° C. for one hour. The catalyst precursor (1.0 gram, 14/30 mesh) was placed in a tubular reactor and pressurized to 125 psig by methane and oxygen (9:1) at a flow rate of 500 cc/min and a GHSV of 30,000 $hr^{-1}$. It was then heated to 500° C. and held for four hours, during which reaction occurred with low oxygen conversion. The temperature was then repeatedly raised by a 50° C. increment and held for four hours, up to 700° C. The results are set forth in Table 14:

TABLE 14

| Temperature | C$_2$ + C$_3$ Selectivity | Ethylene/ Ethane Ratio | Methane Conversion | Oxygen Conversion |
|---|---|---|---|---|
| 500° C. | 0% | — | 0.4% | 6% |
| 550° C. | 1% | — | 2% | 20% |
| 600° C. | 65% | 1.1 | 12% | 100% |
| 650° C. | 65% | 1.1 | 12% | 100% |
| 700° C. | 2% | — | 5% | 100% |

For comparison, the procedure was repeated with fresh catalyst precursor but at a low pressure of 25 psig, with a flow rate of 90 cc/min and a GHSV of 5,400 hr$^{-1}$. The results are set forth in Table 15:

TABLE 15

| Temperature | C$_2$ + C$_3$ Selectivity | Ethylene/ Ethane Ratio | Methane Conversion | Oxygen Conversion |
|---|---|---|---|---|
| 500° C. | 1% | — | 2% | 25% |
| 550° C. | 5% | — | 3% | 42% |
| 600° C. | 18% | 0.3 | 5% | 100% |
| 650° C. | 35% | 0.2 | 8% | 100% |
| 700° C. | 49% | 0.3 | 9% | 100% |

The maximum selectivity and ethylene/ethane ratio at low pressure were substantially lower than at elevated pressure.

For comparison, the procedure was repeated substituting MgO for the La$_2$O$_3$. The results are set forth in Table 16:

TABLE 16

| Temperature | C$_2$ + C$_3$ Selectivity | Methane Conversion | Oxygen Conversion |
|---|---|---|---|
| 500° C. | 0% | 0% | 3% |
| 550° C. | 0% | 1% | 8% |
| 600° C. | 2% | 2% | 24% |
| 650° C. | 12% | 5% | 75% |

For another comparison, the procedure was repeated substituting α-alumina for the La$_2$O$_3$. The results are set forth in Table 17:

TABLE 17

| Temperature | C$_2$ + C$_3$ Selectivity | Methane Conversion | Oxygen Conversion |
|---|---|---|---|
| 500° C. | 0% | 0% | 0% |
| 550° C. | 0% | 0% | 1% |
| 600° C. | 4% | 1% | 12% |
| 650° C. | 6% | 3% | 60% |

These materials were unselective for methane coupling.

Example 22

The same catalyst and procedure were used as in Example 21, at 125 psig, except the oxygen content of the mixture of methane and oxygen was increased to a ratio of 5.4:1, at a flow rate of 500 cc/min and a GHSV of 30,000 hr$^{-1}$, and the initial temperature was 450° C. The results are set forth in Table 18:

TABLE 18

| Reactor Temperature | C$_2$ + C$_3$ Selectivity | Ethylene/ Ethane Ratio | Methane Conversion | Oxygen Conversion |
|---|---|---|---|---|
| 500° C. | 53% | 2.2 | 18% | 100% |
| 550° C. | 53% | 2.2 | 18% | 100% |
| 600° C. | 50% | 2.2 | 17% | 100% |
| 650° C. | 49→20% | 2.2→0.5 | 17→12% | 100% |

Selectivity was lower but the ethylene/ethane ratio and methane conversion were higher.

Example 23

The same catalyst and procedure were used as in Example 21, but at a flow rate of 700 cc/min and a GHSV of 42,000 hr$^{-1}$, with reaction maintained for eight days at 500° C. and 125 psig. The C$_2$ selectivity and ethylene/ethane ratio obtained are given in FIG. 10. After the initial loss, the selectivity loss was about 1% per day and the ratio loss was about 3% per day. During the seventh day, both selectivity and ratio were regained (to the levels obtained after the initial loss) by increasing the flow rate to 900 cc/min. Analysis showed that the aged catalyst had a 34% loss of sodium and an 82% loss of chlorine, and that other lanthanides were present in the catalyst precursor, with Gd$_2$O$_3$ (1.7%) being in largest amount, with lesser amounts of Pr$_2$O$_3$, Nd$_2$O$_3$, Eu$_2$O$_3$, and Tb$_2$O$_3$.

Example 24

A variety of catalyst precursors containing an alkali chloride, alkaline earth chloride, or sodium halide was prepared by mixing an amount equimolar to 1.0 gram of NaCl with 8.0 grams of La$_2$O$_3$ in 50 ml of water. The procedure and reaction conditions were then the same as in Example 21, except the temperature range was 450 to 650° C. The maximum C$_2$+C$_3$ selectivity for each compound at 100% oxygen conversion is set forth in Table 19:

TABLE 19

| Compound | Maximum Selectivity |
|---|---|
| LiCl | 8% |
| KCl | 61% |
| RbCl | 40% |
| CsCl | 20% |
| MgCl$_2$ | 41% |
| CaCl$_2$ | 45% |
| SrCl$_2$ | 37% |
| BaCl$_2$ | 35% |
| NaF | 37% |
| NaBr | 63% |
| NaI | 50% |
| None | 46% |

The amounts of these compounds were not individually optimized. However, if the compounds were present in optimized amounts, it is expected that maximum C$_2$+C$_3$ selectivity for all of the above-listed compounds would be at least 40%. Moreover, as noted earlier, Li and Cs are not particularly preferred alkali metals, but may be used in combination with other materials which improve catalyst stability, prolong catalyst life, or provide a lower reaction temperature. Accordingly, if LiCl and CsCl are combined with other cocatalysts, such as W, Pb, Fe, Mn, or Bi, then catalyst systems that provide good results can be obtained.

Example 25

The catalyst precursor was prepared by mixing 1.0 gram of Fe(NO$_3$)$_3$·9H$_2$O and 10.0 grams of La$_2$O$_3$ in 50 ml of water. The mixture was then heated with stirring to evaporate most of the water, dried, and calcined in air at 400° C. for one hour. The surface area was 14.4 m²/g. The catalyst precursor (1.0 gram, 14/30 mesh) was placed in a tubular reactor and pressurized to 125 psig by methane and oxygen (9:1) at a flow rate of 500 cc/min and a GHSV of 30,000 hr⁻¹. It was heated to 500° C. and held for four hours. This gave a constant $C_2+C_3$ selectivity of 66%, an ethylene/ethane ratio of 0.7, a methane conversion of 11%, and an oxygen conversion of 100%. The temperature was then increased to 550° C. for four hours, which gave a selectivity of 63%. The selective catalyst was then cooled and analyzed. The surface area was 7.2 m²/g. Elemental analysis gave an oxygen/carbon ratio of 2.1 and an oxygen/lanthanum ratio of 2.8, which is a parameter A value of 1.0. The procedure was then repeated with fresh catalyst precursor, except that the catalyst was taken to 600° C., which gave a selectivity of 60%. At 650° C., the catalyst became unselective over time, and at 700° C., the catalyst was totally unselective because the temperature was too high.

A second catalyst precursor was then prepared and reacted in the same manner, except that 0.5 grams of $Fe(NO_3)_3 \cdot 9H_2O$ and 8.0 grams of $La_2O_3$ were used, calcination was at 800° C. for six hours, and it was heated to 450° C. in the reactor before the temperature was increased in 10° C. increments to 650° C. The $C_2 + C_3$ selectivity was constant at 57–58% over the temperature range of 450 to 590° C., and then decreased to 37% at 640° C. and 3% at 650° C. (FIG. 17).

Example 26

The catalyst was prepared by the same procedure as in Example 17, except that 1.0 gram of $Fe(NO_3)_3 \cdot 9H_2O$ was added. The prepared catalyst had a surface area of 43.5 m²/g. Elemental analysis gave an oxygen/carbon ratio of 1.9 and an oxygen/lanthanum ratio of 3.1, which is a parameter A value of 0.97. The catalyst (1.0 gram, 14/30 mesh) was placed in a tubular reactor and pressurized to 125 psig by methane and oxygen (9:1) at a flow rate of 500 cc/min and a GHSV of 30,000 hr⁻¹. It was then heated to 500° C. and held for four hours. This gave a $C_2+C_3$ selectivity of 64%, an ethylene/ethane ratio of 0.7, a methane conversion of 11%, and an oxygen conversion of 100%. The temperature was then increased to 550° C. for four hours, which gave a selectivity of 60%. The catalyst was then cooled and analyzed. The surface area was 10.4 m²/g. The oxygen/carbon ratio was 1.9 and the oxygen/lanthanum ratio was 3.2, which is a parameter A value of 1.00. The procedure was then repeated with fresh catalyst, except the catalyst was taken to 600° C., which gave a selectivity of 57%. At 650° C., the catalyst became unselective over time, and at 700° C., the catalyst was totally unselective because the temperature was too high.

Example 27

The catalyst was prepared and tested the same way as in Example 19, except that 1.0 gram of $Fe(NO_3)_3 \cdot 9H_2O$ was added to the $La_2O_3$. The maximum $C_2$ selectivity was 62% at 450° C.

Example 28

The catalyst was prepared by mixing 1.0 gram of $Fe(NO_3)_3 \cdot 9H_2O$, 0.25 grams of $Na_2CO_3$, and 8.0 grams of $La_2O_3$ in 50 ml of water and following the procedure of Example 17. The catalyst (0.5 grams, 14/30 mesh) was placed in a tubular reactor and pressurized to 125 psig by methane and oxygen (9:1) at a flow rate of 700 cc/min and a GHSV of 84,000 hr⁻¹. The catalyst was gradually heated to 500° C. and held for two days, during which the $C_2$ selectivity decreased from 60 to 56%. The temperature was then increased to 575° C., which increased the selectivity to 62%, and held for thirteen days. It was then increased to 600° C., which did not change the selectivity, and held for fifteen days. During the 30-day run (FIG. 8), the $C_2$ selectivity dropped to a steady level of about 54%, with a steady methane conversion of 10–12% and a steady ethylene/ethane ratio of about 0.93.

Example 29

The catalyst was the same as in Example 28. The catalyst (0.5 grams) was placed in a ¼-inch OD tubular reactor and pressurized to 125 psig by methane and oxygen (9:1) at a flow rate of 500 cc/min and a GHSV of 60,000 hr⁻¹. It was then heated to 400° C. and held for four hours. The temperature was then repeatedly raised by a 50° C. increment and held for four hours, up to 750° C. The maximum $C_2$ selectivity was 61.2% at 500° C., with a methane conversion of 12.4%. For comparison, the catalyst was reacted in the same manner but in a quartz tubular reactor at a low pressure of 15 psig and up to 800° C., which gave a lower maximum $C_2$ selectivity of 53.9% at 650° C., with a methane conversion of 10.8%.

Example 30

The same catalyst and procedures were used as in Example 29, except that a mixture of methane, oxygen, and carbon dioxide in a ratio of 9:1:1 was used at a pressure of 125 psig. The $C_2$ selectivity was 52% at 500° C., with an ethylene/ethane ratio of 1.2. The catalyst became unselective at 650° C. The carbon dioxide decreased the selectivity.

Example 31

The catalyst precursor was prepared by mixing 1.0 gram of $Fe(NO_3)_3 \cdot 9H_2O$, 0.25 grams of $Na_2CO_3$, and 16.8 grams of $La(CH_3COO)_3 \cdot 1.5\ H_2O$ in 50 ml of water. The mixture was then heated with stirring to evaporate most of the water, dried, and calcined in flowing air at 400° C. for one hour. The catalyst (0.5 grams, 14/30 mesh) was placed in a tubular reactor and pressurized to 125 psig by methane and oxygen (9:1) at a flow rate of 500 cc/min and a GHSV of 60,000 hr⁻¹. It was then heated to 400° C. and held for four hours. The temperature was then repeatedly raised by a 50° C. increment and held for four hours, up to 700° C. The maximum $C_2$ selectivity was 58.5% at 600° C.

Example 32

The catalyst precursor was prepared by mixing 1.0 gram of $Fe(NO_3)_3 \cdot 9H_2O$, 0.25 grams of $Na_2CO_3$, and 14.8 grams of $La_2(CO_3)_3 \cdot 8\ H_2O$ in 50 ml of water. The same procedures were then used as in Example 31. The maximum $C_2$ selectivity was 58.5% at a temperature of 600° C.

Example 33

A variety of catalysts were prepared by mixing 1.0 gram of the nitrates of either Pb, V, Re, W, Mn, or Cu and 8.0 grams of $La_2O_3$ in 50 ml of water and then following the acetic acid treatment and procedures of Example 17. The results obtained are set forth in Table 20:

TABLE 20

| Cocatalyst Metal | Maximum $C_2 + C_3$ Selectivity | Peak Temperature |
|---|---|---|
| Pb | 61% | 450° C. |
| V | 47% | 500° C. |
| Re | 41% | 550° C. |
| W | 56% | 550° C. |
| Mn | 57% | 550° C. |
| Cu | 48% | 500° C. |

The amounts were not individually optimized.

Example 34

Catalyst precursor A was prepared by mixing 1.0 gram of $MnMoO_4$ and 8.0 grams of $La_2O_3$ in 50 ml of water. The mixture was then slowly heated with stirring to evaporate most of the water, dried, and calcined in air at 400° C. for one hour. Catalyst precursor B was prepared in the same manner but with 1.0 gram of sodium nitrate added. The catalyst precursor (1.0 gram, 14/30 mesh) was placed in a tubular reactor and pressurized to 125 psig by methane and oxygen (9:1) at a flow rate of 500 cc/min and a GHSV of 30,000 $hr^{-1}$. It was then heated to 450° C. and held for four hours. The temperature was then repeatedly raised by a 50° C. increment and held for four hours, up to 650° C. The results are set forth in Table 21:

TABLE 21

| Catalyst Precursor | Temperature | $C_2 + C_3$ Selectivity | Methane Conversion | Oxygen Conversion |
|---|---|---|---|---|
| A | 450° C. | 52% | 10% | 100% |
| A | 500° C. | 54% | 10% | 100% |
| A | 550° C. | 51% | 10% | 100% |
| A | 600° C. | 41→8% | 8→5% | 100% |
| A | 650° C. | 2% | 5% | 100% |
| B | 450° C. | 0% | 0% | 3% |
| B | 500° C. | 1% | 0% | 8% |
| B | 550° C. | 1% | 1% | 11% |
| B | 600° C. | 58→48% | 8→7% | 100% |
| B | 650° C. | 54→2% | 8→5% | 100% |

Example 35

Catalyst precursors A and B were prepared and reacted in the same manner as in Example 34, except that 1.0 gram of $MnWO_4$ was used instead of $MnMoO_4$. The results are set forth in Table 22:

TABLE 22

| Catalyst Precursor | Temperature | $C_2 + C_3$ Selectivity | Methane Conversion | Oxygen Conversion |
|---|---|---|---|---|
| A | 450° C. | 38→40% | 9% | 100% |
| A | 500° C. | 44% | 9% | 100% |
| A | 550° C. | 50% | 10% | 100% |
| A | 600° C. | 50→45% | 9% | 100% |
| A | 650° C. | 36→2% | 8→5% | 100% |
| B | 450° C. | 0% | 0% | 3% |
| B | 500° C. | 0% | 0% | 8% |
| B | 550° C. | 62% | 10% | 100% |
| B | 600° C. | 58→40% | 10→8% | 100% |
| B | 650° C. | 2% | 5% | 100% |

Example 36

The catalyst precursor (F) was prepared by dissolving 0.34 grams of ammonium tungstate, 0.99 grams of $Mn(NO_3)_2 \cdot 6H_2O$, and 0.21 grams of sodium nitrate in 50 ml of water and adding 8.6 grams of $La_2O_3$. The mixture was then slowly heated with stirring to evaporate most of the water, dried, and calcined in air at 800° C. for six hours. The procedure was repeated with either a 50% higher (B) or 50% lower (J) amount of cocatalyst materials. The catalyst precursor (2.0 grams, 14/30 mesh) was placed in a tubular reactor and pressurized to 125 psig by methane and oxygen (9:1) at a flow rate of 500 cc/min and a GHSV of 15,000 $hr^{-1}$. It was then heated to 450° C. and held for four hours. The temperature was then repeatedly raised by a 50° C. increment and held for four hours, up to 650° C. The results are set forth in Table 23:

TABLE 23

| Catalyst Precursor | Temperature | $C_2 + C_3$ Selectivity | Methane Conversion | Oxygen Conversion |
|---|---|---|---|---|
| F | 450° C. | 65% | 11% | 100% |
| F | 500° C. | 66% | 11% | 100% |
| F | 550° C. | 65% | 11% | 100% |
| F | 600° C. | 62→42% | 10→8% | 100% |
| F | 650° C. | 3% | 5% | 100% |
| B | 450° C. | 39% | 7% | 100% |
| B | 500° C. | 37% | 7% | 100% |
| B | 550° C. | 61% | 10% | 100% |
| B | 600° C. | 61→33% | 10→7% | 100% |
| B | 650° C. | 4% | — | 100% |
| J | 450° C. | — | — | 9% |
| J | 500° C. | 64% | 11% | 100% |
| J | 550° C. | 62% | 11% | 100% |
| J | 600° C. | 57→47% | 10→7 % | 100% |
| J | 650° C. | 3% | 5% | 100% |

The preparation of catalyst precursor (F) was repeated except that calcination was at 400° C. The reaction was done in the same manner except that the methane:oxygen ratio was 8.5:1 and the initial temperature was 400° C. The results are set forth in Table 24:

TABLE 24

| Temperature | $C_2$ Selectivity | $C_2 +$ Selectivity | Ethylene/ Ethane Ratio | Methane Conversion | Oxygen Conversion |
|---|---|---|---|---|---|
| 400° C. | 61% | 67% | 0.72 | 13.7% | 100% |
| 450° C. | 62% | 67% | 0.75 | 13.7% | 100% |
| 500° C. | 61% | 66% | 0.80 | 13.8% | 100% |
| 550° C. | 60% | 65% | 0.82 | 13.5% | 100% |
| 600° C. | 56% | 61% | 0.71 | 12.6% | 100% |
| 650° C. | 8% | 8% | 0.09 | 6.4% | 100% |

Example 37

This example is not in accordance with the present invention. The catalyst was prepared by dissolving 0.4 grams of $Na_2WO_4 \cdot 2H_2O$ and 0.99 grams of $Mn(NO_3)_2 \cdot 6H_2O$ in 50 ml of water and adding 8.6 grams of $TiO_2$. The mixture was then slowly heated with stirring to evaporate most of the water, dried, and calcined in air at either 400° C. for one hour or 800° C. for six hours. The catalyst (1.0 gram, 14/30 mesh) was placed in a tubular reactor and pressurized to 125 psig by methane and oxygen (9:1) at a flow rate of 500 cc/min and a GHSV of 30,000 $hr^{-1}$. It was then heated to 450° C. and held for four hours. The temperature was then repeatedly ramped upward by a 50° C. increment and held for four hours, up to 600° C. The catalyst calcined at 800° C. was unselective (<5%) at all temperatures. The catalyst calcined at 400° C. was unstable because the initial selectivity decreased rapidly over four hours at all temperatures. The results are set forth in Table 25:

TABLE 25

| Reactor Temperature | $C_2 + C_3$ Selectivity | Ethylene/ Ethane Ratio | Methane Conversion | Oxygen Conversion |
|---|---|---|---|---|
| 450° C. | 13→4% | 0.14→0.06 | 5.4→4.7% | 100% |
| 500° C. | 26→11% | 0.32→0.13 | 6.1→5.2% | 100% |
| 550° C. | 38→22% | 0.39→0.24 | 7.2→6.0% | 100% |
| 600° C. | 50→35% | 0.52→0.37 | 8.5→6.8% | 100% |

Example 38

This example is not in accordance with the present invention. The catalyst was prepared in the same manner as Example 37, except that MgO was used instead of $TiO_2$, with calcination at 800° C. The catalyst (2.0 grams) was placed in a tubular reactor and pressurized to 125 psig by methane and oxygen (9:1) at a flow rate of 300 cc/min. It was then heated to 675° C., the temperature that gave maximum selectivity, and held. The catalyst was unstable and the $C_2+$ selectivity fell approximately linearly with time from 55% to 35% after 11 hours and to 7% after 22 hours. The ethylene/ethane ratio fell from 0.63 to 0.35 after 11 hours and to 0.08 after 22 hours.

Example 39

The catalyst precursor was prepared by mixing 8.6 grams of $La_2O_3$ in 50 ml of water and adding 25% aqueous acetic acid dropwise with active stirring to maintain the pH at about 4 until the pH remained constant at 4 for about five minutes. Then 0.4 grams of $Na_2WO_4 \cdot 2H_2O$ and 1.0 gram of $Mn(NO_3)_3 \cdot 6H_2O$ were added and the mixture was heated to evaporate most of the water, dried, and calcined at 600° C. for five hours under flowing air (200 cc/min). The catalyst precursor (0.5 gram, 10/20 mesh) was placed in a tubular reactor and pressurized to 125 psig by methane and oxygen (9:1) at a flow rate of 500 cc/min and a GHSV of 30,000 $hr^{-1}$. It was then gradually heated to 450° C. over 1.5 hours and held for three hours. The temperature was then increased to 500° C. and held. The $C_2$ selectivity was 54% and the $C_2+$ selectivity was 59%, with an ethylene/ethane ratio of 0.74, a methane conversion of 11.7%, and an oxygen conversion of 100%. Fresh catalyst precursor was then gradually heated to a temperature of 200° C. over 1.5 hours and held for three hours. The temperature was then repeatedly raised by a 50° C. increment and held for three hours, up to 500° C. The long heat up time of about 20 hours gave a higher $C_2$ selectivity of 60% and $C_2+$ selectivity of 67%, and a higher ethylene/ethane ratio of 1.02, with a methane conversion of 12.7% and an oxygen conversion of 100%.

Example 40

Catalyst precursor A was prepared by dissolving 0.4 grams of $Na_2CrO_4 \cdot 4H_2O$ and 0.99 grams of $Mn(NO_3)_2 \cdot 6H_2O$ in 50 ml of water and adding 8.6 grams of $La_2O_3$. The mixture was heated to evaporate most of the water, dried, and calcined in air at either 400° C. for one hour or 800° C. for six hours. Catalyst precursor B was prepared in the same manner but with the manganese nitrate omitted. The catalyst precursor (1.0 gram, 14/30 mesh) was placed in a tubular reactor and pressurized to 125 psig by methane and oxygen (9:1) at a flow rate of 500 cc/min and a GHSV of 30,000 $hr^{-1}$. It was then heated to 450° C. and held for four hours. The temperature was then repeatedly raised by a 50° C. increment and held for four hours, up to 650° C. The results are set forth in Table 26:

TABLE 26

| Catalyst Precursor | Calcination Temperature | Reactor Temperature | $C_2 + C_3$ Selectivity | Methane Conversion | Oxygen Conversion |
|---|---|---|---|---|---|
| A | 400° C. | 450° C. | 41% | 8% | 100% |
| A | 400° C. | 500° C. | 49% | 8% | 100% |
| A | 400° C. | 550° C. | 52% | 9% | 100% |
| A | 400° C. | 600° C. | 44 → 21% | 8 → 6% | 100% |
| A | 400° C. | 650° C. | 3% | 5% | 100% |
| A | 800° C. | 450° C. | 44% | 8% | 100% |
| A | 800° C. | 500° C. | 51% | 8% | 100% |
| A | 800° C. | 550° C. | 56% | 9% | 100% |
| A | 800° C. | 600° C. | 54% | 9% | 100% |
| A | 800° C. | 650° C. | 36 → 3% | 7 → 5% | 100% |
| B | 400° C. | 450° C. | 0% | 0% | 3% |
| B | 400° C. | 500° C. | 0% | 1% | 17% |
| B | 400° C. | 550° C. | 42% | 8% | 100% |
| B | 400° C. | 600° C. | 44% | 9% | 100% |
| B | 400° C. | 650° C. | 44 → 2% | 9 → 5% | 100% |
| B | 800° C. | 450° C. | 0% | 0% | 2% |
| B | 800° C. | 500° C. | 0% | 1% | 10% |
| B | 800° C. | 550° C. | 27% | 7% | 100% |
| B | 800° C. | 600° C. | 31 → 22% | 7% | 100% |
| B | 800° C. | 650° C. | 1% | 5% | 100% |

For comparison, catalyst precursor (A) was prepared and tested in the same manner, but with $\alpha$-$Al_2O_3$ substituted for the $La_2O_3$. The catalyst was unselective under pressure (<15%) at all temperatures.

Example 41

A series of catalyst precursors was prepared using different cocatalysts and amounts in a modified 5×5 Latin Square design. The design used the metals Mn, Fe, Co, Pb, and Sn (five levels); the alkalis Li, Na, K, Rb, Cs (five levels); the alkaline earths Mg, Ca, Sr, Ba, and Zn (three levels); and the anions $PO_4$, Cl, $SO_4$, $WO_4$, and $ReO_4$ (three levels). The metal levels were: 0.0002 (1), 0.0011 (2), 0.0020 (3), 0.0029 (4), 0.0038 (5) moles. The alkali levels were: 0.00036 (1), 0.00198 (2), 0.00360 (3), 0.00522 (4), 0.00684 (5) moles. The alkaline earth levels were: 0.0009 (−1), 0.0018 (0), 0.0027 (1) moles. The anion levels were: 0.0009 (−1), 0.0018 (0), 0.0027 (1) moles. The numbers in parentheses are the codes for the levels of each cocatalyst. The compositions are given in the table. The metals, alkalis, and alkaline earths were added as nitrates and the anions were added as ammonium salts. The materials of each composition were mixed with 10.0 grams of $La_2O_3$ and 50 ml of water. The mixture was then slowly heated with stirring to evaporate most of the water, dried, and calcined in air (muffle furnace) at 650° C. for 6–8 hours. The catalyst precursor (2.0 grams, 10/20 mesh) was placed in a tubular reactor and pressurized to 125 psig by methane and oxygen (9:1) at a flow rate of 300 cc/min and a GHSV of 9,000 $hr^{-1}$. It was then gradually heated to 500° C. over a period of 1.5 hours and held for four hours. The temperature was then repeatedly ramped upward by a 50° C. increment over 30 minutes and held for four hours, up to 650° C. The maximum $C_2$ selectivity (%), ethylene/ethane ratio, and peak temperature (° C.) at which the maximum selectivity occurred for each case are in the table. Higher metal loading improved ethylene selectivity and total $C_2$ selectivity, whereas alkali, alkaline earth, and anion loadings show no correlation, as set forth in Table 27:

TABLE 27

|    | Mn | Fe | Co | Pb | Sn |
|----|----|----|----|----|----|
| Li | Mn (1)<br>Li (1)<br>Zn (1)<br>PO$_4$ (1)<br>35%<br>0.53<br>650° C. | Fe (4)<br>Li (5)<br>Mg (1)<br>Cl (1)<br>49%<br>0.75<br>650° C. | Co (2)<br>Li (4)<br>Ca (1)<br>SO$_4$ (1)<br>36%<br>0.66<br>650° C. | Pb (5)<br>Li (3)<br>Sr (1)<br>WO$_4$ (1)<br>54%<br>0.74<br>600° C. | Sn (3)<br>Li (2)<br>Ba (1)<br>ReO$_4$ (1)<br>53%<br>0.81<br>600° C. |
| Na | Mn (2)<br>Na (2)<br>Mg (1)<br>WO$_4$ (1)<br>43%<br>0.67<br>650° C. | Fe (5)<br>Na (1)<br>Ca (1)<br>ReO$_4$ (−1)<br>50%<br>0.76<br>600° C. | Co (3)<br>Na (5)<br>Sr (1)<br>PO$_4$ (−1)<br>37%<br>0.56<br>650° C. | Pb (1)<br>Na (4)<br>Ba (1)<br>Cl (−1)<br>26%<br>0.58<br>700° C. | Sn (4)<br>Na (3)<br>Zn (1)<br>SO$_4$ (−1)<br>34%<br>0.61<br>650° C. |
| K  | Mn (3)<br>K (3)<br>Ca (1)<br>Cl (−1)<br>47%<br>0.66<br>650° C. | Fe (1)<br>K (2)<br>Sr (1)<br>SO$_4$ (−1)<br>53%<br>0.77<br>650° C. | Co (4)<br>K (1)<br>Ba (0)<br>WO$_4$ (0)<br>36%<br>0.42<br>600° C. | Pb (2)<br>K (5)<br>Zn (−1)<br>ReO$_4$ (1)<br>49%<br>0.95<br>650° C. | Sn (5)<br>K (4)<br>Mg (−1)<br>PO$_4$ (1)<br>50%<br>0.90<br>600° C. |
| Rb | Mn (4)<br>Rb (4)<br>Sr (−1)<br>ReO$_4$ (1)<br>43%<br>0.60<br>650° C. | Fe (2)<br>Rb (3)<br>Ba (−1)<br>PO$_4$ (1)<br>42%<br>0.60<br>650° C. | Co (5)<br>Rb (2)<br>Zn (−1)<br>Cl (1)<br>44%<br>0.61<br>650° C. | Pb (3)<br>Rb (1)<br>Mg (−1)<br>SO$_4$ (1)<br>52%<br>0.64<br>550° C. | Sn (1)<br>Rb (5)<br>Ca (−1)<br>WO$_4$ (−1)<br>41%<br>0.67<br>650° C. |
| Cs | Mn (5)<br>Cs (5)<br>Ba (−1)<br>SO$_4$ (−1)<br>48%<br>0.83<br>650° C. | Fe (3)<br>Cs (4)<br>Zn (−1)<br>WO$_4$ (−1)<br>54%<br>0.84<br>650° C. | Co (1)<br>Cs (3)<br>Mg (−1)<br>ReO$_4$ (−1)<br>42%<br>0.52<br>600° C. | Pb (4)<br>Cs (2)<br>Ca (−1)<br>PO$_4$ (−1)<br>49%<br>0.68<br>600° C. | Sn (2)<br>Cs (1)<br>Sr (−1)<br>Cl (−1)<br>40%<br>0.65<br>650° C. |

TABLE 28

|    | Bi | Sb | V | Cr | Ni |
|----|----|----|----|----|----|
| Li | Bi (1)<br>Fe<br>Li<br>ZrO$_3$ (1)<br>52%<br>0.66<br>550° C. | Sb (4)<br>Mn<br>Li<br>TaO$_3$ (5)<br>53%<br>0.70<br>550° C. | V (2)<br>Sr<br>Li<br>MoO$_4$ (4)<br>8%<br>0.00<br>600° C. | Cr (5)<br>Mg<br>Li<br>NbO$_3$ (3)<br>46%<br>0.76<br>550° C. | Ni (3)<br>Ba<br>Li<br>ReO$_4$ (2)<br>23%<br>0.00<br>550° C. |
| Na | Bi (2)<br>Mn<br>Na<br>NbO$_3$ (2)<br>57%<br>0.75<br>500° C. | Sb (5)<br>Sr<br>Na<br>ReO$_4$ (1)<br>60%<br>0.92<br>500° C. | V (3)<br>Mg<br>Na<br>ZrO$_3$ (5)<br>26%<br>0.37<br>650° C. | Cr (1)<br>Ba<br>Na<br>TaO$_3$ (4)<br>30%<br>0.59<br>550° C. | Ni (4)<br>Fe<br>Na<br>MoO$_4$ (3)<br>30%<br>0.30<br>550° C. |
| K  | Bi (3)<br>Sr<br>K<br>TaO$_3$ (3)<br>53%<br>0.89<br>550° C. | Sb (1)<br>Mg<br>K<br>MoO$_4$ (2)<br>44%<br>0.50<br>500° C. | V (4)<br>Ba<br>K<br>NbO$_3$ (1)<br>49%<br>0.94<br>500° C. | Cr (2)<br>Fe<br>K<br>ReO$_4$ (5)<br>56%<br>0.87<br>500° C. | Ni (5)<br>Mn<br>K<br>ZrO$_3$ (4)<br>53%<br>1.12<br>550° C. |
| Rb | Bi (4)<br>Mg<br>Rb<br>ReO$_4$ (4)<br>56%<br>0.83<br>500° C. | Sb (2)<br>Ba<br>Rb<br>ZrO$_3$ (3)<br>10%<br>0.09<br>600° C. | V (5)<br>Fe<br>Rb<br>TaO$_3$ (2)<br>55%<br>0.92<br>500° C. | Cr (3)<br>Mn<br>Rb<br>MoO$_4$ (1)<br>50%<br>0.71<br>550° C. | Ni (1)<br>Sr<br>Rb<br>NbO$_3$ (5)<br>44%<br>0.62<br>600° C. |
| Cs | Bi (5)<br>Ba<br>Cs<br>MoO$_4$ (5)<br>52%<br>0.85<br>500° C. | Sb (3)<br>Fe<br>Cs<br>NbO$_3$ (4)<br>57%<br>0.98<br>500° C. | V (1)<br>Mn<br>Cs<br>ReO$_4$ (3)<br>57%<br>0.71<br>500° C. | Cr (4)<br>Sr<br>Cs<br>ZrO$_3$ (2)<br>39%<br>0.79<br>600° C. | Ni (2)<br>Mg<br>Cs<br>TaO$_3$ (1)<br>40%<br>0.65<br>500° C. |

Example 42

A series of catalyst precursors was prepared using different cocatalysts and amounts in a modified 5×5 Latin Square design. The design used the first metals Bi, Sb, V, Cr, and Ni (five levels); the second metals Fe, Mn, Sr, Mg, and Ba (one level), the alkalis Li, Na, K, Rb, Cs (one level); and the polyatomic ions ZrO$_3$, NbO$_3$, TaO$_3$, ReO$_4$, and MoO$_4$ (five levels). The first metal levels were: 0.0002 (1), 0.0011 (2), 0.0020 (3), 0.0029 (4), 0.0038 (5) moles. The second metal level was 0.0040 moles. The alkali level was 0.0080 moles. The ion levels were: 0.0009 (1), 0.0018 (2), 0.0027 (3), 0.0036 (4), and 0.0045 (5) moles. The designed set compositions are in the table. The metals and alkalis were added as nitrates. The ions ZrO$_3$, NbO$_3$, and TaO$_3$ were added as sodium salts and ReO$_4$ and MoO$_4$ as ammonium salts. The materials of each composition were mixed with 10.0 grams of La$_2$O$_3$ and 50 ml of water. The aqueous mixture was then slowly heated with stirring to evaporate most of the water, dried, and calcined in air at 800° C. for six hours. The catalyst precursor (2.0 grams, 10/20 mesh) was placed in a tubular reactor and pressurized to 125 psig by methane and oxygen (9:1) at a flow rate of 500 cc/min and a GHSV of 15,000 hr$^{-1}$. It was then gradually heated to 500° C. over 1.5 hours and held for four hours. The temperature was then repeatedly ramped upward by a 50° C. increment over 30 minutes and held for four hours, up to 650° C. The maximum C$_2$ selectivity (%), ethylene/ethane ratio, and peak temperature (° C.) for each case are set forth in the table 28:

Example 43

The catalyst precursor was prepared by mixing 1.13 grams of NaTaO$_3$, 0.42 grams of Sb$_2$O$_3$, 1.15 grams of Mn(NO$_3$)$_2$·6H$_2$O, and 0.55 grams of LiNO$_3$ with 70 ml of water and adding 10.0 grams of La$_2$O$_3$. The mixture was then slowly heated with stirring to evaporate the water until a paste remained and calcined in flowing air at 800° C. for four hours. The catalyst precursor (0.5 grams, 10–20 mesh) was placed in a tubular reactor and pressurized to 125 psig by methane and oxygen (9:1) at a flow rate of 700 cc/min and a GHSV of 84,000 hr$^{-1}$. It was then gradually heated to 500° C. over 1.5 hours and held for two days, during which the C$_2$ selectivity decreased from 60 to 48%. The temperature was then increased to 575° C., which increased the selectivity back to 60%, and held for thirteen days. It was then increased to 600° C., which did not change the selectivity, and held for fifteen days. During the 30-day run (FIG. 7), the C$_2$ selectivity dropped to a steady level of about 54%, with a steady methane conversion of about 10% and a steady ethylene/ethane ratio of about 0.74.

Example 44

A series of catalyst precursors was prepared using different amounts of iron nitrate, potassium nitrate, magnesium nitrate, and ammonium rhenate in a 5×5 Latin Square design. The amounts used (moles) are in the table. The materials of each composition were mixed with 10.0 grams of either La$_2$O$_3$ or La(NO$_3$)$_3$, or a 50/50 mixture of both, and 50 ml of water. The aqueous mixture was then slowly heated with stirring to evaporate most of the water, dried, and calcined in air at 800° C. for six hours. The catalyst precursor (2.0 grams, 10/20 mesh) was placed in a tubular reactor and pressurized to 125 psig by methane and oxygen (9:1) at a flow rate of 500 cc/min and a GHSV of 15,000 hr$^{-1}$. It was then gradually heated to 500° C. over 1.5 hours and held for four hours. The temperature was then repeatedly ramped upward by a 50° C. increment and held for four hours, up to 650° C. The maximum $C_2$ selectivity, ethylene/ethane ratio, and peak temperature for each case are set forth in Table 29:

TABLE 29

| Base | Run | K | Fe | ReO$_4$ | Mg | $C_2$ Selectivity | Ethylene/Ethane | Peak Temperature |
|---|---|---|---|---|---|---|---|---|
| Oxide | 5 | 0.0156 | 0.0029 | 0.0054 | 0.0054 | 57% | 0.95 | 500° C. |
| Oxide | 14 | 0.0052 | 0.0029 | 0.0054 | 0.0018 | 56% | 0.79 | 500° C. |
| Oxide | 2 | 0.0156 | 0.0087 | 0.0054 | 0.0018 | 53% | 0.89 | 550° C. |
| Oxide | 9 | 0.0052 | 0.0087 | 0.0054 | 0.0054 | 53% | 0.66 | 550° C. |
| Oxide | 12 | 0.0052 | 0.0087 | 0.0018 | 0.0018 | 53% | 0.71 | 500° C. |
| Oxide | 3 | 0.0156 | 0.0087 | 0.0018 | 0.0054 | 49% | 0.81 | 550° C. |
| Oxide | 15 | 0.0052 | 0.0029 | 0.0018 | 0.0054 | 48% | 0.64 | 500° C. |
| Oxide | 8 | 0.0156 | 0.0029 | 0.0018 | 0.0018 | 47% | 0.75 | 500° C. |
| Nitrate | 13 | 0.0052 | 0.0029 | 0.0054 | 0.0054 | 56% | 0.77 | 500° C. |
| Nitrate | 7 | 0.0156 | 0.0029 | 0.0018 | 0.0054 | 55% | 0.93 | 550° C. |
| Nitrate | 4 | 0.0156 | 0.0087 | 0.0018 | 0.0018 | 54% | 0.86 | 550° C. |
| Nitrate | 10 | 0.0052 | 0.0087 | 0.0054 | 0.0018 | 52% | 0.65 | 550° C. |
| Nitrate | 1 | 0.0156 | 0.0087 | 0.0054 | 0.0054 | 50% | 0.79 | 550° C. |
| Nitrate | 16 | 0.0052 | 0.0029 | 0.0018 | 0.0018 | 48% | 0.75 | 550° C. |
| Nitrate | 11 | 0.0052 | 0.0087 | 0.0018 | 0.0054 | 46% | 0.65 | 500° C. |
| Nitrate | 6 | 0.0156 | 0.0029 | 0.0054 | 0.0018 | 43% | 0.61 | 550° C. |
| 50/50 | CP | 0.0104 | 0.0058 | 0.0036 | 0.0036 | 56% | 0.78 | 500° C. |

Example 45

A series of catalyst precursors was prepared using different amounts of manganese nitrate hexahydrate, potassium nitrate, bismuth nitrate pentahydrate, and sodium niobate in a 5×5 Latin Square design. The amounts used (moles) are in the table. The materials of each composition were mixed with 10.0 grams of $La_2O_3$ and 50 ml of water. The compositions with acetic acid treatment were prepared by first adding the $La_2O_3$ to the water, adding acetic acid dropwise with active stirring to maintain the pH at about 4 until the pH remained constant at 4 for about five minutes, and then adding the materials. The mixture was slowly heated with stirring to evaporate most of the water, dried, and calcined in air at 800° C. for six hours. The catalyst precursor (0.5 grams, 10/20 mesh) was placed in a tubular reactor and pressurized to 125 psig by methane and oxygen (9:1) at a flow rate of 750 cc/min and a GHSV of 90,000 hr$^{-1}$. It was then gradually heated to 400° C. over 1.5 hours and held for four hours. The temperature was then repeatedly ramped upward by a 50° C. increment and held for four hours, up to 650° C. Methane conversions were all about 11%. The maximum $C_2$+ selectivity, ethylene/ethane ratio, and peak temperature for each case are set forth in Table 30:

TABLE 30

| HOAc | Run | K | Mn | NbO$_3$ | Bi | $C_2$+ Selectivity | Ethylene Ethane | Peak Temperature |
|---|---|---|---|---|---|---|---|---|
| No | 2 | 0.024 | 0.012 | 0.0135 | 0.004 | 56% | 1.03 | 600° C. |
| No | 3 | 0.024 | 0.012 | 0.0045 | 0.012 | 58% | 1.16 | 600° C. |
| No | 5 | 0.024 | 0.004 | 0.0135 | 0.012 | 60% | 0.98 | 600° C. |
| No | 8 | 0.024 | 0.004 | 0.0045 | 0.004 | 63% | 1.16 | 600° C. |
| No | 9 | 0.008 | 0.012 | 0.0135 | 0.012 | 61% | 1.20 | 600° C. |
| No | 14 | 0.008 | 0.004 | 0.0135 | 0.004 | 62% | 1.22 | 600° C. |
| No | 15 | 0.008 | 0.004 | 0.0045 | 0.012 | 62% | 0.95 | 600° C. |
| No | CP | 0.016 | 0.008 | 0.0090 | 0.008 | 61% | 1.00 | 600° C. |
| Yes | 1 | 0.024 | 0.012 | 0.0135 | 0.012 | 59% | 1.08 | 600° C. |
| Yes | 4 | 0.024 | 0.012 | 0.0045 | 0.004 | 59% | 1.21 | 600° C. |
| Yes | 6 | 0.024 | 0.004 | 0.0135 | 0.004 | 62% | 1.43 | 600° C. |
| Yes | 7 | 0.024 | 0.004 | 0.0045 | 0.012 | 64% | 1.21 | 600° C. |
| Yes | 10 | 0.008 | 0.012 | 0.0135 | 0.004 | 61% | 1.04 | 550° C. |
| Yes | 11 | 0.008 | 0.012 | 0.0045 | 0.012 | 62% | 0.90 | 500° C. |
| Yes | 13 | 0.008 | 0.004 | 0.0135 | 0.012 | 62% | 1.02 | 550° C. |
| Yes | 16 | 0.008 | 0.004 | 0.0045 | 0.004 | 61% | 1.06 | 550° C. |
| Yes | CP | 0.016 | 0.008 | 0.0090 | 0.008 | 61% | 0.98 | 550° C. |

Example 46

The catalyst precursor was prepared by mixing 2.95 grams of NaNbO$_3$, 2.22 grams of Sb$_2$O$_3$, 4.59 grams of Mn(NO$_3$)$_2$·6H$_2$O, and 3.24 grams of KNO$_3$ with 150 ml of water and then adding 40.00 grams of La$_2$O$_3$. The mixture was then slowly heated with stirring to evaporate most of the water, dried, and calcined in air at 800° C. for six hours. The catalyst precursor (0.25 gram, 10/20 mesh) was then placed in a tubular reactor and pressurized by methane and oxygen. It was then gradually heated to 500° C. and held for four hours. The temperature was then repeatedly ramped upward by a 50° C. increment and held for four hours, up to 650° C. The process variables of flow rate (500–1000 cc/min), pressure (112–262 psig), and methane/oxygen ratio (6–12) were varied. The conditions used and the results obtained are set forth in Table 31:

TABLE 31

| Run | Flow Rate cc/m | Pressure psig | CH$_4$/O$_2$ ratio | Temp. °C. | Ethylene Selec. % | C$_2$ Selec. % | C$_2$ + C$_3$ Selec. % | Ethylene/ .Ethane ratio |
|---|---|---|---|---|---|---|---|---|
| 1 | 1000 | 250 | 12 | 600 | 21 | 49 | 54 | 0.78 |
| 2 | 1000 | 250 | 6 | 550 | 26 | 38 | 42 | 2.23 |
| 3 | 1000 | 125 | 6 | 550 | 27 | 45 | 48 | 1.53 |
| 4 | 500 | 250 | 12 | 550 | 17 | 47 | 52 | 0.57 |
| 5 | 500 | 250 | 6 | 550 | 21 | 34 | 38 | 1.58 |
| 6 | 500 | 125 | 12 | 600 | 20 | 57 | 62 | 0.55 |
| 7 | 500 | 125 | 6 | 550 | 27 | 51 | 56 | 1.16 |
| 8 | 750 | 188 | 9 | 550 | 31 | 59 | 64 | 1.07 |
| 9 | 450 | 188 | 9 | 600 | 26 | 54 | 59 | 0.96 |
| 10 | 750 | 262 | 9 | 550 | 23 | 46 | 50 | 0.98 |
| 11 | 750 | 112 | 9 | 600 | 29 | 58 | 63 | 0.97 |
| 12 | 750 | 188 | 12 | 600 | 29 | 64 | 71 | 0.85 |
| 13 | 750 | 188 | 6 | 600 | 25 | 40 | 44 | 1.72 |

Example 47

Catalysts of the present invention were prepared by using pre-formed a-alumina to provide supported catalysts for fixed bed or fluidized bed reactor use. The catalyst precursor was prepared by first adding 32.1 grams of 10/20 mesh α-Al$_2$O$_3$ support having a surface area of 0.85 m$^2$/g and a pore volume of 0.525 cc/g, and 19.3 grams of La(NO$_3$)$_3$·6H$_2$O to 30 ml of water, evaporating the water under vacuum at 75° C. in a rotary evaporator, and drying the impregnated solid overnight in a vacuum oven at 150° C. The impregnation and drying procedure were then repeated twice using the previously impregnated support. The dried material (three times impregnated) was then calcined at 700° C. for five hours under flowing air (200 cc/min). The impregnated support contained 24.8% La$_2$O$_3$. Then 0.065 grams of Na$_2$WO$_4$·2H$_2$O and 0.15 grams of Mn(NO$_3$)$_3$·6H$_2$O were added to 5 ml of water and the solution was mixed with 4.8 grams of the impregnated support. The water was evaporated (85° C.) and the material dried and then calcined at 800° C. for eight hours using the previous procedures. The catalyst precursor (1 gram) was placed in a tubular reactor and pressurized to 125 psig by using methane and oxygen (9:1) at a flow rate of 500 cc/min and a GHSV of 30,000 hr$^{-1}$. It was then gradually heated to 450° C. over a period of 1.5 hours and held for four hours. The temperature was then repeatedly ramped upward by a 50° C. increment and held for four hours, up to 650° C. The maximum C$_2$+ selectivity was 62.5% at 500° C.

Example 48

The catalyst precursor was prepared by first filling a glass impregnation column with 70 grams of the same α-Al$_2$O$_3$ support used in Example 47. A 30% aqueous solution of La(NO$_3$)$_3$·6H$_2$O was added to the column under vacuum for five minutes and then the system was repressurized and reevacuated several times, for a total contact time of fifteen minutes. The solution was then drained and the wet solid was dried overnight at 120° C. in a vacuum oven. The impregnation and drying procedure was repeated six times. The impregnated material was then calcined at 650° C. for five hours under flowing air (200 cc/min) directed over the material. The final-impregnated support (after seven depositions of the La component followed by drying and one final calcination) contained 43.4% La$_2$O$_3$ by weight and had a surface area of 11.1 m$^2$/g. The material was then impregnated by the same technique with a 0.0658 g/cc aqueous solution of Na$_2$WO$_4$·2H$_2$O and dried in a vacuum oven at 120° C. two hours. The material was then impregnated with a 0.1645 g/cc aqueous solution of Mn(NO$_3$)$_3$·6H$_2$O and dried overnight as before. This deposited 0.0465 grams of the sodium tungstate composition and 0.1163 grams of the manganese nitrate composition per gram of lanthanum oxide. This final impregnated material was then calcined in a muffle furnace at 700° C. for three hours under flowing air (200 cc/min). The catalyst precursor (1 gram) was placed in a tubular reactor and pressurized to 125 psig by methane and oxygen (9:1) at a flow rate of 500 cc/min and a GHSV of 30,000 hr$^{-1}$. It was then gradually heated to 450° C. over 1.5 hours and held for four hours. The temperature was then repeatedly ramped upward by a 50° C. increment and held for four hours, up to 650° C.

The maximum C$_2$ selectivity was 66% and the C$_2$+ selectivity was 73% at 550° C., with a methane conversion of 8.4% and an ethylene/ethane ratio of 0.60.

Example 49

The catalyst precursor was prepared by the same method as in Example 48, except that 14/30 mesh α-Al$_2$O$_3$ support (a binderless support of Norton, SA-5402, having a surface area of 0.85 m$^2$/g and pore volume of 0.28 cc/g) was used, the impregnation was by an aqueous solution of 40% La(NO$_3$)$_3$·6H$_2$O, and calcination was at 700° C., which gave an impregnated support that contained 46.6% La$_2$O$_3$ and had a surface area of 9.7 m$^2$/g. Thus the surface area was increased from 0.85 m$^2$/g for the support to 9.7 m$^2$/g for the catalyst precursor, which gives higher activity. The reaction was done in the same manner, with the results as set forth in Table 32:

TABLE 32

| Temperature | C$_2$ Selectivity | C$_2$+ Selectivity | Ethylene/ Ethane Ratio | Methane Conversion | Oxygen Conversion |
|---|---|---|---|---|---|
| 450° C. | — | — | — | — | 5% |
| 500° C. | 65% | 70% | 0.58 | 9.6% | 100% |
| 550° C. | 61% | 66% | 0.51 | 8.9% | 100% |
| 600° C. | 62% | 67% | 0.52 | 9.1% | 100% |

Example 50

The catalyst precursor was prepared by the same method as in Example 48, except that the impregnation was by an aqueous solution of 40% La(NO$_3$)$_3$·6H$_2$O and calcination was at 700° C., which gave an impregnated support that contained 52.3% La$_2$O$_3$ and had a surface area of 10.8 m$^2$/g.

The reaction was done in the same manner, with the results as set forth in Table 33:

TABLE 33

| Temperature | $C_2$ Selectivity | $C_2+$ Selectivity | Ethylene/Ethane Ratio | Methane Conversion | Oxygen Conversion |
|---|---|---|---|---|---|
| 450° C. | — | — | — | — | 6% |
| 500° C. | 51% | 56% | 0.52 | 9.9% | 100% |
| 550° C. | 54% | 59% | 0.54 | 10.1% | 100% |
| 600° C. | 60% | 66% | 0.64 | 10.8% | 100% |

Example 51

The catalyst precursor and procedure were the same as in Example 50, except that the catalyst precursor was gradually heated directly to 550° C. over 2 hours and then held at that temperature. The $C_2$ selectivity was 41% and the $C_2+$ selectivity was 44%, with an ethylene/ethane ratio of 0.40, a methane conversion of 9.8%, and an oxygen conversion of 100%. After one day of steady operation, the temperature was increased to 600° C. and the flow rate was increased to 700 cc/min. This increased the $C_2$ selectivity to 54%, the $C_2+$ selectivity to 58%, the ethylene/ethane ratio to 0.53, and the methane conversion to 11.2%. The conditions were held constant for fifteen days, during which the $C_2+$ selectivity (circles in FIG. 9) dropped asymptotically to a steady level of about 51%.

Example 52

The catalyst precursor and procedure were the same as in Example 49, except that the catalyst precursor was gradually heated directly to 550° C. over 2 hours and then held at that temperature. The $C_2$ selectivity was 37% and the $C_2+$ selectivity was 39%, with an ethylene/ethane ratio of 0.44, a methane conversion of 9.7%, and an oxygen conversion of 100%. After one day of steady operation, the temperature was increased to 600° C. and the flow rate was increased to 700 cc/min. This increased the $C_2$ selectivity to 57%, the $C_2+$ selectivity to 61%, the ethylene/ethane ratio to 0.62, and the methane conversion to 11.6%. The conditions were held constant for fifteen days, during which the $C_2+$ selectivity (triangles in FIG. 9) dropped asymptotically to a steady level of about 48%.

Example 53

The catalyst precursor was prepared by slurry impregnation the ring form of the same $\alpha$-$Al_2O_3$ support used in Example 47 (5/16" O.D.x⁵⁄₁₆" lengthx¹⁄₁₆" hole size) using a rotary evaporator. A solution was first prepared by mixing 125 ml of water with 0.91 grams of $Na_2WO_4 \cdot 2H_2O$ and 2.28 grams of $Mn(NO_3)_3 \cdot 6H_2O$ with stirring, followed by reflux boiling for about 15 minutes until the color changed to approximately yellow. Then 19.6 grams of $La_2O_3$ was added, and the slurry was boiled under reflux and continuous stirring for about three hours, during which it became off-white and then beige in color and more homogeneous in appearance. The resulting slurry was then mixed with 70.1 grams of the $\alpha$-$Al_2O_3$ support in a rotary evaporator, and the impregnation was conducted at a temperature of 70 to 85° C. under a partial vacuum of 19-inches Hg. The impregnated rings were dried overnight at 125° C. under vacuum. Excess coating on the rings was removed by sieving the dried material on a 10-mesh screen. One portion of the dried material was calcined at 600° C. and another at 800° C., under 200 cc/min of flowing air for 5 hours. After calcination, the catalyst precursors contained 14.1% and 14.4% deposited solid by weight, respectively. The reaction with each was done in the same manner as in Example 48, except that 0.5 grams of catalyst precursor was used and the temperature range was 450 to 700° C. The results for the catalyst precursor calcined at 600° C. are set forth in Table 34:

TABLE 34

| Temperature | $C_2$ Selectivity | $C_2+$ Selectivity | Ethylene/Ethane Ratio | Methane Conversion | Oxygen Conversion |
|---|---|---|---|---|---|
| 450° C. | — | — | — | — | 2% |
| 500° C. | 41% | 44% | 0.49 | 10.6% | 100% |
| 550° C. | 47% | 52% | 0.59 | 10.8% | 100% |
| 600° C. | 48% | 54% | 0.64 | 11.5% | 100% |
| 700° C. | 24% | 25% | 0.20 | 8.2% | 100% |

The results for the catalyst precursor calcined at 800° C. are set forth in Table 35:

TABLE 35

| Temperature | $C_2$ Selectivity | $C_2+$ Selectivity | Ethylene/Ethane Ratio | Methane Conversion | Oxygen Conversion |
|---|---|---|---|---|---|
| 500° C. | — | — | — | — | 2% |
| 550° C. | 50% | 55% | 0.66 | 12% | 100% |
| 600° C. | 53% | 58% | 0.65 | 12% | 100% |

Example 54

The preparation of the catalyst precursor was the same as in Example 53, except that 150 ml of aqueous acetic acid (25% volume concentration) was added to the solution. The impregnated ring catalyst precursors that were calcined at 600 and 800° C. contained 21.1% and 12.6% deposited solid, respectively. The results for the catalyst precursor calcined at 600° C. are set forth in Table 36:

TABLE 36

| Temperature | $C_2$ Selectivity | $C_2+$ Selectivity | Ethylene/Ethane Ratio | Methane Conversion | Oxygen Conversion |
|---|---|---|---|---|---|
| 550° C. | 22% | 23% | 0.23 | 1% | 20% |
| 600° C. | 42% | 45% | 0.63 | 8% | 100% |
| 650° C. | 41% | 44% | 0.61 | 8% | 100% |

The results for catalyst precursor calcined at 800° C. are set forth in Table 37:

TABLE 37

| Temperature | $C_2$ Selectivity | $C_2+$ Selectivity | Ethylene/Ethane Ratio | Methane Conversion | Oxygen Conversion |
|---|---|---|---|---|---|
| 550° C. | — | — | — | 1% | 12% |
| 600° C. | 47% | 51% | 0.68 | 8% | 100% |
| 650° C. | 32% | 34% | 0.38 | 5% | 100% |

Example 55

The catalyst was prepared by the same method as in Example 17, except that gadolinium oxide was used. Elemental analysis gave an oxygen/carbon ratio of 3.38 and an oxygen/gadolinium ratio of 2.10, which is a parameter A value of 0.97. The electron microscope micrograph showed that the catalyst had a disordered structure, but it did not have a porous microstructure. The surface area was 29 m$^2$/g.

Example 56

Catalysts were prepared by the same method as in Example 17, except that the oxides of Pr, Nd, Sm, Eu, Tb, Dy, Er, and Tm were used individually. The surface areas (m$^2$/g) were: 37 for Pr, 44 for Nd, 26 for Sm, 27 for Eu, 42 for Tb, 56 for Dy, 54 for Er, and 56 for Tm.

Example 57

The catalyst precursor was prepared by mixing 8.0 grams of rare earth oxide with 50 ml of deionized water. The mixture was then slowly heated with stirring to evaporate most of the water, dried, calcined in air at 600° C. for six hours, pressed, and broken into 10/20 mesh particles. The catalyst precursor (0.25 gram) was placed in a tubular reactor and pressurized to 125 psig by methane and oxygen in a ratio of 9:1 at a flow rate of 700 cc/min. It was then gradually heated to 400° C. over 1.5 hours and held for four hours. The temperature was then repeatedly ramped upward by a 50° C. increment and held for four hours, at 650° C. The results for different rare earth elements at 100% oxygen conversion are set forth in Table 38:

TABLE 38

| Rare Earth | Temperature | C$_2$ Selectivity | C$_2$+ Selectivity | Ethylene/ Ethane Ratio | Methane Conversion |
|---|---|---|---|---|---|
| Ce | 525° C. | 20% | 20% | 0.57 | 3.6% |
| Pr | 450° C. | 41% | 44% | 0.74 | 6.7% |
| Nd | 450° C. | 54% | 59% | 0.81 | 11.0% |
| Sm | 450° C. | 52% | 56% | 0.78 | 10.1% |
| Eu | 450° C. | 56% | 60% | 0.84 | 10.1% |
| Tb | 500° C. | 50% | 54% | 0.55 | 6.6% |
| Ho | 550° C. | 39% | 42% | 0.56 | 6.3% |
| Tm | 550° C. | 47% | 50% | 0.68 | 6.5% |
| Lu | 650° C. | 17% | 17% | 0.45 | 2.4% |

Example 58

The catalyst precursor was prepared by the same method as in Example 57 except that rare earth acetate was used. The reaction was done in the same manner, with the results as set forth in Table 39:

TABLE 39

| Rare Earth | Temperature | C$_2$ Selectivity | C$_2$+ Selectivity | Ethylene/ Ethane Ratio | Methane Conversion |
|---|---|---|---|---|---|
| Ce | 400° C. | 32% | 34% | 0.48 | 5.9% |
| Pr | 400° C. | 42% | 46% | 0.51 | 7.4% |
| Nd | 450° C. | 46% | 50% | 0.76 | 8.7% |
| Sm | 500° C. | 52% | 56% | 0.89 | 8.9% |
| Eu | 400° C. | 48% | 53% | 0.78 | 10.2% |
| Tb | 450° C. | 49% | 52% | 0.57 | 7.2% |
| Tm | 400° C. | 39% | 40% | 0.67 | 8.2% |
| Lu | 550° C. | 29% | 29% | 0.72 | 5.1% |

Example 59

The catalyst was prepared by mixing 8.0 grams of rare earth oxide in 50 ml of water and adding acetic acid dropwise with active stirring to maintain the pH at about 4 until the pH remained constant at 4 for about five minutes. The mixture was then slowly heated with stirring to evaporate most of the water, dried, and calcined in flowing air at 600° C. for six hours. The catalyst (0.25 gram, 10/20 mesh) was placed in a tubular reactor and pressurized to 125 psig by methane and oxygen in a ratio of 9:1 at a flow rate of 700 cc/min. It was then gradually heated to 400° C. over 1.5 hours and held for four hours. The temperature was then repeatedly ramped upward by a 50° C. increment and held for four hours, at 650° C. The results for different rare earth elements at 100% oxygen conversion are set forth in Table 40:

TABLE 40

| Rare Earth | Temperature | C$_2$ Selectivity | C$_2$+ Selectivity | Ethylene/ Ethane Ratio | Methane Conversion |
|---|---|---|---|---|---|
| Ce | 550° C. | 15% | 15% | 0.55 | 4.7% |
| Nd | 500° C. | 48% | 53% | 0.98 | 10.0% |
| Sm | 500° C. | 44% | 48% | 0.81 | 9.2% |
| Eu | 500° C. | 49% | 53% | 0.96 | 10.4% |
| Tb | 600° C. | 55% | 58% | 0.81 | 7.3% |
| Ho | 500° C. | 39% | 41% | 0.62 | 5.9% |
| Tm | 550° C. | 48% | 52% | 0.65 | 7.1% |
| Lu | 600° C. | 31% | 31% | 0.65 | 3.7% |

What is claimed:

1. A catalyst for the oxidative dehydrogenation of a lower hydrocarbon, said catalyst comprising: an oxycarbonate, hydroxycarbonate, and/or carbonate of at least one rare earth element selected from the group consisting of La, Pr, Nd, Sm, Eu, Gd, Tb, Dy, Ho, Er, and Tm, wherein said catalyst, when used for the oxidative dehydrogenation of said lower hydrocarbon exhibits higher selectivity to at least one higher hydrocarbon and/or lower olefin at a pressure above about 100 psig than said catalyst or a precursor of said catalyst exhibits at a pressure in the range of about atmospheric pressure to about 25 psig, and wherein at a pressure above about 100 psig said catalyst has a selectivity to said at least one higher hydrocarbon and/or lower olefin of at least 40%.

2. The catalyst of claim 1, wherein the catalyst becomes unselective at an elevated temperature, and wherein after the elevated temperature is lowered, the catalyst has a selectivity to at least one higher hydrocarbon and/or lower olefin substantially lower than 40%.

3. The catalyst of claim 1 further comprising a cocatalyst including at least one metal selected from the group consisting of V, Nb, Ta, Cr, Mo, W, Mn, Re, Fe, Co, Ni, Cu, Zn, Sn, Pb, Sb, and Bi.

4. A process for the oxidative dehydrogenation of a lower hydrocarbon to form at least one higher hydrocarbon and/or lower olefin, which comprises contacting the lower hydrocarbon with oxygen and a catalyst comprising a nonstoichiometric rare earth oxycarbonate of the formula $M_XC_YO_Z$ having a disordered and/or defect structure, wherein M is at least one rare earth element selected from the group consisting of La, Pr, Nd, Sm, Eu, Gd, Tb, Dy, Ho, Er, and Tm; X=2; Z=3+AY; A is less than about 1.8, and Y is the number of carbon atoms in the oxycarbonate, and wherein said catalyst, when used for the oxidative dehydrogenation of said lower hydrocarbon at a pressure above about 100 psig, has a selectivity of at least about 40% to at least one higher hydrocarbon and/or lower olefin.

5. The process of claim 4 conducted at a pressure greater than about 100 psig and a temperature less than about 700° C.

6. The process of claim 4, wherein the lower hydrocarbon is methane.

7. The process of claim 4, wherein the catalyst further comprises a cocatalyst comprising at least one metal selected from the group consisting of V, Nb, Ta, Cr, Mo, W, Mn, Re, Fe, Co, Ni, Cu, Zn, Sn, Pb, Sb, and Bi.

8. A process for the oxidative dehydrogenation of a lower hydrocarbon to form at least one higher hydrocarbon and/or lower olefin, which comprises contacting the lower hydrocarbon with oxygen and a catalyst comprising an oxycarbonate, hydroxycarbonate, and/or carbonate of at least one rare earth element selected from the group consisting of La, Pr, Nd, Sm, Eu, Gd, Th, Dy, Ho, Er, and Tm, wherein said catalyst, when used for the oxidative dehydrogenation of said lower hydrocarbon exhibits higher selectivity to at least one higher hydrocarbon and/or lower olefin at a pressure above about 100 psig than said catalyst or a precursor of said catalyst exhibits at a pressure in the range of about atmospheric pressure to about 25 psig, and wherein at a pressure above about 100 psig said catalyst has a selectivity to said at least one higher hydrocarbon and/or lower olefin of at least 40%.

9. The process of claim 8 conducted at a pressure greater than about 100 psig and a temperature less than about 700° C.

10. The process of claim 8, wherein the lower hydrocarbon is methane.

11. A process for the oxidative dehydrogenation of a lower hydrocarbon to form at least one higher hydrocarbon and/or lower olefin, which comprises contacting the lower hydrocarbon with oxygen and a catalyst comprising (1) an oxycarbonate, hydroxycarbonate and/or carbonate of at least one rare earth element selected from the group consisting of La, Pr, Nd, Sm, Eu, Gd, Tb, Dy, Ho, Er, and Tm; and (2) a cocatalyst including at least one metal selected from the group consisting of V, Nb, Ta, Cr, Mo, W, Mn, Re, Fe, Co, Ni, Cu, Zn, Sn, Pb, Sb, and Bi; wherein said catalyst, when used for the oxidative dehydrogenation of said lower hydrocarbon, has a selectivity of at least about 40% to at least one higher hydrocarbon and/or lower olefin.

12. The process of claim 11, wherein the lower hydrocarbon is methane.

13. A process for the oxidative coupling of a lower hydrocarbon to form at least one higher hydrocarbon and/or lower olefin, which comprises contacting the lower hydrocarbon with oxygen and a catalyst comprising (1) an oxide of at least one rare earth element selected from the group consisting of La, Pr, Nd, Sm, Eu, Gd, Th, Dy, Ho, Er, and Tm; and (2) a cocatalyst including at least one metal selected from the group consisting of V, Nb, Ta, Cr, Mo, W, Re, Fe, Co, and Ni; wherein said catalyst, when used for the oxidative dehydrogenation of said lower hydrocarbon, has a selectivity of at least about 40% to at least one higher hydrocarbon and/or lower olefin.

14. The process of claim 13, wherein the lower hydrocarbon is methane.

* * * * *